United States Patent [19]
Moore et al.

[11] Patent Number: 5,846,711
[45] Date of Patent: Dec. 8, 1998

[54] NUCLEAR HORMONE RECEPTOR-INTERACTING POLYPEPTIDES AND RELATED MOLECULES AND METHODS

[75] Inventors: David D. Moore, Hingham; Jae Woon Lee, Somerville, both of Mass.

[73] Assignee: The General Hospital Corporation, Boston, Mass.

[21] Appl. No.: 222,719

[22] Filed: Apr. 4, 1994

Related U.S. Application Data

[63] Continuation-in-part of Ser. No. 969,136, Oct. 30, 1992, abandoned.

[51] Int. Cl.⁶ .............................. C12Q 1/68; C12P 21/06; C12N 15/00; C07H 17/00
[52] U.S. Cl. .......................... 435/6; 435/69.1; 435/69.7; 435/320.1; 435/325; 536/23.1
[58] Field of Search .............................. 435/6, 69.7, 69.1, 435/240.1, 320.1; 530/350, 399; 536/23.51, 23.4, 23.1

[56] References Cited

U.S. PATENT DOCUMENTS

| | | | |
|---|---|---|---|
| 4,833,080 | 5/1989 | Brent et al. | 435/172.3 |
| 5,283,173 | 2/1994 | Fields et al. | 435/6 |

FOREIGN PATENT DOCUMENTS

| | | |
|---|---|---|
| WO 92/07072 | 4/1992 | WIPO . |
| WO 93/11235 | 6/1993 | WIPO . |
| WO 93/13129 | 7/1993 | WIPO . |

OTHER PUBLICATIONS

Zhang et al., "Retinoid X receptor is an auxiliary protein for thyroid hormone and retinoic acid receptors," Nature 355:441–446 (1992).
Bugge et al., "RXRα, a promiscuous partner of retinoic acid and thyroid hormone receptors," EMBO J. 11:1409–1418 (1992).
Wilson et al. 1991. Science 262:1296–1300.
Meyerson et al., The EMBO Journal 11:2909–2917 (1992).
Yang et al., Science 257:680–682 (1992).
Koff et al., Cell 66:1217–1228 (1991).
Tsai et al., Nature 353:174–177 (1991).
Xiong et al., Cell 65:691–699 (1991).
Draetta, Trends in Biochem. Sci. 15:378–382 (1990).
Richardson et al., Genes & Development 4:1332–1344 (1990).
Wittenberg et al., Cell 62:225–237 (1990).
Richardson et al., Cell 59:1127–1133 (1989).
Wittenberg et al., Molecular and Cellular Biology 9:4064–4068 (1989).
Pines et al., Cell 59:833–846 (1989).
Hadwiger et al., Proc. Natl. Acad. Sci. USA 86:6255–6259 (1989).
Wittenberg et al., Cell 54:1061–1072 (1988).
Gill et al., Nature 334:721–724 (1988).
Brent et al., Nature 312:612–615 (1984).
Brent et al., 43:729–736 (1985).

Dalton and Treisman, Cell 68:597–612 (1992).
Touchette, The Journal of NIH Research 3:44–46 (1991).
Chien et al., Proc. Natl. Acad. Sci. USA 88:9578–9582 (1991).
Fields and Song, Nature 340:245–246 (1989).
PCT International Search Report, Int'l Appln No. PCT/US93/10069, mailed Jan. 26 (1994).
Fearon et al., PNAS USA 89:7958–7962 (1992).
Broach et al. Gene 8 (121–133 (1979).
Celenza et al., Science 233 (1175–1180 (1986).
Celenza et al., Molecular and Cellular Biology 9, 5045–5054 (1989).
Celenza et al., Molecular and Cellular Biology 9, 5034–5044 (1989).
Curran et al., Cell 55, 395–397 (1988).
Dang et al., Molecular and Cellular Biology 11, 954–962 (1991).
Furey et al., Science 231, 704–707 (1986).
Gill et al., Cell 51:121–126 (1987).
Goff et al., Genes & Development 6, 864–875 (1992).
Hardy et al., Genes & Development 6, 801–814 (1992).
Hope et al., Cell 46, 885–894 (1986).
Hope et al., Nature 333:635–640 (1988).
Hu et al., Science 250:1400–1403 (1990).
Johnston, Microbiological Reviews 51, 458–476 (1987).
Keegan et al., Science 231, 699–704 (1986).
Kumar et al., Cell 51:941–951 (1987).
Laughon et al., Molecular and Cellular Biology 4:260–267 (1984).
Ma et al., Cell 55:443–446 (1988).
Ma et al., Cell 48:847–853 (1987).
Martin et al., Molecular and Cellular Biology 10:1908–1914 (1990).
McKnight et al., Proc. Natl. Acad. Sci. USA 84:7061–7065 (1987).
Silver et al., Proc. Natl. Acad. Sci. USA 81:5951–5955 (1984).

(List continued on next page.)

*Primary Examiner*—Karen Cochrane Carlson
*Attorney, Agent, or Firm*—Clark & Elbing LLP

[57] ABSTRACT

Disclosed is a method for determining whether a test protein is capable of interacting with a nuclear hormone receptor protein. The method involves: (a) providing a host cell which contains (i) a reporter gene operably linked to a protein binding site; (ii) a first fusion gene which expresses a first fusion protein, the first fusion protein including a nuclear hormone receptor protein covalently bonded to a binding moiety which is capable of specifically binding to the protein binding site; and (iii) a second fusion gene which expresses a second fusion protein, the second fusion protein including the test protein covalently bonded to a weak gene activating moiety; and (b) determining whether the test protein increases expression of the reporter gene as an indication of its ability to interact with the nuclear hormone receptor protein. Such an interaction may be hormone dependent, hormone independent, or hormone sensitive. Also disclosed is purified DNA encoding thyroid hormone receptor-interacting proteins and the polypeptides expressed from such DNA.

5 Claims, 37 Drawing Sheets

OTHER PUBLICATIONS

Thukral et al., Molecular and Cellular Biology, 9:2360–2369 (1988).

Wittekind et al., Molecular and Cellular Biology 8:3997–4008 (1988).

Beg, A.A., et al., "The IkB Proteins: Multifunctional Regulators of Rel/NF–kB Transcription Factors", 1993, *Genes & Develop.*, 7:2064–2070.

Ohno, H., et al., "The Candidate Proto–Oncogene bcl–3 Is Related to Genes Implicated in Cell Lineage Determination and Cell Cycle Control", 1990, *Cell*, vol. 60, pp. 991–997.

Schaufele et al. 1992 Mol. Endocrin. 6:656–665.

Burnside et al. 1990. J. Biol. Chem. 265(5):2500–2504.

Ma et al. 1987. Cell 48:847–853.

Godowski et al 1988 Science 241:812–816.

Ma et al. 1987. Cell 51: 113–119.

```
JL1                                      .MALDGPEQMELEEGKAG
                                         |   . .:  ||
SUG1                                     MTAAVTSSNIVLE..THE
```

```
 18 SGLRQYYLSKIEELQLIVNDKSQNLRRLQAQRNELNAKVRLLREELQLLQ
    ||:: |: .||:| :| :..|.:| |||:|||| || |||::::||.|||
 17 SGIKPYFEQKIQETELKIRSKTENGRRLEAQRNALNDKVRFIKDELRLLQ

68 EQGSYVGEVVRAMDKKKVLVKVHPEGKFVVDVDKNIDINDVTPNCRVALR
    | |||||||:: ...|||||||.||||:||| |:|::.|: .. ||.||
 67 EPGSYVGEVIKIVSDKKVLVKVQPEGKYIVDVAKDINVKDLKASQRVCLR

118 NDSYTLHKILPNKVDPLVSLMMVEKVPDSTYEMIGGLDKQIKEIKEVIEL
    .||| |||:| || |||||:|||||||||||||:|:||| |||||||||||
117 SDSYMLHKVLENKADPLVSIMMVEKVPDSTYDMVGGLTKQIKEIKEVIEL

168 PVKHPELFEALGIAQPKGVLLYGPPGTGKTLLARAVAHHTDCTFIRVSGS
    |||||||||.||||||||:|||||||||||||||||||||||| ||||||.
167 PVKHPELFESLGIAQPKGVILYGPPGTGKTLLARAVAHHTDCKFIRVSGA

218 ELVQKFIGEGARMVRELFVMAREHAPSIIFMDEIDSIGSSRLEGGSGGSS
    |||||:||||.|||||||||||||||||||||||||||||||.|:||..||.|
217 ELVQKYIGEGSRMVRELFVMAREHAPSIIFMDEIDSIGSTRVEGSGGGDS

268 EVQRQMLELLNQLDGFEATKNIKVIMATNRIDMLDSALLRPGRIDRKIEF
    |||| |||||||||||..|||:|||||:|:||.|||||||||||||||
267 EVQRTMLELLNQLDGFETSKNIKIIMATNRLDILDPALLRPGRIDRKIEF

318 PPPNEEARLDILKIHSRKMNLTRGINLRKIAELMPGASGAEVKGVCTEAG
    |||.  || :||:|||||||||||||||:|| | |.|||:|||||||||
317 PPPSVAARAEILRIHSRKMNLTRGINLRKVAEKMNGCSGADVKGVCTEAG

368 MYALRERRVHVTQEDFEMAVAKVMQKDSEKNMSIKKLWK 406
    |||||||:|||||||:||.|||.|:.|   :|: |||:|
367 MYALRERRIHVTQEDFELAVGKVMNKNQETAISVAKLFK 405
```

Fig. 2

1    MPGPLRGQHF YAVERRAYCE GCYVATLEKC ATCSQPILDR ILRAMGKAYH

51   PGCFTCVVCH RGLDGIPFTV DATSQIHCIE DFHRKFAPRC SVCGGAIMPE

101  PGQEETVRIV ALDRSFHIGC YKCEECGLLL SSEGECQGCY PLDGHILCKA

151  CRPGASRSSQ PPSGLTAESS MKYLLGSQFQ FPSFD*

Fig. 3A

```
JL2     30   CATCSQPILDR.ILRAMGKAYHPGCFTCVVCHRGLDGIPFTVDATSQI  76
             ||.|.|||||| :: :||.:| .|: | |. :.   |.| .|
Lin11   45   CAACAQPILDRYVFTVLGKCWHQSCLRCCDCRAPMSMTCFSRD..GLI  90

77   HCIEDFHRKFAPRCSVCGGAIMPEPGQEETVRIVALDRSFHIGCYKCEEC  126
             |  || |::. ||. | |   :    .|: ||   | |: ||| |:.|. |
        91   LCKTDFSRRYSQRCAGCDGKL....EKEDLVR.RARDKVFHIRCFQCSVC  135

127   GLLLSSEGECQGCYPLDGH.ILCKAC
             ||.. :    | ::|. .:|..
       136   QRLLDTGDQ...LYIMEGNRFVCQSD
```

Fig. 3B

```
    AACCCAATTCTTACCAGTTTGTTGCAAATCACAGGGAACNGGGGGTCTACCATTGGCTCG
  1 ---------+---------+---------+---------+---------+---------+ 60
    TTGGGTTAAGAATGGTCAAACAACGTTTAGTGTCCCTTGNCCCCCAGATGGTAACCGAGC a   N  P  I  L  T  S  L  L  Q  I  T  G  N  ?  G  S  T  I  G  S   -

AGTCCGACCCCTCCTCATCACACGCCGCCACCTGTCTCTTCGATGGCCGGCAACACCAAG
 61 ---------+---------+---------+---------+---------+---------+ 120
    TCAGGCTGGGGAGGAGTAGTGTGCGGCGGTGGACAGAGAAGCTACCGGCCGTTGTGGTTC a   S  P  T  P  P  H  H  T  P  P  P  V  S  S  M  A  G  N  T  K   -

AACCACCCGATGCTCATGAACCTTCTTAAAGATAATCCTGCCCAGGATTTCTCAACCCTT
121 ---------+---------+---------+---------+---------+---------+ 180
    TTGGTGGGCTACGAGTACTTGGAAGAATTTCTATTAGGACGGGTCCTAAAGAGTTGGGAA a   N  H  P  M  L  M  N  L  L  K  D  N  P  A  Q  D  F  S  T  L   -

TATGGAAGCAGCCCTTTAGAAAGGCAGAACTCCTCTTTCGGCTCACCCCGCATGGAAATA
181 ---------+---------+---------+---------+---------+---------+ 240
    ATACCTTCGTCGGGAAATCTTTCCGTCTTGAGGAGAAAGCCGAGTGGGGCGTACCTTTAT a   Y  G  S  S  P  L  E  R  Q  N  S  S  F  G  S  P  R  M  E  I   -

TGCTCGGGGAGCAACAAGACCAAGAAAAAGAAGTCATCAAGATTACCACCTGAGAAACCA
241 ---------+---------+---------+---------+---------+---------+ 300
    ACGAGCCCCTCGTTGTTCTGGTTCTTTTTCTTCAGTAGTTCTAATGGTGGACTCTTTGGT a   C  S  G  S  N  K  T  K  K  K  K  S  S  R  L  P  P  E  K  P   -

AAACAACGCGAGGATATAATTGCCAAAACCAGGCTTGAGGTTGGTGACTCTTGAAAGATT
301 ---------+---------+---------+---------+---------+---------+ 360
    TTTGTTGCGCTCCTATATTAACGGTTTTGGTCCGAACTCCAACCACTGAGAACTTTCTAA a   K  Q  R  E  D  I  I  A  K  T  R  L  E  V  G  D  S  *  K  I   -

TTCTTTCTTCAGGCCTAGATCAGAAAATTAAGTGCAGCAATATCATGAATTCTCAGAAGC
361 ---------+---------+---------+---------+---------+---------+ 420
    AAGAAAGAAGTCCGGATCTAGTCTTTTAATTCACGTCGTTATAGTACTTAAGAGTCTTCG a   F  F  L  Q  A  *  I  R  K  L  S  A  A  I  S  *  I  L  R  S   -

CCTTTCAGGGAGCCAGTGAGTCATACAGTATCCACAGTTGAGTCACTTAAAGATGTCAGT
421 ---------+---------+---------+---------+---------+---------+ 480
    GGAAAGTCCCTCGGTCACTCAGTATGTCATAGGTGTCAACTCAGTGAATTTCTACAGTCA a   P  F  R  E  P  V  S  H  T  V  S  T  V  E  S  L  K  D  V  S   -

ATACGAAACATTATT
481 ---------+----- 495
    TATGCTTTGTAATAA a   I  R  N  I  I   -
```

Fig. 4

(SEQ ID NO: 6)

```
       CTCAAATGTAGCACCGTCGTCTGCGTGATCTGCTTGGAGAAGCCCAAATACCGCTGTCCA
    1  ------------+---------+---------+---------+---------+---------+  60
       GAGTTTACATCGTGGCAGCAGACGCACTAGACGAACCTCTTCGGGTTTATGGCGACAGGT a      L  K  C  S  T  V  V  C  V  I  C  L  E  K  P  K  Y  R  C  P   -

GCCTGCCGCGTGCCCTACTGCTCGGTAGTCTGCTTCCGGAAGCACAAAGAACAGTGCAAC
   61  ------------+---------+---------+---------+---------+---------+ 120
       CGGACGGCGCACGGGATGACGAGCCATCAGACGAAGGCCTTCGTGTTTCTTGTCACGTTG a      A  C  R  V  P  Y  C  S  V  V  C  F  R  K  R  K  H  E  Q  C  N -

CCTGAAACTCGTCCTGTTGAGAAAAAAATAAGATCAGCTCTTCCTACCAAAACCGTAAAG
  121  ------------+---------+---------+---------+---------+---------+ 180
       GGACTTTGAGCAGGACAACTCTTTTTTTATTCTAGTCGAGAAGGATGGTTTTGGCATTTC a      P  E  T  R  P  V  E  K  K  I  R  S  A  L  P  T  K  T  V  K   -

CCTGTGGAAAACAAAGATGATGATGACTCTATAGCTGATTTTCTCAATAGTGATGAGGAA
  181  ------------+---------+---------+---------+---------+---------+ 240
       GGACACCTTTTGTTTCTACTACTACTGAGATATCGACTAAAAGAGTTATCACTACTCCTT a      P  V  E  N  K  D  D  D  D  S  I  A  D  F  L  N  S  D  E  E   -

GAAGACAGAGTTTCTTTGcagaatttaaagaatttaggggaaTctgcaacattaagaagc
  241  ------------+---------+---------+---------+---------+---------+ 300
       CTTCTGTCTCAAAGAAACgtcttaaatttcttaaatccccttAgacgttgtaattcttcg a      E  D  R  V  S  L  Q  N  L  K  N  L  G  E  S  A  T  L  R  S   - ttattgctcaatccacacctcaggcagttgatggtcaacctcgatcagggagaagacaaa
  301  ------------+---------+---------+---------+---------+---------+ 360
       aataacgagttaggtgtggagtccgtcaactaccagttggagctagtccctcttctgttt a      L  L  L  N  P  H  L  R  Q  L  M  V  N  L  D  Q  G  E  D  K   - gcaaagctcatgagagcttacatgcaagagccttGtttgtggagtttgcaGactgctgt
  361  ------------+---------+---------+---------+---------+---------+ 420
       cgtttcgagtactctcgaatgtacgttctcggaaaCaaacacctcaaacgtCtgacgaca a      A  K  L  M  R  A  Y  M  Q  E  P  L  F  V  E  F  A  D  C  C   - ttaggaattgtggagccatcccagaatgaggagtcttaagatggattattgtgctgcttg
  421  ------------+---------+---------+---------+---------+---------+ 480
       aatccttaacacctcggtagggtcttactcctcagaattctacctaataacacgacgaac a      L  G  I  V  E  P  S  Q  N  E  E  S  *  D  G  L  L  C  C  L   - ctcaagcgtgtgcttgactcctggaacctgcctGCTCCCTCTCCCAGACCAGCTAGTTTG
  481  ------------+---------+---------+---------+---------+---------+ 540
       gagttcgcacacgaactgaggaccttggacggaCGAGGGAGAGGGTCTGGTCGATCAAAC a      L  K  R  V  L  D  S  W  N  L  P  A  P  S  P  R  P  A  S  L   -

GGGCTGGGGAGCTCAGGCAAAAGAGGTTTCCAGGATGCAGATTAGGTCATGCAGGCCTTT
  541  ------------+---------+---------+---------+---------+---------+ 600
       CCCGACCCCTCGAGTCCGTTTTCTCCAAAGGTCCTACGTCTAATCCAGTACGTCCGGAAA
```

Fig. 5A

```
a      G  L  G  S  S  G  K  R  G  F  Q  D  A  D  *  V  M  Q  A  F   -
       ACCGGCATTGATGTGGCTCATGTTTCAGGCAGACTTGGGGTCCTTAAGGTGGCAAGTCCT
  601  ---------+---------+---------+---------+---------+---------+  660
       TGGCCGTAACTACACCGAGTACAAAGTCCGTCTGAACCCCAGGAATTCCACCGTTCAGGA a      T  G  I  D  V  A  H  V  S  G  R  L  G  V  L  A  V  A  S  P   -
       TTATGGAGAGAAAACTTGACATTCAGATGATTGTTTTTAAATGTTTTACTTTTGGTACAG
  661  ---------+---------+---------+---------+---------+---------+  720
       AATACCTCTCTTTTGAACTGTAAGTCTACTAACAAAAATTTACAAAATGAAAACCATGTC a      L  W  R  E  N  L  T  F  R  *  L  F  L  N  V  L  L  L  V  Q   -
       TTGATAGACATCATAAACGATATCAAGCTTACACTTCATATGGAGTTAAACTTGGTCAGT
  721  ---------+---------+---------+---------+---------+---------+  780
       AACTATCTGTAGTATTTGCTATAGTTCGAATGTGAAGTATACCTCAATTTGAACCAGTCA a      L  I  D  I  I  N  D  I  K  L  T  L  H  M  E  L  N  L  V  S   -
       GTTAATAAAATCAAAACGTGATTCTACTGTACATTGCATTATTCATAATTTAATTGTTTG
  781  ---------+---------+---------+---------+---------+---------+  840
       CAATTATTTTAGTTTTGCACTAAGATGACATGTAACGTAATAAGTATTAAATTAACAAAC a      V  N  K  I  K  T  *  F  Y  C  T  L  M  Y  S  *  F  N  C  L   -
       AAATTACATTAAATAAATCAACTAATTAAAAAAAAAAAAAAAAAA
  841  ---------+---------+---------+-----             885
       TTTAATGTAATTTATTTAGTTGATTAATTTTTTTTTTTTTTTTTT a      K  L  H  *  I  N  Q  L  I  K  K  K  K  K   -
```

Fig. 5B (SEQ ID NO: 7)

```
    TCGCTCGTGCTCGCCCGCGCCTGGCCTACCGCGGCACTCCCGGCTGCACGCTCTGCTTGG
  1 ---------+---------+---------+---------+---------+---------+ 60
    AGCGAGCACGAGCGGGCGCGGACCGGATGGCGCCGTGAGGGCCGACGTGCGAGACGAACC a   S  L  V  L  A  R  A  W  P  T  A  A  L  P  A  A  R  S  A  W  -

CCTCGCATGCCGGTGGACCTCAGCAAGTGGTCCGGGCCCTTGAGCCTGCAAGAAGTGGAC
 61 ---------+---------+---------+---------+---------+---------+ 120
    GGAGCGTACGGCCACCTGGAGTCGTTCACCAGGCCCGGGAACTCGGACGTTCTTCACCTG a   P  R  M  P  V  D  L  S  K  W  S  G  P  L  S  L  Q  E  V  D  -

GAGCAGCCGCAGCACCCGCTGCATGTCACCTACGCCGGGGCGCGTGGACGAGCTGGGCAA
121 ---------+---------+---------+---------+---------+---------+ 180
    CTCGTCGGCGTCGTGGGCGACGTACAGTGGATGCGGCCCCGCGCACCTGCTCGACCCGTT a   E  Q  P  Q  H  P  L  H  V  T  Y  A  G  A  R  G  R  A  G  Q  -

CGTGCTGACGCCCACCCAGGT
181 ---------+---------+- 201
    GCACGACTGCGGGTGGGTCCA a   R  A  D  A  H  P  G  -
```

Fig. 6

(SEQ ID NO: 8)

```
     TCTCAAGAGACTGAACAGAGATGTGAATCTCTGAACACAAGAACAGTTTATTTTTCTGAA
  1  ---------+---------+---------+---------+---------+---------+  60
     AGAGTTCTCTGACTTGTCTCTACACTTAGAGACTTGTGTTCTTGTCAAATAAAAAGACTT a    S  Q  E  T  E  Q  R  C  E  S  L  N  T  R  T  V  Y  F  S  E  -

CAGTGGGTATCTTCCTTAAATGAAAGGGAACAGGAACTTCACAACTTATTGGAGGTTGTA
     ---------+---------+---------+---------+---------+---------+ 120
 61  GTCACCCATAGAAGGAATTTACTTTCCCTTGTCCTTGAAGTGTTGAATAACCTCCAACAT a    Q  W  V  S  S  L  N  E  R  E  Q  E  L  H  N  L  L  E  V  V  -

AGCCAATGTTGTGAGGCTTCAAGTTCAGACATCACTGAGAAATCAGATGGACGTAAGGCA
 121 ---------+---------+---------+---------+---------+---------+ 180
     TCGGTTACAACACTCCGAAGTTCAAGTCTGTAGTGACTCTTTAGTCTACCTGCATTCCGT a    S  Q  C  C  E  A  S  S  S  D  I  T  E  K  S  D  G  R  K  A  -

GCTCATGAGAAACAGCATAACATTTTTCTTGATCAGATGACTATTGATGAAGATAAA
 181 ---------+---------+---------+---------+---------+------- 237
     CGAGTACTCTTTGTCGTATTGTAAAAAGAACTAGTCTACTGATAACTACTTCTATTT a    A  H  E  K  Q  H  N  I  F  L  D  Q  M  T  I  D  E  D  K  -
```

Fig. 7

(SEQ ID NO: 9)

```
      GAAGATCAAGATACCTCAAAGAATTCTAAGCTAAACTCACACCAGAAAGTAACACTTCTT
   1  ---------+---------+---------+---------+---------+---------+  60
      CTTCTAGTTCTATGGAGTTTCTTAAGATTCGATTTGAGTGTGGTCTTTCATTGTGAAGAA a     E  D  Q  D  T  S  K  N  S  K  L  N  S  H  Q  K  V  T  L  L   -

CAATTGCTACTTGGCCATAAGAATGAAGAAAATGTAGAAAAAAACACCAGCTGCAGGTGA
  61  ---------+---------+---------+---------+---------+---------+ 120
      GTTAACGATGAACCGGTATTCTTACTTCTTTTACATCTTTTTTTGTGGTCGACGTCCACT a     Q  L  L  L  G  H  K  N  E  E  N  V  E  K  N  T  S  C  R  *  -

TGATGA
 121  ------ 126
      ACTACT a     *  *   -
```

Fig. 8

(SEQ ID NO: 10)

```
     CTTACCTTAGAAAACCAAATTAAAGAAGAAAGAGAACAAGACAACTCTGAATCTCCAAAT
  1  ------------+---------+---------+---------+---------+---------+  60
     GAATGGAATCTTTTGGTTTAATTTCTTCTTTCTCTTGTTCTGTTGAGACTTAGAGGTTTA a      L  T  L  E  N  Q  I  K  E  E  R  E  Q  D  N  S  E  S  P  N   -

GGCAGAACATCACCTCTTGTGTCCCAGAATAATGAACAAGGCTCAACCTTACGGGATTTG
 61  ------------+---------+---------+---------+---------+---------+ 120
     CCGTCTTGTAGTGGAGAACACAGGGTCTTATTACTTGTTCCGAGTTGGAATGCCCTAAAC a      G  R  T  S  P  L  V  S  Q  N  N  E  Q  G  S  T  L  R  D  L   -

CTGACTACAACAGCTGGAAAGCTACGTGTGGGGTCTACAGATGCTGGCATTGCCTTTGCC
121  ------------+---------+---------+---------+---------+---------+ 180
     GACTGATGTTGTCGACCTTTCGATGCACACCCCAGATGTCTACGACCGTAACGGAAACGG a      L  T  T  T  A  G  K  L  R  V  G  S  T  D  A  G  I  A  F  A   -

CCAGTATATGCAATGGGAGCCCCAAGTAGCAAAAGTGGACGGACTATGCCTAACATTCTT
181  ------------+---------+---------+---------+---------+---------+ 240
     GGTCATATACGTSACCCTCGGGGSTCATCGSSTTCACC~GCCT&ATACGGATSGTAAGAA a      P  V  Y  A  M  G  A  P  S  S  K  S  G  R  T  M  P  N  I  L   -

GATGACATAATTGCTTCAGTTGTTGAAAACAAAATTCCACCAAGTAAAAACCTCCAAGATA
241  ------------+---------+---------+---------+---------+---------+ 300
     CTACTGTATTAACGAAGTCAACAACTTTTGTTTSAAGGTGGTTCATTTTGGAGGTTCTAT a      D  D  I  I  A  S  V  V  E  N  K  I  P  P  S  K  T  S  K  I   -

AATGTAAAACCAGAGCTTAAAGAAGAGCCTGAAGAAAGCATAATATCTGCAGTGGATGAA
301  ------------+---------+---------+---------+---------+---------+ 360
     TTACATTTTGGTCTCGAATTTCTTCTCGGACTTCTTTCGTATTATAGACGTCACCTACTT a      N  V  K  P  F  L  K  E  E  P  E  E  S  I  I  S  A  V  D  E   -

AATAATAAATTATACAGTGATATACCACATTCTTGGATCTGTGAGAAGCATATTTTATGG
361  ------------+---------+---------+---------+---------+---------+ 420
     TTATTATTTAATATGTCACTATATGGTGTAAGAACCTAGACACTCTTCGTATAAAATACC a      N  N  K  L  Y  S  D  I  P  H  S  W  I  C  E  K  H  I  L  W   -

CTTAGGATTATAAGAATAGCAGTAATTGGAAGCTTTTCAAAGAATGTTGGAAACAACGAC
421  ------------+---------+---------+---------+---------+---------+ 480
     GAATCCTAATATTCTTATCGTCATTAACCTTCGAAAAGTTTCTTACAACCTTTGTTGCTG a      L  R  I  I  R  I  A  V  I  G  S  F  S  K  N  V  G  N  K  D   -

AGCCTGCAGTGGTTTCTGGTGTGCATAAGAAAATGAACATTAGCCTATGGAAGGCGGAAT
481  ------------+---------+---------+---------+---------+---------+ 540
     TCGGACGTCACCAAAGACCACACGTATTCTTTTACTTGTAATCGGATACCTTCCGCCTTA a      S  L  Q  W  F  L  V  C  I  R  K  *  T  L  A  Y  G  R  R  N   -

CAATTAGTCTTGATTTTGGAGACCACCAAG
541  ------------+---------+--------+ 570
     GTTAATCAGAACTAAAACCTCTGGTGGTTC a      Q  L  V  L  I  L  E  T  T  K   -
```

Fig. 9

(SEQ ID NO: 11)

```
    AACCATACCCCTGGCGCCTTGTACCCCGATTCCGACTTGGAGAAGGAAGAAGAGGAGAGT
  1 ------------------------------------------------------------  60
    TTGGTATGGGGACCGCGGAACATGGGGCTAAGGCTGAACCTCTTCCTTCTTCTCCTCTCA a   N  H  T  P  G  A  L  Y  P  D  S  D  L  E  K  E  E  E  E  S   -

GAGGAGGACTGGAAGCTGCAGCTGGAGGCTGAAAACTACGAGGGCCACACCCCACTCCAC
 61 ------------------------------------------------------------ 120
    CTCCTCCTGACCTTCGACGTCGACCTCCGACTTTTGATGCTCCCGGTGTGGGGTGAGGTG a   E  E  D  N  K  L  Q  L  E  A  E  N  Y  E  G  H  T  P  L  H   -

GTGGCCGTTATCCACAAAGATGTGGAGATGGTCCGGCTGCTCCGAGATGCTGGAGCTGAC
121 ------------------------------------------------------------ 180
    CACCGGCAATAGGTGTTTCTACACCTCTACCAGGCCGACGAGGCTCTACGACCTCGACTG a   V  A  V  I  H  K  D  V  E  M  V  R  L  L  R  D  A  G  A  D   -

CTTGACAAACCGGAGCCCACGTGCGGCCGGAGCCCCTTCATTTGGCAGTGGAGGCCAGGC
181 ------------------------------------------------------------ 240
    GAACTGTTTGGCCTCGGGTGCACGCCGGCCTCGGGGAAGTAAACCGTCACCTCCGGTCCG a   L  D  K  P  E  P  T  C  G  R  S  P  F  I  W  Q  W  R  P  G   -

AGCCGATGTGCTGGAGCTTCTCTGAGGGCAGGCGCGAACCCTGCTGCCCGCATGTACGGT
241 ------------------------------------------------------------ 300
    TCGGCTACACGACCTCGAAGAGACTCCCGTCCGCGCTTGGGACGACGGGCGTACATGCCA a   S  R  C  A  G  A  S  L  R  A  G  A  N  P  A  A  R  M  Y  G   -

GGCCGCACCCCACTCGGCAGTGCCATGCTCCGGCCCAACCCCATCCTCGCCCGCCTCCTC
301 ------------------------------------------------------------ 360
    CCGGCGTGGGGTGAGCCGTCACGGTACGAGGCCGGGTTGGGGTAGGAGCGGGCGGAGGAG a   G  R  T  P  L  G  S  A  M  L  R  P  N  P  I  L  A  R  L  L   -

CGTGCACACGGAGCCCCTGAGCCCGAGGGGAAGGACGAGAAATCCGGCCCCTGCAGCAGC
361 ------------------------------------------------------------ 420
    GCACGTGTGCCTCGGGGACTCGGGCTCCCCTTCCTGCTCTTTAGGCCGGGGACGTCGTCG a   R  A  H  G  A  P  E  P  E  G  K  D  E  K  S  G  P  C  S  S   -

AGTAGCGAGCACGACNAGAGANGACGAgggcGATGAATACGACGACATTGTGGTTCACAG
421 ------------------------------------------------------------ 480
    TCATCGCTCGTGCTGNTCTCTNCTGCTcccgCTACTTATGCTGCTGTAACACCAAGTGTC a   S  S  E  H  D  ?  R  ?  R  G  R  *  I  R  R  H  C  G  S  Q   -

CAGCCGCAGCCAAACCCGGCTGCCTCCCACCCCAGCCTCAAAACCTCTTCCTGACGACCC
481 ------------------------------------------------------------ 540
    GTCGGCGTCGGTTTGGGCCGACGGAGGGTGGGGTCGGAGTTTTGGAGAAGGACTGCTGGG a   Q  P  Q  P  N  P  A  A  S  H  P  S  L  K  T  S  S  *  R  P   -

CCGCCCCGTGTGATTTGTTTCATTGTTAATATAATTTCCAGTTTAATAAACAAAACCCTA
```

Fig. 10A

```
541 ----------+---------+---------+---------+---------+---------+ 600
    GGCGGGGCACACTAAACAAAGTAACAATTATATTAAAGGTCAAATTATTTGTTTTGGGAT a    P  P  R  V  I  C  F  I  V  N  I  I  S  S  L  I  N  K  T  L

GTTCTGACAACCAGAAAAAAAAAA
601 ----------+---------+---- 624
    CAAGACTGTTGGTCTTTTTTTTTT a    V  L  T  T  R  K  K   -
```

Fig. 10B (SEQ ID NO. 12)

```
    AGACACCCGCTGATCAGAGACATGCTTCGACGAATTAAGGAAGAAGAGGATCTGGGTAAA
 1  ---------+---------+---------+---------+---------+---------+ 60
    TCTGTGGGCGACTAGTCTCTGTACGAAGCTGCTTAATTCCTTCTTCTCCTAGACCCATTT a   R  H  P  L  I  R  D  M  L  R  R  I  K  E  E  E  D  L  G  K  -

AGTAGAGAAGGATCAAGGACGGATGATGAAGTAGTACAG
61  ---------+---------+---------+--------- 99
    TCATCTCTTCCTAGTTCCTGCCTACTACTTCATCATGTC a   S  R  E  G  S  R  T  D  D  E  V  V  Q  -
```

Fig. 11

(SEQ ID NO. 13)

```
      CAGGTGGAAGAAAACACCCCGTACTGGCAGGCATGGAGCCAACAAGGAGAACCTGGAGCT
   1  ------------+---------+---------+---------+---------+---------+ 60
      GTCCACCTTCTTTTGTGGGGCATGACCGTCCGTACCTCTGTTGTTCCTCTTGGACCTCCA a     Q  V  E  E  N  T  P  Y  W  Q  A  W  S  Q  Q  G  E  P  G  A   -

CAACGGCAGCATCCTGAGTGCGAGAACTTTCAAAGGCTTCCAAATCTGATGCTACTTCTG
  61  ------------+---------+---------+---------+---------+---------+ 120
      GTTGCCGTCGTAGGACTCACGCTCTTGAAAGTTTCCGAAGGTTTAGACTACGATGAAGAC a     Q  R  Q  H  P  E  C  E  N  F  Q  R  L  P  N  L  M  L  L   -

GAATCCTCAATTCAACCAACATCCAGTCCTGAGAAGCCCTGATCAGTCAACCAGCTGTGG
 121  ------------+---------+---------+---------+---------+---------+ 180
      CTTAGGAGTTAAGTTGGTTGTAGGTCAGGACTCTTCGGGACTAGTCAGTTGGTCGACACC a     E  S  S  I  Q  P  T  S  S  P  E  K  P  *  S  V  N  Q  L  W  -

CTTCCTGTGCCTAGACTGGACCTAATTATATGGGGG
 181  ------------+---------+---------+------ 216
      GAAGGACACGGATCTGACCTGGATTAATATACCCCC a     L  P  V  P  R  L  D  L  I  I  W  G   -
```

Fig. 12

(SEQ ID NO. 14)

```
      TGCCGCTGCAGCAGCGCAGTTCCAGTCCGTTGCTTTACTTTTTGCTTCACCGACATAGTC
   1  ------------+---------+---------+---------+---------+---------+  60
      ACGGCGACGTCGTCGCGTCAAGGTCAGGCAACGAAATGAAAAACGAAGTGGCTGTATCAG a     C  R  C  S  S  A  V  P  V  R  C  F  T  F  C  F  T  D  I  V   -

ATTATGCCGAAGAGAAAGTCTCCAGAGAATACAGAGGGCAAAGATGGATCCAAAGTAACT
  61  ------------+---------+---------+---------+---------+---------+  120
      TAATACGGCTTCTCTTTCAGAGGTCTCTTATGTCTCCCGTTTCTACCTAGGTTTCATTGA a     I  M  P  K  R  K  S  P  E  N  T  E  G  K  D  G  S  K  V  T   -

AAACAGGAGCCCACAAGACGGTCTGCCAGATTGTCAGCGAAACCTGCTCCACCAaaacct
 121  ------------+---------+---------+---------+---------+---------+  180
      TTTGTCCTCGGGTGTTCTGCCAGACGGTCTAACAGTCGCTTTGGACGAGGTGGTtttgga a     K  Q  E  P  T  A  R  R  A  R  L  S  A  K  P  A  P  P  K  P   - gaacccaaaccaagaaaaacatctgctaagaaagaacctGGAGCAAAGATTAGCAGAGGT
 181  ------------+---------+---------+---------+---------+---------+  240
      cttgggtttggttcttttttgtagacgattctttcttggaCCTCGTTTCTAATCGTCTCCA a     E  P  K  P  A  R  T  S  A  K  K  E  P  G  A  K  I  S  R  G   -

GCTAAAGGGAGGAAGGAGGAAAAGCAGGAAGCTGGAAAGGAAGGTACTGCACCATCTGAA
 241  ------------+---------+---------+---------+---------+---------+  300
      CGATTTCCCTCCTTCCTCCTTTTCGTCCTTCGACCTTTCCTTCCATGACGTGGTAGACTT a     A  K  G  R  K  E  E  K  Q  E  A  G  K  E  G  T  A  P  S  E   -

AATGGTGAAACTAAAGCTGAAGAGGCACAGAAAACTGAATCTGTAGATAACGAGGGAGAA
 301  ------------+---------+---------+---------+---------+---------+  360
      TTACCACTTTGATTTCGACTTCTCCGTGTCTTTTGACTTAGACATCTATTGCTCCCTCTT a     N  G  E  T  K  A  E  E  A  Q  K  T  E  S  V  D  N  E  G  E   -

TGAATTGTCATGAAAAATTGGGGTTGATTTTATGTATCTCTTGGGACAACTTTTAAAAGC
 361  ------------+---------+---------+---------+---------+---------+  420
      ACTTAACAGTACTTTTTAACCCCAACTAAAATACATAGAGAACCCTGTTGAAAATTTTCG a     *  I  V  M  K  N  W  G  *  F  Y  V  S  L  G  T  T  F  K  S   -

TATTTTTACCAAGTATTTTGTAAATGCTAATTTTTTAGGACTCTACTAGTTGGCATACGA
 421  ------------+---------+---------+---------+---------+---------+  480
      ATAAAAATGGTTCATAAAACATTTACGATTAAAAAATCCTGAGATGATCAACCGTATGCT a     Y  F  Y  Q  V  F  C  K  C  *  F  F  R  T  L  L  V  G  I  R   -

AAATATATAAGGATGGACATTTATCGTCTCATAGTCATGCTTTTTGGAATTTNNNNNNNN
 481  ------------+---------+---------+---------+---------+---------+  540
      TTTATATATTCCTACCTGTAAATAGCAGAGTATCAGTACGAAAAACCTTAAANNNNNNNN a     K  Y  I  R  M  D  I  Y  R  L  I  V  M  L  F  G  I  ?  ?  ?   -

NNNNNNNNNNNNNNNNNNNNCAGGAAGTTTGCCCCAAGATGCTCAGTGTGCCGTGGGGCCA
 541  ------------+---------+---------+---------+---------+---------+  600
      NNNNNNNNNNNNNNNNNNNNGTCCTTCAAACGGGGTTCTACGAGTCACACGGCACCCCGGT
```

Fig. 13A

```
a      ? ? ? ? ? ? ? G S L P Q D A Q C A V G P  -
       TAACTGCCTGAGCCAGGTCAGGAGGAGACTGCTG
  601  ---------+---------+---------+----  634
       ATTGACGGACTCGGTCCAGTCCTCCTCTGACGAC
a      * L P E P G Q E E T A  -
```

Fig. 13B (SEQ ID NO. 15)

```
      AAACATCCTATCATCTGTAGGCTCATTCATTTCTCTAACAGCAGCAGCAACAGCGCATCA
   1  ---------+---------+---------+---------+---------+---------+  60
      TTTGTAGGATAGTAGACATCCGAGTAAGTAAAGAGATTGTCGTCGTCGTTGTCGCGTAGT a     K   H   P   I   I   C   R   L   I   H   F   S   N   S   S   S   N   S   A   S   -

CAGGACACCAAGGAGAGCTCTGAAGAGCCTCCCTCAGAAGAGAGCCAGGACACCCCCATT
  61  ---------+---------+---------+---------+---------+---------+ 120
      GTCCTGTGGTTCCTCTCGAGACTTCTCGGAGGGAGTCTTCTCTCGGTCCTGTGGGGGTAA a     Q   D   T   K   E   S   S   E   E   P   P   S   E   E   S   Q   D   T   P   I   -

TACACGGAGTTTGATGAGGATTTCGAGGAGGAACCCACATCCCCCATAGGTCACTGTGTG
 121  ---------+---------+---------+---------+---------+---------+ 180
      ATGTGCCTCAAACTACTCCTAAAGCTCCTCCTTGGGTGTAGGGGGTATCCAGTGACACAC a     Y   T   E   F   D   E   D   F   E   E   E   P   T   S   P   I   G   H   C   V   -

GCCATCTACCACTTTGAAGGGTCCAGCGAGGGCACTATCTCTATGGCCGAGGGTGAAGAC
 181  ---------+---------+---------+---------+---------+---------+ 240
      CGGTAGATGGTGAAACTTCCCAGGTCGCTCCCGTGATAGAGATACCGGCTCCCACTTCTG a     A   I   Y   H   F   E   G   S   S   E   G   T   I   S   M   A   E   G   E   D   -

CTCAGTCTTATGGAAGAAGACAAAGGGGACGGCTGGACCCGGGTCAGGCGGAAAGAGGGA
 241  ---------+---------+---------+---------+---------+---------+ 300
      GAGTCAGAATACCTTCTTCTGTTTCCCCTGCCGACCTGGGCCCAGTCCGCCTTTCTCCCT a     L   S   L   M   E   E   D   K   G   D   G   W   T   R   V   R   R   K   E   G   -

GGCGAGGGCTACGTGCCCACCTCCTACCTCCGAGTCACGCTCAATTGAACCCTGCCAGAG
 301  ---------+---------+---------+---------+---------+---------+ 360
      CCGCTCCCGATGCACGGGTGGAGGATGGAGGCTCAGTGCGAGTTAACTTGGGACGGTCTC a     G   E   G   Y   V   P   T   S   Y   L   R   V   T   L   N   *   T   L   P   E   -

ACGGGAAGAGGGGGGCTGTCGGCTGCTGCTTCTGGGCCACGGGGAGCCCCAGGACCTATG
 361  ---------+---------+---------+---------+---------+---------+ 420
      TGCCCTTCTCCCCCCGACAGCCGACGACGAAGACCCGGTGCCCCTCGGGGTCCTGGATAC a     T   G   R   G   G   L   S   A   A   A   S   G   P   R   G   A   P   G   P   M   -

CACTTTATTTCTGACCCCGTGGCTTCGGCTGAGACCTGTGTAACCTGCTGCCCCCTCCAC
 421  ---------+---------+---------+---------+---------+---------+ 480
      GTGAAATAAAGACTGGGGCACCGAAGCCGACTCTGGACACATTGGACGACGGGGGAGGTG a     H   F   I   S   D   P   V   A   S   A   E   T   C   V   T   C   C   P   L   H   -

CCCCAACCCAGTCCTACCTGTCACACCGGACGGACCCGCTGTGCCTTCTACCATCGTTCC
 481  ---------+---------+---------+---------+---------+---------+ 540
      GGGGTTGGGTCAGGATGGACAGTGTGGCCTGCCTGGGCGACACGGAAGATGGTAGCAAGG a     P   Q   P   S   P   T   C   H   T   G   R   T   R   C   A   F   Y   H   R   S   -

ACCATTGATGTACATACTCATGTTTTACATCTTTTCTTTCTGCGCTCGGCTCCGGCCATT
 541  ---------+---------+---------+---------+---------+---------+ 600
      TGGTAACTACATGTATGAGTACAAAATGTAGAAAAGAAAGACGCGAGCCGAGGCCGGTAA
```

TTGTTTTATACAAAAATGGGAAAAAAAAAAAAAAAAAAA
601  ---------+---------+---------+--------  638
     AACAAAATATGTTTTTACCCTTTTTTTTTTTTTTTTTTT a    L  F  Y  T  K  M  G  K  K  K  K         -
```

Fig. 14B (SEQ ID NO. 16)

```
    GGCACGAGGCGTGACGTCCGACAAGAAATGCTGGATGATGTACAAAAGAAATTGATGAGC
  1 ------------+---------+---------+---------+---------+---------+ 60
    CCGTGCTCCGCACTGCAGGCTGTTCTTTACGACCTACTACATGTTTTCTTTAACTACTCG a    G  T  R  R  D  V  R  Q  E  M  L  D  D  V  Q  K  K  L  M  S    -

TTAGCAAACAGCTCAGAAGGAAAAGTAGACAAAGTCCTAATGAGAAACCTCTTCATTGGT
 61 ---------+---------+---------+---------+---------+---------+ 120
    AATCGTTTGTCGAGTCTTCCTTTTCATCTGTTTCAGGATTACTCTTTGGAGAAGTAACCA a    L  A  N  S  S  E  G  K  V  D  K  V  L  M  R  N  L  F  I  G   -

CATTTCCACACACCGAAAAATCAGCGTCATGAAGTGTTACGGTTAATGGGGAGCATCCTG
121 ---------+---------+---------+---------+---------+---------+ 180
    GTAAAGGTGTGTGGCTTTTTAGTCGCAGTACTTCACAATGCCAATTACCCCTCGTAGGAC a    H  F  H  T  P  K  N  Q  R  H  E  V  L  R  L  M  G  S  I  L   -

GGCGTCAGAAGGGAGGAGATGGAGCAGTTGTTTCATGACGATCAGGGCAGTGTTACCAGG
181 ---------+---------+---------+---------+---------+---------+ 240
    CCGCAGTCTTCCCTCCTCTACCTCGTCAACAAAGTACTGCTAGTCCCGTCACAATGGTCC a    G  V  R  R  E  E  M  E  Q  L  F  H  D  D  Q  G  S  V  T  R   -

TGGATGACTGGGTGGCTTGGAGGAGGATCAAAAAGTGTTCCCAACACACCTTTGAGACCA
241 ---------+---------+---------+---------+---------+---------+ 300
    ACCTACTGACCCACCGAACCTCCTCCTAGTTTTTCACAAGGGTTGTGTGGAAACTCTGGT a    W  M  T  G  W  L  G  G  G  S  K  S  V  P  N  T  P  L  R  P   -

AATCAGCAATCTGTGGTTAATAGTTCTTTTTCAGAACTTTTTGTTAAATTTCTAGAAACA
301 ---------+---------+---------+---------+---------+---------+ 360
    TTAGTCGTTAGACACCAATTATCAAGAAAAAGTCTTGAAAAACAATTTAAAGATCTTTGT a    N  Q  Q  S  V  V  N  S  S  F  S  E  L  F  V  K  F  L  E  T   -

GAATCTCATCCATCCATTCCACCACCAAAGCTTTCTGTTCATGATATGAAACCTCTGGAT
361 ---------+---------+---------+---------+---------+---------+ 420
    CTTAGAGTAGGTAGGTAAGGTGGTGGTTTCGAAAGACAAGTACTATACTTTGGAGACCTA a    E  S  H  P  S  I  P  P  P  K  L  S  V  H  D  M  K  P  L  D   -

TCACCAGGAAGAAGAAAAAGAGATACAAATGCACCAGAAAGTTTTAAAGATACAGCAGAA
421 ---------+---------+---------+---------+---------+---------+ 480
    AGTGGTCCTTCTTCTTTTTCTCTATGTTTACGTGGTCTTTCAAAATTTCTATGTCGTCTT a    S  P  G  R  R  K  R  D  T  N  A  P  E  S  F  K  D  T  A  E   -

TCCAGGTCTGGTAGAAGAACAGATGTAAATCCGTTTTTGGCTCCTcgctcggcagctgta
481 ---------+---------+---------+---------+---------+---------+ 540
    AGGTCCAGACCATCTTCTTGTCTACATTTAGGCAAAAACCGAGGAgcgagccgtcgacat a    S  R  S  G  R  R  T  D  V  N  P  F  L  A  P  R  S  A  A  V   - cctcttattaacccagctggacttggacttggtgggccgggcatcttcttctgaaaccca
541 ---------+---------+---------+---------+---------+---------+ 600
    ggagaataattgggtcgacctgaacctggaccacccggcccgtagaagaagactttgggt
```

Fig. 15A

```
a      P  L  I  N  P  A  G  L  G  P  G  G  P  G  I  F  F  *  N  P   -
    tctcagatgttttgcccacatttacacctttgccagcgttacctgacaacagtgctgggg
601 ---------+---------+---------+---------+---------+---------+ 660
    agagtctacaaaacgggtgtaaatgtggaaacggtcgcaatggactgttgtcacgacccc a      S  Q  M  F  C  P  H  L  H  L  C  Q  R  Y  L  T  T  V  L  G   -
    ttgtgctgaaagccttttaaagcaatagatgattctcaagccagagacaatctagcactt
661 ---------+---------+---------+---------+---------+---------+ 720
    aacacgactttcggaaaatttcgttatctactaagagttcggtctctgttagatcgtgaa a      L  C  *  K  P  F  K  A  I  D  D  S  Q  A  R  D  N  L  A  L   -
    taaagaaaccatgaacactatatgtatgtactttatcacaaagtggcctttggggagaaa
721 ---------+---------+---------+---------+---------+---------+ 780
    atttctttggtacttgtgatatacatacatgaaatagtgtttcaccggaaaccctcttt a      *  R  N  H  E  H  Y  M  Y  V  L  Y  H  K  V  A  F  G  E  K   -
    gtcatgtatttgttcgcaattatgctttctctgaatttaataaaaatattcctaatgctt
781 ---------+---------+---------+---------+---------+---------+ 840
    cagtacataaacaagcgttaatacgaaagagacttaaattatttttataaggattacgaa a      V  M  Y  L  F  A  I  M  L  S  L  N  L  I  K  I  F  L  M  L   -
    ttagaaaaaaaaaaaaaaaaaa
841 ---------+---------+--- 862
    aatctttttttttttttttttt a      L  E  K  K  K  K  K    -
```

Fig. 15B (SEQ ID NO: 17)

```
    GGCACGAGGCGAGTTCTCCCACCTGAGCAGAAATATGACCATGCAGCGCACCATGAAGCT
 1  ------------+---------+---------+---------+---------+---------+ 60
    CCGSGCTCCGCTCAAGAGGGUGGACSCGTCT$TATACTGG$ACGTCGCGTGGTAC$$CGA a   G  T  R  R  V  L  P  P  E  Q  K  Y  D  H  A  A  H  H  E  A  -

CTACCGACTGCCAGAGACTCCCAAGACAGCTGGGCTGCGACCAATGGAAACAAAGGACAT
 61 ---------+---------+---------+---------+---------+---------+ 120
    GATGGCTGACGGTCTCTGAGGGTTCTGTCGACCCGACGCTGGTTACCTTTGTTTCCTGTA a   L  P  T  A  R  D  S  Q  D  S  W  A  A  T  N  G  N  K  G  H  -

TCCAGTAGTGCACCAGCTCCTCACCAGGTACTTGAAGCAATTTCACCTTACGCCCGTCAT
121 ---------+---------+---------+---------+---------+---------+ 180
    AGGTCATCACGTGGTCGAGGAGTGGTCCATGAACTTCGTTAAAGTGGAATGCGGGCAGTA a   S  S  S  A  P  A  P  H  Q  V  L  E  A  I  S  P  Y  A  R  H  -

GAGCCAGGAGGAGGTGGAGCACTGGTTCTACCCCCAGGAGAATATCATCGACACTTTCGT
181 ---------+---------+---------+---------+---------+---------+ 240
    CTCGGTCCTCCTCCACCTCGTGACCAAGATGGGGGTCCTCTTATAGTAGCTGTGAAAGCA a   E  P  G  G  G  A  L  V  L  P  P  G  E  Y  H  R  H  F  R  -

GGSGGAG
241 ------- 247
    CCACCTC a   G  G  -
```

Fig. 16

(SEQ ID NO: 18)

```
    agggcgcacctggagctgTTCTGGTCTAGAGTGAATATCCCCAAGGTGCTAAGAGCTGCA
 1  ------------+---------+---------+---------+---------+---------+ 60
    tcccgcgtggacctcgacAAGACCAGATCTCACTTATAGGGGTTCCACGATTCTCGACGT a   R  A  H  L  E  L  F  W  S  R  V  N  I  P  K  V  L  R  A  A  -

GAACAAGCTCATCTTTGGGCAGACTGGTGTTTTTGTATGACA
61  ---------+---------+---------+---------+-- 102
    CTTGTTCGAGTAGAAACCCGTCTGACCACAAAAACATACTGT a   E  Q  A  H  L  W  A  D  W  C  F  C  M  T  -
```

Fig. 17

(SEQ ID NO: 19)

```
     GTTAGCTCTAGAGGCCATTCTTTTGCTGATCCTGCCAGTAATCTTGGGCTGGAAGACATT
   1 ---------+---------+---------+---------+---------+---------+ 60
     CAATCGAGATCTCCGGTAAGAAAACGACTAGGACGGTCATTAGAACCCGACCTTCTGTAA a    V  S  S  R  G  H  S  F  A  D  P  A  S  N  L  G  L  E  D  I  -

ATCAGGAAGGCTCTCATGGGAAGCTTTGATGACAAAGTTGAGGATCATGGAGTTGTCATG
  61 ---------+---------+---------+---------+---------+---------+ 120
     TAGTCCTTCCGAGAGTACCCTTCGAAACTACTGTTTCAACTCCTAGTACCTCAACAGTAC a    I  R  K  A  L  M  G  S  F  D  D  K  V  E  D  H  G  V  V  M  -

TCCCAGCCTATGGGAGTAGTGCCTGGTACTGCCAACACCGATTGCATGTGCTCCCTCTGC
 121 ---------+---------+---------+---------+---------+---------+ 180
     AGGGTCGGATACCCTCATCACGGACCATGACGGTTGTGGCTAACGTACACGAGGGAGACG a    S  Q  P  M  G  V  V  P  G  T  A  N  T  D  C  M  C  S  L  C  -

GGTGAACCAAGCAGCTCCTCACCAACAGAACAGGATCTG
 181 ---------+---------+---------+--------- 219
     CCACTTGGTTCGTCGAGGAGTGGTTGTCTTGTCCTAGAC a    G  E  P  S  S  S  S  P  T  E  Q  D  L  -
```

Fig. 18

(SEQ ID NO: 20)

```
    AATATCGAACTGAAGAAAGGAGGGAAGGATATACCAGTCACTATCCACAATTTAGAGGAG
  1 ------------+---------+---------+---------+---------+---------+ 60
    TTATAGCTTGACTTCTTTCCTCCCTTCCTATATGGTCAGTGATAGGTGTTAAATCTCCTC a   N  I  E  L  K  K  G  G  K  D  I  P  V  T  I  H  N  L  E  E   -

TATCTAAGACTGGTTATATTCTGGGCACTAAATGAAGGCGTTTCTAGGCAATTTGATTCG
 61 ------------+---------+---------+---------+---------+---------+ 120
    ATAGATTCTGACCAATATAAGACCCGTGATTTACTTCCGCAAAGATCCGTTAAACTAAGC a   Y  L  R  L  V  I  F  W  A  L  N  E  G  V  S  R  Q  F  D  S   -

TTCAGAGATGGATTTGAATCAGTCTTCCCACTCAGTCATCTTCAGTACTTCTACCCGGAG
121 ------------+---------+---------+---------+---------+---------+ 180
    AAGTCTCTACCTAAACTTAGTCAGAAGGGTGAGTCAGTAGAAGTCATGAAGATGGGCCTC a   F  R  D  G  F  E  S  V  F  P  L  S  H  L  Q  Y  F  Y  P  E   -

GAACTGGATCAGCTCCTTTGTGGCAGTAAAGCAGACACTTGGGATGCAAAGACACTGATG
181 ------------+---------+---------+---------+---------+---------+ 240
    CTTGACCTAGTCGAGGAAACACCGTCATTTCGTCTGTGAACCCTACGTTTCTGTGACTAC a   E  L  D  Q  L  L  C  G  S  K  A  D  T  W  D  A  K  T  L  M   -

GAATGCTGTAGGCCTGATCATGGTTATACTCATGACAGTCGGGCTGTGAAGTTTTTGTTT
241 ------------+---------+---------+---------+---------+---------+ 300
    CTTACGACATCCGGACTAGTACCAATATGAGTACTGTCAGCCCGACACTTCAAAAACAAA a   E  C  C  R  P  D  H  G  Y  T  H  D  S  R  A  V  K  F  L  F   -

GAGATTCTCAGTAGTTTTGATAATGAGCAGCAGAGGTTATTTCTCCAGTTTGTGACTGGT
301 ------------+---------+---------+---------+---------+---------+ 360
    CTCTAAGAGTCATCAAAACTATTACTCGTCGTCTCCAATAAAGAGGTCAAACACTGACCA a   E  I  L  S  S  F  D  N  E  Q  Q  R  L  F  L  Q  F  V  T  G   -

AGCCCAAGATTGCCTGTTGGAGGATTCCGGAGTTTGAATCCACCTTTGACAATTGTCCGA
361 ------------+---------+---------+---------+---------+---------+ 420
    TCGGGTTCTAACGGACAACCTCCTAAGGCCTCAAACTTAGGTGGGAAACTGTTAACAGCT a   S  P  R  L  P  V  G  G  F  R  S  L  N  P  P  L  T  I  V  R   -

AAGACGTTTGAATCAACAGAAAACCCAGATGACTTCTTGCCCTCTGTAATGACTTGTGTG
421 ------------+---------+---------+---------+---------+---------+ 480
    TTCTGCAAACTTAGTTGTCTTTTGGGTCTACTGAAGAACGGGAGACATTACTGAACACAC a   K  T  F  E  S  T  E  N  P  D  D  F  L  P  S  V  M  T  C  V   -

AACTATCTTAAGTTGCCGGACTATCAAGCATTGAGATATGCGTGAAAAACTGTTGATAGC
481 ------------+---------+---------+---------+---------+---------+ 540
    TTGATAGAATTCAACGGCCTGATAGTTCGTAACTCTATACGCACTTTTTGACAACTATCG a   N  Y  L  K  L  P  D  Y  Q  A  L  R  Y  A  *  K  T  V  D  S   -

AGCAAGAGAAGGG
541 ------------+--- 553
    TCGTTCTCTTCCC a   S  K  R  R   -
```

Fig. 19

(SEQ ID NO. 21)

```
      GAAGCAAAAAACGAGCCCTGGAAGAAGAAAAACCACGCCGGGAAATCCTGGAAAAACGAT
    1 ---------+---------+---------+---------+---------+---------+ 60
      CTTCGTTTTTTGCTCGGGACCTTCTTCTTTTTGGTGCGGCCCTTTAGGACCTTTTTGCTA a     E  A  K  N  E  P  W  K  K  K  N  H  A  G  K  S  W  K  N  D  -

TACAGGAAGAAACTAGCCAGAGGAGAAGTTAATAGAAAAGGAAGTAAAAATAAGGGAGAG
   61 ---------+---------+---------+---------+---------+---------+ 120
      ATGTCCTTCTTTGATCGGTCTCCTCTTCAATTATCTTTTCCTTCATTTTTATTCCCTCTC a     Y  R  K  K  L  A  R  G  E  V  N  R  K  G  S  K  N  K  G  E  -

AGAAAGGGCACAGGCTCGTCCTTTGACACGCTACCTGCCTGTCCGGAAGAAGACTTTGAT
  121 ---------+---------+---------+---------+---------+---------+ 180
      TGTTTCCCGTGTCCGAGCAGGAAACTGTGCGATGGACGGACAGGCCTTCTTCTGAAACTA a     T  K  G  T  G  S  S  F  D  T  L  P  A  C  P  E  E  D  F  D  -

TSGCGG
  181 ------ 186
      AACGCC a     L  R  -
```

Fig. 20

(SEQ ID NO. 22)

```
     AGGGTACgGGAAGCTGCTGAAAAGGCTAAGTCTGAACTCTCCTCATCTGTGCAGACTGAC
  1  ---------+---------+---------+---------+---------+---------+ 60
     TCCCATGcCCTTCGACGACTTTTCCGATTCAGACTTGAGAGGAGTAGACACGTCTGACTG a    R  V  R  E  A  A  E  K  A  K  S  E  L  S  S  S  V  Q  T  D  -

ATCAAT
 61  ------ 66
     TAGTTA a    I  N  -
```

Fig. 21

(SEQ ID NO. 23)

```
     CATTTGAATATGAAGTTGACCCGTGCTCAATTTGAAGGGATTGTCACTGATCTAATCAGA
  1  ------------+---------+---------+---------+---------+---------+  60
     GTAAACTTATACTTCAACTGGGCACGAGTTAAACTTCCCTAACAGTGACTAGATTAGTCT a    H  L  N  M  K  L  T  R  A  Q  F  E  G  I  V  T  D  L  I  R   -

AGGACTATCGCTCCATGCCAAAAAGCTATGCAAGATGCAGAAGTCAGCAAGAGTGACATA
 61  ------------+---------+---------+---------+---------+---------+  120
     TCCTGATAGCGAGGTACGGTTTTTCGATACGTTCTACGTCTTCAGTCGTTCTCACTGTAT a    R  T  I  A  P  C  Q  K  A  M  Q  D  A  E  V  S  K  S  D  I   -

GGAGAAGTGATTCTTGTGGGTGGCATGACTAGGATGCCCAAGGTTCAGCAGACTGTACAG
121  ------------+---------+---------+---------+---------+---------+  180
     CCTCTTCACTAAGAACACCCACCGTACTGATCCTACGGGTTCCAAGTCGTCTGACATGTC a    G  E  V  I  L  V  G  G  M  T  R  M  P  K  V  Q  Q  T  V  Q   -

GACTTTTTGGCA
181  ------------+---  192
     CTGAAAAACCGT a    D  F  L  A   -
```

Fig. 22

(SEQ ID NO. 24)

```
          GGGGGCAGTGGACGAGGCCGTGGCGACCTGAAGCAGGCGCTTCCCTGTGTGGCCGAGTCG
     1    ------------+---------+---------+---------+---------+---------+  60
          CCCCCGTCACCTGCTCCGGCACCGCTGGACTTCGTCCGCGAAGGGACACACCGGCTCAGC a         G  G  S  G  R  G  R  G  D  L  K  Q  A  L  P  C  V  A  E  S    -

CCAACGGTCCACGTGGAGGTGCATCAGCGCGGCAGCAGCACTGCAAAGAAAGAAGACATA
    61    ------------+---------+---------+---------+---------+---------+ 120
          GGTTGCCAGGTGCACCTCCACGTAGTCGCGCCGTCGTCGTGACGTTTCTTTCTTCTGTAT a         P  T  V  H  V  E  V  H  Q  R  G  S  S  T  A  K  K  E  D  I    -

AACCTGAGTGTTAGAAAGCTACTCAACAGACATAATATTGTGTTTGGCGATTACACATGG
   121    ------------+---------+---------+---------+---------+---------+ 180
          TTGGACTCACAATCTTTCGATGAGTTGTCTGTATTATAACACAAACCGCTAATGTGTACC a         N  L  S  V  R  K  L  L  N  R  H  N  I  V  F  G  D  Y  T  W    -

ACTGAGTTTGATGAACCTTTTTTGACCAGAAATGTGCAGTCTGTGTCTATTATTGACACA
   181    ------------+---------+---------+---------+---------+---------+ 240
          TGACTCAAACTACTTGGAAAAAACTGGTCTTTACACGTCAGACACAGATAATAACTGTGT a         T  E  F  D  E  P  F  L  T  R  N  V  Q  S  V  S  I  I  D  T    -

GAATTAAAGGTTAAAGACTCACAGCCCATCGATTTGAGTGCATGCACTGTTGCACTTCAC
   241    ------------+---------+---------+---------+---------+---------+ 300
          CTTAATTTCCAATTTCTGAGTGTCGGGTAGCTAAACTCACGTACGTGACAACGTGAAGTG a         E  L  K  V  K  D  S  Q  P  I  D  L  S  A  C  T  V  A  L  H    -

ATTTTCCAGCTGAATGAAGATGGCCCCAGCAGTGAAAATCTGGAGGAAGAGACAGAAAAC
   301    ------------+---------+---------+---------+---------+---------+ 360
          TAAAAGGTCGACTTACTTCTACCGGGGTCGTCACTTTTAGACCTCCTTCTCTGTCTTTTG a         I  F  Q  L  N  E  D  G  P  S  S  E  N  L  E  E  E  T  E  N    -

ATAATTGCAGCAAATCACTGGGTTCTACCTGCAGCTGAATTCCATGGGCTTTGGGACAGC
   361    ------------+---------+---------+---------+---------+---------+ 420
          TATTAACGTCGTTTAGTGACCCAAGATGGACGTCGACTTAAGGTACCCGAAACCCTGTCG a         I  I  A  A  N  H  W  V  L  P  A  A  E  F  H  G  L  W  D  S    -

TTGGTATACGATGTGGAAGTCAAATCCCATCTCCTCGATTATGTGATGACAACTTTACTG
   421    ------------+---------+---------+---------+---------+---------+ 480
          AACCATATGCTACACCTTCAGTTTAGGGTAGAGGAGCTAATACACTACTGTTGAAATGAC a         L  V  Y  D  V  E  V  K  S  H  L  L  D  Y  V  M  T  T  L  L    -

TTTTCAGACAAGAACGTCAACAGCAACCTCATCACCATAGAGGGGTTCCTCCAGGCCCTG
   481    ------------+---------+---------+---------+---------+---------+ 540
          AAAAGTCTGTTCTTGCAGTTGTCGTTGGAGTAGTGGTATCTCCCCAAGGAGGTCCGGGAC a         F  S  D  K  N  V  N  S  N  L  I  T  I  E  G  F  L  Q  A  L    -

TCTCTGGCAGTGGACAAGCAGTTTGAAGAGAGAAAGAAGCTT
   541    ------------+---------+---------+---------+--  582
          AGAGACCGTCACCTGTTCGTCAAACTTCTCTCTTTCTTCGAA a         S  L  A  V  D  K  Q  F  E  E  R  K  K  L    -
```

Fig. 23

(SEQ ID NO. 25)

```
       TTCACCACTGTGATGGACCTCCTCCTGGAGTATGAAGTCATCTGTATCTACTGGACCAAG
    1  ------------+---------+---------+---------+---------+---------+  60
       AAGTGGTGACACTACCTGGACGAGGACCTCATACTTCAGTAGACATAGATGACCTGGTTC a      F  T  T  V  M  D  L  L  E  Y  E  V  I  C  I  Y  W  T  K    -

TACTACACACTCCACAATGCAATCATTGAGGATTGTGTCAGAAAACAGCTCAAAAAAGAG
   61  ------------+---------+---------+---------+---------+---------+  120
       ATGATGTGTGAGGTGTTACGTTAGTAACTCCTAACACAGTCTTTTGTCGAGTTTTTTCTC a      Y  Y  T  L  H  N  A  I  I  E  D  C  V  R  K  Q  L  R  K  E  -

AGGCCCATCATCCTGGATCCGGCCGACCCCACCCTCAACGTGGCAGAAGGGTACAGATGG
  121  ------------+---------+---------+---------+---------+---------+  180
       TCCGGGTAGTAGGACCTAGGCCGGCTGGGGTGGGAGTTGCACCGTCTTCCCATGTCTACC a      R  P  I  I  L  D  P  A  D  P  T  L  N  V  A  E  G  Y  R  W  -

GACATCGTTGCTCAGAGGGCCTCCCAGTGCCTGAAACAGGACTGTTGCTATGACAACAGG
  181  ------------+---------+---------+---------+---------+---------+  240
       CTGTAGCAACGAGTCTCCCGGAGGGTCACGGACTTTGTCCTGACAACGATACTGTTGTCC a      D  I  V  A  Q  R  A  S  Q  C  L  K  Q  D  C  C  Y  D  N  R  -

GAGAAGGGGATCTCCAGCTGGAACGTGAAGAGGGCACGAGACATCCACTTGACAGTGGAG
  241  ------------+---------+---------+---------+---------+---------+  300
       CTCTTCCCCTAGAGGTCGACCTTGCACTTCTCCCGTGCTCTGTAGGTGAACTGTCACCTC a      Q  R  G  Y  P  D  F  N  L  I  V  N  P  Y  E  P  I  R  K  V  -

CAGAGGGGTTACCCAGATTTCAACCTCATCGTGAACCCTTATGAGCCCATAAGGAAGGTT
  301  ------------+---------+---------+---------+---------+---------+  360
       GTCTCCCCAATGGGTCTAAAGTTGGAGTAGCACTTGGGAATACTCGGGTATTCCTTCCAA a      Q  R  G  Y  P  D  F  N  L  I  V  N  P  Y  E  P  I  R  K  V  -

AAAGACAAAATCCGGAGACCAGGGGCTACTCTGGCCTGCAGCGTCTGTCCTTCCAGGTTC
  361  ------------+---------+---------+---------+---------+---------+  420
       TTTCTCTTTTAGGCCTCTGGTCCCCGATGAGACCGGACGTCGCAGACAGGAAGGTCCAAG a      K  E  I  I  R  R  P  G  A  T  L  A  C  S  V  C  P  S  R  F  -

CTGGCAGTGAGAGGCAGCTTCTCAGCAGCAGGTGCTCCTTAGCCAAATATGGGATCTTCT
  421  ------------+---------+---------+---------+---------+---------+  480
       GACCGTCACTCTCCGTCGAAGAGTCGTCGTCCACGAGGAATCGGTTTATACCCTAGAAGA a      L  A  V  R  G  S  F  S  A  A  G  A  P  *  P  N  M  G  S  S  -

CCCACAC
  481  ------- 487
       GGGTGTG a      P  T  -
```

Fig. 24

(SEQ ID NO. 26)

```
    ATGGAGGATGATTTCATGTGCGATGATGAGGAGGACTACGACCTGGAATACTCTGAAGAT
  1 ---------+---------+---------+---------+---------+---------+ 60
    TACCTCCTACTAAAGTACACGCTACTACTCCTCCTGATGCTGGACCTTATGAGACTTCTA a   M  E  D  D  F  M  C  D  D  E  E  D  Y  D  L  E  Y  S  E  D   -

AGTAACTCCGAGCCAAATGTGGATTTGGAAAATCAGTACTATAATTCCAAAGCATTAAAA
 61 ---------+---------+---------+---------+---------+---------+ 120
    TCATTGAGGCTCGGTTTACACCTAAACCTTTTAGTCATGATATTAAGGTTTCGTAATTTT a   S  N  S  E  P  N  V  D  L  E  N  Q  Y  Y  N  S  K  A  L  K   -

GAAGATGACCCAAAAGCGGCATTAAGCAGTTTCCAAAAGGTTTTGGAACTTGAAGGTGAA
121 ---------+---------+---------+---------+---------+---------+ 180
    CTTCTACTGGGTTTTCGCCGTAATTCGTCAAAGGTTTTCCAAAACCTTGAACTTCCACTT a   E  D  D  P  K  A  A  L  S  S  F  Q  K  V  L  E  L  E  G  E   -

AAAGGAGAATGGGGATTTAAAGCACTGAAACAAATGATTAAGATTAACTTCAAGTTGACA
181 ---------+---------+---------+---------+---------+---------+ 240
    TTTCCTCTTACCCCTAAATTTCGTGACTTTGTTTACTAATTCTAATTGAAGTTCAACTGT a   K  G  E  W  G  F  K  A  L  K  Q  M  I  K  I  N  F  K  L  T   -

AACTTTCCAGAAATGATGAATAGATATAAGCAGCTATTGACCTATATTCGGAGTGCAGTC
241 ---------+---------+---------+---------+---------+---------+ 300
    TTGAAAGGTCTTTACTACTTATCTATATTCGTCGATAACTGGATATAAGCCTCACGTCAG a   N  F  P  E  M  M  N  R  Y  K  Q  L  L  T  Y  I  R  S  A  V   -

ACAAGAAATTATTCTGAAAAATCCATTAATTCTATTCTTGATTATATCTCTACTTCTAAA
301 ---------+---------+---------+---------+---------+---------+ 360
    TGTTCTTTAATAAGACTTTTTAGGTAATTAAGATAAGAACTAATATAGAGATGAAGATTT a   T  R  N  Y  S  E  K  S  I  N  S  I  L  D  Y  I  S  T  S  K   -

CAGATGGATTTACTGCAGGAATTCTATGAAACAACACTGGAAGCTTTGAAAGATGCTAAG
361 ---------+---------+---------+---------+---------+---------+ 420
    GSCSACCSAAATGACG?CCSSAAGASACSSSGSSGTGACCrTCGAAACSSSCTAC5ASTC a   Q  M  D  L  L  Q  E  F  Y  E  T  T  L  E  A  L  K  D  A  K   -

AATGATAGACTGTGGTTTAAGACAAACACAAAGCTTGGAAAATTATATTTAGAACGAGAG
421 ---------+---------+---------+---------+---------+---------+ 480
    TTACTATCTGACACCAAATTCTGTTTGTGTTTCGAACCTTTTAATATAAATCTTGCTCTC a   N  D  R  L  W  F  K  T  N  T  K  L  G  K  L  Y  L  E  R  E   -

GAATATGGAAAGCTTCAAAAAATTTTACGCCAGTTACATCAGTCGTGCCAGACTGATGAT
481 ---------+---------+---------+---------+---------+---------+ 540
    CTTATACCTTTCGAAGTTTTTTAAAATGCGGTCAATGTAGTCAGCACGGTCTGACTACTA a   E  Y  G  K  L  Q  K  I  L  R  Q  L  H  Q  S  C  Q  T  D  D   -

GGAGAAGATGATCTGAAAAAAGGTACACAGTTATTAGAAATATATGCTTTGGAAATTCAA
541 ---------+---------+---------+---------+---------+---------+ 600
    CCTCTTCTACTAGACTTTTTTCCATGTGTCAATAATCTTTATATACGAAACCTTTAAGTT
```

Fig. 25A

```
a       G  E  D  D  L  K  K  G  T  Q  L  L  E  I  Y  A  L  E  I  Q   -
        ATGTACACAGCACAGAAAAATAACAAAAAACTTAAAGCACTCTATGAACAGTCACTTCAC
    601 ---------+---------+---------+---------+---------+---------+ 660
        TACATGTGTCGTGTCTTTTTATTGTTTTTTGAATTTCGTGAGATACTTGTCAGTGAAGTG a       M  Y  T  A  Q  K  N  N  K  K  L  K  A  L  Y  E  Q  S  L  H   -
        ATCAAGTCTGCCATCCCTCATCCACTGATTATGGGAGTTATCAGAGAATGTGGTGGTAAA
    661 ---------+---------+---------+---------+---------+---------+ 720
        TAGTTCAGACGGTAGGGAGTAGGTGACTAATACCCTCAATAGTCTCTTACACCACCATTT a       I  K  S  A  I  P  H  P  L  I  M  G  V  I  R  E  C  G  G  K   -
        ATTGCACTTGGGGGAGGTGAATTTGAAAAGGCACACACTGATTTTTTT
    721 ---------+---------+---------+---------+-------- 768
        TAACGTGAACCCCCTCCACTTAAACTTTTCCGTGTGTGACTAAAAAAA a       I  A  L  G  G  G  E  F  E  K  A  H  T  D  F  F   -
```

Fig. 25B (SEQ ID NO. 27)

```
       GCAGAGGTTAAAACACCTTTTGATTTGGCCAAGGCACAAGAGAACAGCAACTCCGTAAAG
    1  ------------+---------+---------+---------+---------+---------+  60
       CGTCTCCAATTTTGTGGAAAACTAAACCGGTTCCGTGTTCTCTTGTCGTTGAGGCATTTC a      A  E  V  K  T  P  F  D  L  A  K  A  Q  E  N  S  N  S  V  K   -

AAGAAGACAAAGTTTGTCAATTTATACACAAGAGAAAGACAGGACAGGCTTGCAGTCCTG
   61  ------------+---------+---------+---------+---------+---------+ 120
       TTCTTCTGTTTCAAACAGTTAAATATGTGTTCTCTTTCTGTCCTGTCCGAACGTCAGGAC a      K  K  T  K  F  V  N  L  Y  T  R  E  R  Q  D  R  L  A  V  L   -

CTCCCTGGTCGTCACCCTTGTGATTGCCTGGGCCAGAAGCACAAGCTCATCAATAACTGT
  121  ------------+---------+---------+---------+---------+---------+ 180
       GAGGGACCAGCAGTGGGAACACTAACGGACCCGGTCTTCGTCTTCGAGTAGTTATTGACA a      L  P  G  R  H  P  C  D  C  L  G  Q  K  H  K  L  I  N  N  C   -

CTGATCTGTGGGCGCATTGTCTGTGAACAAGAAGGCTCAGGCCCTTGCTTATTCTGTGGC
  181  ------------+---------+---------+---------+---------+---------+ 240
       GACTAGACACCCGCGTAACAGACACTTGTTCTTCCGAGTCCGGGAACGAATAAGACACCG a      L  I  C  G  R  I  V  C  E  Q  E  G  S  G  P  C  L  F  C  G   -

ACTCTGGTGTGTACTCATGAGGAACAAGATATTTTACAGCGTGACTCAAACAAGAGCCAG
  241  ------------+---------+---------+---------+---------+---------+ 300
       TGAGACCACACATGAGTACSCCSSGSSCSATAkAASGSCGCACTSAGSSSGTTCTCGGSC a      T  L  V  C  T  H  E  E  Q  D  I  L  Q  R  D  S  N  K  S  Q   -

AAACTGCTAAAGAAACTCATGTCAGGAGTGGAGAATTCTGGAAAGGTGGACATCTCTACC
  301  ------------+---------+---------+---------+---------+---------+ 360
       TTTGACGATTTCTTTGAGTACAGTCCTCACCTCTTAAGACCTTTCCACCTGTAGAGATGG a      K  L  L  K  K  L  M  S  G  V  E  N  S  G  K  V  D  I  S  T   -

AAGGACCTTCTTCCTCATCAAGAATTGCGAATTAAGTCTGGTCTGGAGAAGGCTATCAAG
  361  ------------+---------+---------+---------+---------+---------+ 420
       TTCCTGGAAGAAGGAGTAGTTCTTAACGCTTAATTCAGACCAGACCTCTTCCGATAGTTC a      K  D  L  L  P  H  Q  E  L  R  I  K  S  G  L  E  K  A  I  K   -

CATAAAGACAAACTGTTAGAGTTTGACAGAACTAGTATTCGAAGGACCCAAGTCATTGAT
  421  ------------+---------+---------+---------+---------+---------+ 480
       GTATTTCTGTTTGACAATCTCAAACTGTCTTGATCATAAGCTTCCTGGGTTCAGTAACTA a      H  K  D  K  L  L  E  F  D  R  T  S  I  R  R  T  Q  V  I  D   -

GATGAGTCAGATTACTTTGCCAGTGATTCTAACCAATGGTTGTCCAAACTTGAGCGGGAA
  481  ------------+---------+---------+---------+---------+---------+ 540
       CTACTCAGTCTAATGAAACGGTCACTAAGATTGGTTACCAACAGGTTTGAACTCGCCCTT a      D  E  S  D  Y  F  A  S  D  S  N  Q  W  L  S  K  L  E  R  E   -

ACCTTGCAGAAGCGAGAGGAGGAGCTGAGAGAACTTCGACACGCCTCTCGACTTTCTAAG
  541  ------------+---------+---------+---------+---------+---------+ 600
       TGGAACGTCTTCGCTCTCCTCCTCGACTCTCTTGAAGCTGTGCGGAGAGCTGAAAGATTC
```

Fig. 26A

```
a     T  L  Q  K  R  E  E  E  L  R  E  L  R  H  A  S  R  L  S  K   -
      AAGGTCACCATTGACTTTGCAGGAAGGAAGATCCTGGAAGAAGAAAATTCACTAGCAGAG
601   ------------+---------+---------+---------+---------+---------+   660
      TTCCAGTGGTAACTGAAACGTCCTTCCTTCTAGGACCTTCTTCTTTTAAGTGATCGTCTC a     K  V  T  I  D  F  A  G  R  K  I  L  E  E  E  N  S  L  A  E   -
      TATCATAGCAGACTAGATGAGACAATACAGGCCATTGCCAATGGAACCTTGAACCAGCCA
661   ------------+---------+---------+---------+---------+---------+   720
      ATAGTATCGTCTGATCTACTCTGTTATGTCCGGTAACGGTTACCTTGGAACTTGGTCGGT a     Y  H  S  R  L  D  E  T  I  Q  A  I  A  N  G  T  L  N  Q  P   -
      CTGACCAAATTGGATAGATCTTCTGAAGAGCCTTTGGGAGTTCTGGTAAATCCCAACATG
721   ------------+---------+---------+---------+---------+---------+   780
      GACTGGTTTAACCTATCTAGAAGACTTCTCGGAAACCCTCAAGACCATTTAGGGTTGTAC a     L  T  K  L  D  R  S  S  E  E  P  L  G  V  L  V  N  P  N  M   -
      TACCAGTCCCCTCCCCAGTGGTTGACCACACAGGTGCAGCCTCACAGAAGAAGGCTTTCC
781   ------------+---------+---------+---------+---------+---------+   840
      ATGGTCAGGGGAGGGGTCACCAACTGGTGTGTCCACGTCGGAGTGTCTTCTTCCGAAAGG a     Y  Q  S  P  P  Q  W  L  T  T  Q  V  Q  P  H  R  R  R  L  S   -
      GTTCTTCAGGATTTGGACTAGAGTTCAACTCATTTCAGCACCAGTTGCGAATCCAGGATC
841   ------------+---------+---------+---------+---------+---------+   900
      CAAGAAGTCCTAAACCTGATCTCAAGTTGAGTAAAGTCGTGGTCAACGCTTAGGTCCTAG a     V  L  Q  D  L  D  *  S  S  T  H  F  S  T  C  E  S  R  I      -
      AAGAATTTCAGGAAGGCTTTGATGGTGGCTGGTGCCTCTCTGTACATCAGCCCTGGGTTC
901   ------------+---------+---------+---------+---------+---------+   960
      TTCTTAAAGTCCTTCCGAAACTACCACCGACCACGGAGAGACATGTAGTCGGGACCCAAG a     K  N  F  R  K  A  L  M  V  A  G  A  S  L  Y  I  S  P  G  F   -
      TCTGCTTGTCAGAGGGATTAAAAGGGTGGAGGGCAGATCCTGGTACACCCCCCACAGAGG
961   ------------+---------+---------+---------+---------+---------+   1020
      AGACGAACAGTCTCCCTAATTTTCCCACCTCCCGTCTAGGACCATGTGGGGGGTGTCTCC a     S  A  C  Q  R  D  *  K  G  G  G  Q  I  L  V  H  P  P  Q  R   -
      ACGACTTTGGATAGCAGCCACAGCTAAAAAATCCCTCCCCTCAAGAAGTCTCAGAACTCC
1021  ------------+---------+---------+---------+---------+---------+   1080
      TGCTGAAACCTATCGTCGGTGTCGATTTTTTAGGGAGGGGAGTTCTTCAGAGTCTTGAGG a     T  T  L  D  S  S  H  S  *  K  I  P  P  L  K  K  S  Q  N  S   -
      AGGCTACATATCGTCTTCTTCGTTGGGAAGATGTGGAATTT
1081  ------------+---------+---------+---------+-   1121
      TCCGATGTATAGCAGAAGAAGCAACCCTTCTACACCTTAAA a     R  L  H  I  V  F  F  V  G  K  M  W  N        -
```

Fig. 26B (SEQ ID NO. 28)

```
     GAAAGGGCCCTGACAGCACACACACTTAAACACAGTTTTCTGATAACTTTGGAATTCACA
  1  ------------+---------+---------+---------+---------+---------+ 60
     CTTTCCCGGGACTGTCGTGTGTGTGAATTTGTGTCAAAAGACTATTGAAACCTTAAGTGT a    E  R  A  L  T  A  H  T  L  K  H  S  F  L  I  T  L  E  F  T   -

CCGTTGGACTAGTTAAAAACTTCTAAAATAATTTTTTAAAATCTAATA
  61 ------------+---------+---------+---------+-------- 108
     GGCAACCTGATCAATTTTTGAAGATTTTATTAAAAAATTTTAGATTAT a    P  L  D  *  L  K  T  S  K  I  I  F  *  N  L  I   -
```

Fig. 27

(SEQ ID NO. 29)

```
     CCAGGAACTGAGATCTTTAATCTGCCAGCAGTTACTACGTCAGGCTCAGTTAGCTCTAGA
   1 ------------+---------+---------+---------+---------+---------+ 60
     GGTCCTTGACTCTAGAAATTAGACGGTCGTCAATGATGCAGTCCGAGTCAATCGAGATCT a    P  G  T  E  I  F  N  L  P  A  V  T  T  S  G  S  V  S  S  R   -

GGCCATTCTTTTGCTGATCCTGCCAGTAATCTTGGGCTGGAAGACATTATCAGGAAGGCT
  61 ------------+---------+---------+---------+---------+---------+ 120
     CCGGTAAGAAAACGACTAGGACGGTCATTAGAACCCGACCTTCTGTAATAGTCCTTCCGA a    G  H  S  F  A  D  P  A  S  N  L  G  L  E  D  I  I  R  K  A   -

CTCATGGGAAGCTTTGATGACAAAGTTGAGGATCATGGAGTTGTCATGTCCCAGCCTATG
 121 ------------+---------+---------+---------+---------+---------+ 180
     GAGTACCCTTCGAAACTACTGTTTCAACTCCTAGTACCTCAACAGTACAGGGTCGGATAC a    L  M  G  S  F  D  D  K  V  E  D  H  G  V  V  M  S  Q  P  M   -

GGAGTAGTGCCTGGTACTGCCAACACCTCAGTTGTGACC
 181 ------------+---------+---------+--------- 219
     CCTCATCACGGACCATGACGGTTGTGGAGTCAACACTGG a    G  V  V  P  G  T  A  N  T  S  V  V  T   -
```

Fig. 28

(SEQ ID NO. 30)

```
351a   26 LQLEAENYEGHTPLHVAVIHKDVEMVRLLRDAGADLDKPEPTCGRSPFIW 75
          | ||| || | | ||||| | | || ||| |    |||| |
BCL3  225 LDLEARNYDGLTALHVAVNTECQETVQLLLERGADIDVDIKSGRSPLIH 274

351a   76 QWRPGS.RCAGASLRAGANPAARMYGGRTPLGSAMLRPNPILARLLR 121
          |       |  ||| |||| |||  ||| |            ||
BCL3  275 AVENNSLSMVQLLLQHGANVNAQMSGSSALHSASGRGLLPLVRTLV 321

351a  122 AHGAPEPEGKDEKSGP 137
              ||        |
BCL3  322 RSGADSSLKNCHNDTP 337
```

Fig. 30

NUCLEAR HORMONE RECEPTOR-INTERACTING POLYPEPTIDES AND RELATED MOLECULES AND METHODS

This application is a continuation-in-part of U.S. Ser. No. 07/969,136, filed Oct. 30, 1992, now abandoned.

This invention was made with Government support under Contract #R1-DK43382 awarded by the National Institutes of Health. The Government has certain rights in this invention.

BACKGROUND OF THE INVENTION

This invention relates to receptor proteins.

The diverse physiological and developmental effects of thyroid hormone receptor (for example, T3) are mediated by the three hormone-binding isoforms of the T3 receptor: TRα1, TRβ1, and TRβ2. The effects of the hormone are the consequences of changes in expression of a wide range of target genes that result from T3 binding to these receptors. While it is unknown how binding of the ligand to the receptor actually causes such changes in gene expression, the basic effects on the rate of transcription are believed to be a consequence of direct or indirect protein-protein contacts between the TRs and components of basic transcriptional apparatus, such as RNA polymerase or associated proteins. In addition, interactions of TRs with other transcription factors are thought to result in a variety of complex combinatorial regulatory effects.

In recent years there has been very rapid progress in unravelling the most basic aspects of the mechanism of T3 action in the control of gene expression (see Brent et al., Ann. Rev. Physiol. 53:17–35, 1991 for recent review). It is now clear that the T3 receptors are transcription factors that belong to a related superfamily of nuclear hormone receptors. This family of proteins interacts not only with diverse ligands but also with a complex array of similar DNA binding sites. Like other DNA binding transcription factors, the TRs function by increasing (or, in some cases, decreasing) the rate of transcription initiation from a linked promoter.

Other details of the mechanisms that cause such alterations remain unclear and are the focus of intense study in a number of systems (see Lewin, Cell 61:1161–1164, 1990; Ptashne, Sci. Am. 260:40–47, 1989; Ptashne, and Gann, Nature 346:329–331, 1990, for reviews). However, two broad themes are evident. The first is that transcription factors in general are frequently modular, composed of distinct domains with separate DNA binding and transcriptional regulatory functions. With TRs, for example, it is apparent that the DNA binding and ligand binding domains are quite separate, and experiments with chimeric receptors make it clear that the T3 dependent activation of gene expression can be transferred to heterologous DNA binding domains (see, e.g., Holloway, Proc. Natl. Acad. Sci. U.S.A. 87:8160–8164, 1990; Thompson and Evans, Proc. Natl. Acad. Sci. U.S.A. 86:3494–3498, 1989).

A second theme is that the functions of transcription factors are believed to be a consequence of protein-protein interactions with the basic transcriptional apparatus. It is thought that these interactions are mediated by proteins called coactivators or adaptors (see Ptashne and Gann, Nature 346:329–331, 1990). These poorly characterized proteins act as bridges between the transcriptional activation domain that is tethered to the DNA by the transcription factor and the RNA polymerase complex bound at the initiation site. Via unknown mechanisms, this interaction leads to an increase in promoter activity.

Protein-protein contacts are also essential for a surprisingly diverse array of positive and negative interactions between transcription factors. Recent results in several systems indicate that this mechanism leads to complex regulatory networks that allow cross talk between various signalling pathways. In the case of TRs, three such interactions have been described to date. The first is the heterodimeric interaction of TRs with the related RXRs (Bugge et al., EMBO J 11:1409–1418, 1992; Kliewer et al., Nature 355:446–449, 1992; Lied et al., Cell 68:377–395, 1992; Marks et al., EMBO J 11:1419–1435, 1992; Yu et al., Cell 67:1251–1266, 1991; Zhang et al., Nature 355:441–446, 1992). TR/RXR heterodimers show higher DNA binding affinity to thyroid hormone response elements (i.e., T3RE sites) initially characterized as binding TR homodimers (see, e.g., Williams et al., J. Biol. Chem. 266:19636–19644, 1991), but heterodimerization does not appear to alter site specificity.

A second, less direct interaction is reflected in the mutually antagonistic effects of the TRs and the c-jun and c-fos protooncogenes (Desbois et al., Cell 67:731–740, 1991; Zhang et al., Mol. Cell. Biol. 11:6016–6025, 1991). The heterodimeric complex of these two leucine zipper transcription factors is frequently referred to as AP-1, although the jun-jun homodimers and other complexes containing related but less well characterized proteins can also bind the consensus AP-1 site. Such sites are also referred to as TPA response elements (i.e., TREs) (here distinguished from T3REs) because the induction of protein kinase C activity by TPA or other phorbol esters results in a very rapid induction of AP-1 activity (reviewed in (Curran and Franza, Cell 55:395–397, 1988). The activity of the TRs is antagonized by coexpression of active jun or fos, and the TRs exert a complimentary inhibition of jun and fos activity. Although the mechanism of this interaction is unknown, it does not require the presence of overlapping DNA binding sites. Thus, TRs can antagonize TPA response on a promoter that does not contain a T3RE, and jun and fos can antagonize T3 response on a promoter that does not include a TRE. Interestingly, although TRs are always nuclear and are able to bind T3REs whether or not hormone is present, the antagonistic function is only observed when T3 is present.

The antagonistic interaction with jun and fos is also observed with other members of the superfamily, including RARs (Desbois et al., Cell 67:731–740, 1991; Schule et al., Proc. Natl. Acad. Sci. U.S.A. 88:6092–6096, 1991) and GRs (Jonat et al., Cell 62:1189–1204; Schule et al., Cell 62:1217–1226, 1990; Yang-Yen et al., Cell 62:1205–1215, 1990). The GR interaction was the first described and has been the best characterized, but the biochemical basis for the effect remains uncertain (see Ponta et al., Acta 1129:255–261, 1992 for a review). Despite the potential importance of this apparent cross-talk between nuclear hormone receptors and the protein kinase C signalling pathway, its physiologic impact also remains unclear.

Finally, TRs have also been reported to interact both functionally and biochemically with the cell-type specific transcriptional activator Pit1 (Schaufele et al., Mol. Endocrinol. 6:656–665, 1992). In contrast to the antagonistic effects of TRs and AP-1, this interaction apparently leads to synergistic activation.

These distinct mechanisms for the modulation of transcriptional activation remain quite unclear. It is apparent that the identification and characterization of proteins capable of interacting specifically with the TRs could provide important clues to these processes and other potential functions of the receptors, such as regulation of cell proliferation (Halperin et al., Endocrinology 126:2321–2326, 1990). In addition, interacting proteins provide a means of controlling and modulating thyroid hormone receptor function.

SUMMARY OF THE INVENTION

In a first aspect, the invention generally features a method for determining whether a test protein is capable of interacting with a nuclear hormone receptor protein. The method involves: (a) providing a host cell which contains (i) a reporter gene operably linked to a protein binding site; (ii) a first fusion gene which expresses a first fusion protein, the first fusion protein including a nuclear hormone receptor protein covalently bonded to a binding moiety which is capable of specifically binding to the protein binding site; and (iii) a second fusion gene which expresses a second fusion protein, the second fusion protein including the test protein covalently bonded to a weak gene activating moiety; and (b) determining whether the test protein increases expression of the reporter gene as an indication of its ability to interact with the nuclear hormone receptor protein.

In a preferred embodiment, the method further involves treating the host cell with a ligand which binds the nuclear hormone receptor and identifying a hormone-dependent interacting protein by its ability to increase expression of the reporter gene only upon treatment of the cell by the ligand. In another preferred embodiment, the method further involves treating the host cell with a ligand which binds the nuclear hormone receptor and identifying a hormone-independent interacting protein by its ability to increase expression of the reporter gene both in the presence and in the absence of ligand treatment. In yet another preferred embodiment, the method further involves treating the host cell with a ligand which binds the nuclear hormone receptor and identifying a ligand-sensitive interacting protein by its ability to increase expression of the reporter gene in the absence but not in the presence of the ligand treatment. Preferably, the ligand is a thyroid hormone.

In other preferred embodiments, the weak gene activating moiety is the gene activating moiety of B42 or a gene activating moiety of lesser activation potential; and the nuclear hormone receptor is a thyroid hormone receptor.

In a second aspect, the invention features a substantially pure preparation of a thyroid hormone receptor (TR)-interacting protein. Preferably, the TR-interacting protein is JL-1 or JL-2; includes an amino acid sequence substantially identical to an amino acid sequence shown in any of FIGS. 2–28 (SEQ ID NOS: 1, 3, 6–30); and is derived from a mammal, for example, a human.

In a related aspect, the invention features purified DNA (for example, cDNA) which includes a sequence encoding a TR-interacting protein, preferably encoding a human TR-interacting protein, for example, the TR-interacting proteins JL-1 or JL-2.

In other related aspects, the invention features a vector and a cell which includes a purified DNA of the invention; a purified antibody which specifically binds a TR-interacting protein of the invention; and a method of producing a recombinant TR-interacting protein involving providing a cell transformed with DNA encoding a TR-interacting protein positioned for expression in the cell; culturing the transformed cell under conditions for expressing the DNA; and isolating the recombinant TR-interacting protein. The invention further features recombinant TR-interacting protein produced by such expression of a purified DNA of the invention.

In yet another aspect, the invention features a therapeutic composition which includes as an active ingredient a TR-interacting protein of the invention, the active ingredient being formulated in a physiologically-acceptable carrier. Such therapeutic compositions are useful in a method of treating thyroid disorders in a mammal, involving administering the therapeutic composition to the mammal in a dosage effective to increase thyroid function (in the case of hypothyroidism) or decrease thyroid function (in the case of hyperthyroidism).

As used herein, "reporter gene" is meant a gene whose expression may be assayed; such genes include, without limitation, lacZ, amino acid biosynthetic genes, e.g. the yeast LEU2 gene, or the mammalian chloramphenicol transacetylase (CAT) gene. Reporter genes may be integrated into the chromosome or may be carried on autonomously replicating plasmids (e.g., yeast $2\mu$ plasmids).

By "operably linked" is meant that a gene and a regulatory sequence(s) are connected in such a way as to permit gene expression when the appropriate molecules (e.g., transcriptional activator proteins or proteins which include transcriptional activation domains) are bound to the regulatory sequence(s).

By a "binding moiety" is meant a stretch of amino acids which is capable of directing specific polypeptide binding to a particular DNA sequence (i.e., a "protein binding site"). LexA represents a preferred DNA binding moiety in the invention. However, any other transcriptionally-inert or essentially transcriptionally-inert DNA binding domain may be substituted. The GAL4 DNA binding domain represents a somewhat less preferred DNA binding moiety for the system described herein.

By "weak gene activating moiety" is meant a stretch of amino acids which is capable of weakly inducing the expression of a gene to whose control region it is bound. As used herein, "weakly" is meant below the level of activation effected by GAL4 activation region II (Ma and Ptashne, Cell 48:847, 1987) and is preferably at or below the level of activation effected by the B42 activation domain of Ma and Ptashne (Cell 51:113, 1987). Levels of activation may be measured using any downstream reporter gene system and comparing, in parallel assays, the level of expression stimulated by the GAL4- or B42-polypeptide with the level of expression stimulated by the polypeptide to be tested.

By "TR-interacting protein" is meant a polypeptide which directly or indirectly physically interacts with a thyroid hormone receptor in the in vivo protein interaction assay described herein. Such an interaction may be thyroid hormone dependent or independent or may be thyroid hormone sensitive; it may also be transient in nature. Preferably, such a polypeptide has an amino acid sequence which is at least 80%, preferably 90%, and most preferably 95% or even 99% homologous to the amino acid sequence of an interacting protein described herein (e.g., JL-1 or JL-2) at the point of interaction with the thyroid hormone receptor, or at least 80% and preferably 90% homologous overall. A "TR-interacting protein", as used herein, does not include any of the RXR proteins or Pit-1.

By "thyroid hormone" is meant T3, triac, or T4, and less preferably reverse T3.

By "substantially pure" is meant a preparation which is at least 60% by weight (dry weight) the compound of interest, i.e., a TR-interacting protein. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "purified DNA" is meant DNA that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). Preferably, such a sequence is at least 80%, more preferably 90%, and most preferably 95% homologous to one of the sequences of FIGS. 2–28 (SEQ ID NOS: 1, 3, 6–30). A "substantially identical" nucleic acid sequence codes for a substantially identical amino acid sequence as defined above.

By "transformed cell" is meant a cell into which (or into an ancestor of which) has been introduced, by means of recombinant DNA techniques, a DNA molecule encoding (as used herein) a TR-interacting protein.

By "positioned for expression" is meant that the DNA molecule is positioned adjacent to a DNA sequence which directs transcription and translation of the sequence (i.e., facilitates the production of, e.g., a TR-interacting protein).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody, e.g., TR-interacting protein-specific antibody. A purified TR-interacting protein antibody may be obtained, for example, by affinity chromatography using recombinantly-produced TR-interacting protein and standard techniques.

By "specifically binds" is meant an antibody which recognizes and binds TR-interacting protein but which does not substantially recognize and bind other molecules in a sample, e.g., a biological sample, which naturally includes TR-interacting protein.

Other features and advantages of the invention will be apparent from the following detailed description thereof, and from the claims.

BRIEF DESCRIPTION OF THE DRAWINGS

The drawings are first briefly described.

FIG. 2 shows the complete amino acid sequence of JL1 (SEQ ID NO:1), aligned with the recently identified *S. cerevisiae* transcriptional coactivator SUG1 (Swaffield et al., Nature 357:698–700, 1992) (SEQ ID NO:2). Identities and conservative substitutions are indicated. The overall sequence identity is 73%. The boxed and bold residues from 190 to 197 (JL1) represent a potential ATP binding site that is conserved in all members of this family. The boxed residues from 45 to 66 (JL1) are a putative leucine zipper, extended by 1 heptad toward the N-terminus in this full length sequence, which appears to be unique to JL1 and SUG1. The N-terminal portion of the JL1 sequence (1–49) was derived from subcloned PCR products corresponding to the 5' end of the JL1 mRNA. Independent clones with identical sequence were isolated using internal JL1 and vector primers with a HeLa cell cDNA library as template. The methionine residue assigned as the start codon is preceded by a stop codon only 9 nucleotides upstream.

FIGS. 3A and 3B show (A) the amino acid sequence of JL2 (SEQ ID NO:3); the two LIM domains are underlined and the consensus C/D and H residues are bold. This sequence represents the human portion of the fusion protein isolated as an activator of the lexA/TRβ chimera. (B) shows the alignment of the LIM domains of JL2 (SEQ ID NO:4) with those of Lin11 (SEQ ID NO:5). These domains in both proteins include matches to all consensus positions; the overall sequence identity is 35%.

FIG. 4 (SEQ ID NO:6) shows a partial nucleic acid sequence and deduced amino acid sequence of the TR-interacting protein S112a-.

FIG. 5 (SEQ ID NO:7) shows a partial nucleic acid sequence and deduced amino acid sequence of the TR-interacting protein S103a.

FIG. 6 (SEQ ID NO:8) shows a partial nucleic acid sequence and deduced amino acid sequence of the TR-interacting protein S203a.

FIG. 7 (SEQ ID NO:9) shows a partial nucleic acid sequence and deduced amino acid sequence of the TR-interacting protein S204b.

FIG. 8 (SEQ ID NO:10) shows a partial nucleic acid sequence and deduced amino acid sequence of the TR-interacting protein S205a.

FIG. 9 (SEQ ID NO:11) shows a partial nucleic acid sequence and deduced amino acid sequence of the TR-interacting protein S249a.

FIG. 10 (SEQ ID NO:12) shows a partial nucleic acid sequence and deduced amino acid sequence of the TR-interacting protein S351a.

FIG. 11 (SEQ ID NO:13) shows a partial nucleic acid sequence and deduced amino acid sequence of the TR-interacting protein S101a.

FIG. 12 (SEQ ID NO:14) shows a partial nucleic acid sequence and deduced amino acid sequence of the TR-interacting protein S223a.

FIG. 13 (SEQ ID NO:15) shows a partial nucleic acid sequence and deduced amino acid sequence of the TR-interacting protein S239a.

FIG. 14 (SEQ ID NO:16) shows a partial nucleic acid sequence and deduced amino acid sequence of the TR-interacting protein S410a.

FIG. 15 (SEQ ID NO:17) shows a partial nucleic acid sequence and deduced amino acid sequence of the TR-interacting protein S418a.

FIG. 16 (SEQ ID NO:18) shows a partial nucleic acid sequence and deduced amino acid sequence of the TR-interacting protein S419a.

FIG. 17 (SEQ ID NO:19) shows a partial nucleic acid sequence and deduced amino acid sequence of the TR-interacting protein S107a-.

FIG. 18 (SEQ ID NO:20) shows a partial nucleic acid sequence and deduced amino acid sequence of the TR-interacting protein S213a-.

FIG. 19 (SEQ ID NO:21) shows a partial nucleic acid sequence and deduced amino acid sequence of the TR-interacting protein S113a-.

FIG. 20 (SEQ ID NO:22) shows a partial nucleic acid sequence and deduced amino acid sequence of the TR-interacting protein S116a-.

FIG. 21 (SEQ ID NO:23) shows a partial nucleic acid sequence and deduced amino acid sequence of the TR-interacting protein S309a-.

FIG. 22 (SEQ ID NO:24) shows a partial nucleic acid sequence and deduced amino acid sequence of the TR-interacting protein S227b-.

FIG. 23 (SEQ ID NO:25) shows a partial nucleic acid sequence and deduced amino acid sequence of the TR-interacting protein S215a-.

FIG. 24 (SEQ ID NO:26) shows a partial nucleic acid sequence and deduced amino acid sequence of the TR-interacting protein S223a-.

FIG. 25 (SEQ ID NO:27) shows a partial nucleic acid sequence and deduced amino acid sequence of the TR-interacting protein S240a-.

FIG. 26 (SEQ ID NO:28) shows a partial nucleic acid sequence and deduced amino acid sequence of the TR-interacting protein S139a.

FIG. 27 (SEQ ID NO:29) shows a partial nucleic acid sequence and deduced amino acid sequence of the TR-interacting protein S110a-.

FIG. 28 (SEQ ID NO:30) shows a partial nucleic acid sequence and deduced amino acid sequence of the TR-interacting protein S243b.

FIG. 30 shows the amino acid comparison of polypeptide 351a (SEQ ID NO: 12 from positions 78–411) and a portion of BCL3. (SEQ ID NO: 31) Identical amino acids are indicated, and approximate positions of ankyrin repeats are underlined in BCL3. The first ankyrin repeat of BCL3 in the comparison corresponds to the 4th of 7 total in the full-length sequence.

There now follows a description of the use of an in vivo interaction trap system for the isolation of proteins which physically associate with thyroid hormone receptor and a description of exemplary interacting proteins (termed, TR-interacting proteins). This system may be used generally to isolate proteins which interact with any nuclear hormone receptor. Because the system has such general application for the isolation of nuclear hormone receptor-interacting proteins, this example is designed to illustrate, not limit, the invention.

Detailed Description

Applicants have used an in vivo interaction trap system (developed in the laboratory of Dr. Roger Brent) to identify and isolate proteins that physically interact with nuclear hormone receptors and, in particular, with the ligand binding domain of the rat receptor TRβ. This system, based on the modular nature of transcription factors, allows direct genetic selection for proteins capable of interacting with a desired protein.

Figure 1A:
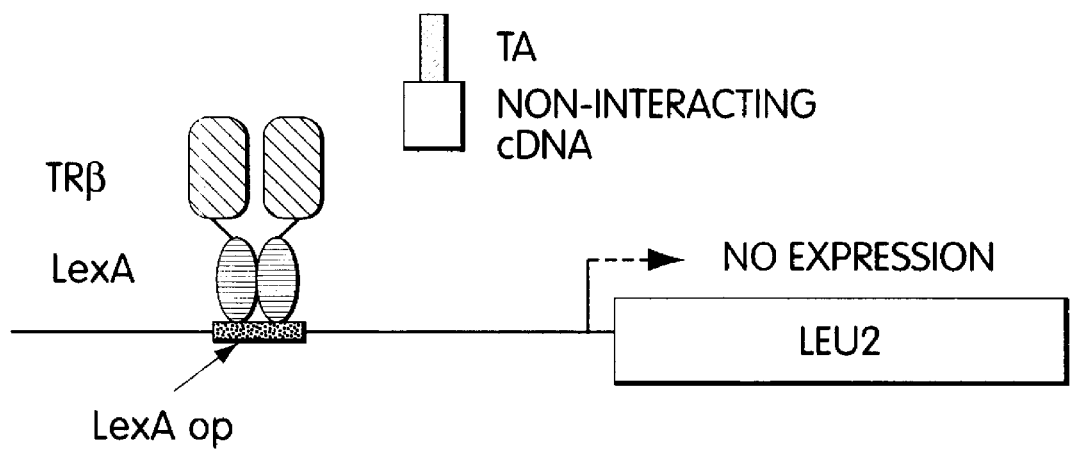
FIGS. 1A and 1B show a genetic selection in yeast for the isolation of TR-interacting protein-encoding cDNAs. The LexA/TRβ chimeras bind to the lexA binding site (lexA op) upstream of the LEU2 gene. (A) In cells expressing a fusion protein consisting of the B42 transactivation (TA) domain fused to a protein that does not interact specifically with the lexA/TR chimera, the LEU2 gene is not expressed, and the cells require supplemental leucine for growth. (B) In cells expressing a TA fusion to a protein capable of binding the lexA/TR chimera, the TA domain is brought specifically to the promoter LEU2 expression is increased, and the cells do not require supplemental leucine.
Figure 1B:
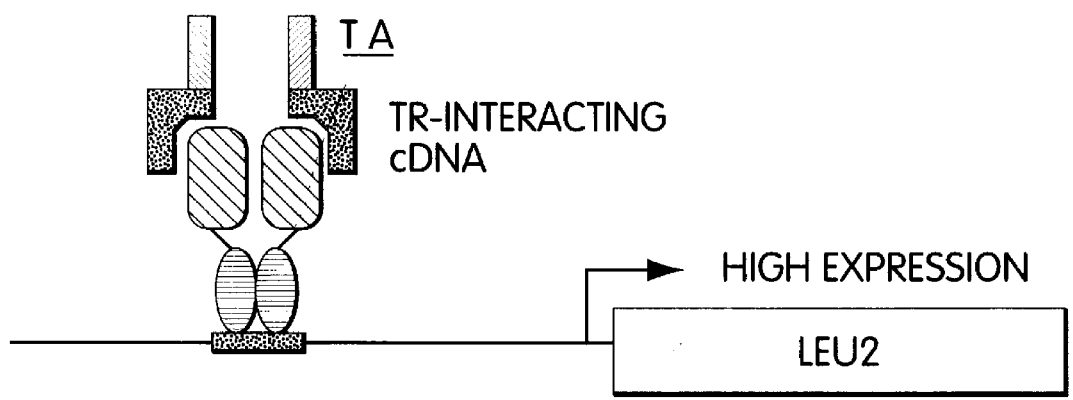

In general, DNA encoding the desired protein is fused to DNA encoding the C-terminus of a DNA binding domain, for example, the DNA binding domain of the bacterial repressor LexA protein, to generate a chimeric transcription factor, which can be tested for function in yeast. In the instant case, a lexA/TR chimera consisting of intact lexA fused to the hinge, ligand binding, and C terminal (D, E and F) domains of TRβ was found to be completely unable to activate transcription in either the presence or absence of T3 ligand. This lack of transcriptional activation by the lexA/TR chimera provided the basis for applicants' genetic selection. As shown in FIG. 1, a yeast strain in which expression of the LEU2 gene is dependent on binding of an activator to upstream lexA binding sites (i.e., operators) is unable to grow in the absence of added leucine when this chimera is expressed. However, if such a strain expresses a second chimeric protein which includes a relatively weak transcriptional activation domain (e.g., the B42 activation domain of Ma and Ptashne, Cell 51:113, 1987) fused to a protein capable of interacting specifically with lexA/TR, LEU2 gene expression is activated, and leucine is not required for growth.

Using this system, a number of proteins which interact with thyroid hormone receptor were isolated as follows. A plasmid cDNA library was produced by standard techniques from HeLa cell mRNA and had approximately $10^6$ original members. Each of these cDNA inserts was fused to the B42 transcriptional activation domain (Ma and Ptashne, Cell 51:113, 1987), and expression of the fusion protein was placed under the control of the inducible yeast GAL10 promoters In addition to the B42 activating domain, this expression construct also carried, amino to carboxy terminal, an ATG for protein expression, an optional nuclear localization sequence, and an optional epitope tag for rapid immunological detection of fusion protein synthesis. The plasmid also included replication origins for yeast and E. coli as well as selectable markers for both.

The fusion protein library was introduced into a yeast strain that expressed the lexA/TRβ chimera and also contained two reporter genes: a lexAop/LEU2 selection construct and a lexAop/β-galactosidase indicator construct. Approximately $10^7$ initial transformants were generated under nonselective conditions, representing a several fold redundancy relative to the original number of clones in the library. These transformants were recovered and replated under selective (leu$^-$) conditions in the presence or absence of thyroid hormone; based on the results of a functional analysis of intact TRs in yeast (Privalsky et al., Cell 63:1277–1286, 1990), a high concentration of triac ($10^{-5}$M) was added directly to the plates. A number of leucine-independent colonies that contained candidate TR-interacting cDNAs were obtained under both conditions.

The specificity of an interaction between TR and a candidate TR-interacting protein can be checked in several ways. For example, clones which do not activate expression of the lexA/β-galactosidase construct can be eliminated. These clones generally include yeast mutants that activate the LEU2 promoter or mammalian cDNAs that activate by some means other than through the lexA binding sites. Since the expression of the CDNA library fusion protein is under the control of an inducible promoter, the dependence of reporter gene expression on this chimera can also be tested by this criterion.

cDNA library plasmids were recovered from those yeast strains which passed the above tests. Each was reintroduced into the original lexA/TR strain, and their ability to specifically activate expression was confirmed. This step was included because yeast transformants frequently contain one or more plasmids, in addition to the one that allows survival under the selective conditions. To confirm their specificity for TRβ interaction, the rescued plasmids were also introduced into strains containing other lexA chimeras generated in Dr. Brent's laboratory; these included lexA/myc and lexA/cdc2. All of the clones were found to be specific for TRβ by this criterion. cDNA clones that passed all of the above tests were concluded to encode proteins that could specifically interact with the lexA/TR chimera.

Based on restriction mapping, these clones were sorted into distinct classes. Members of each class were sequenced across the fusion junction with the transcriptional activation domain. Sequences of many of these proteins are shown in FIGS. 2–28 (SEQ ID NOS: 1, 3, 6–30).

Although some clones have shown no significant similarities in searches of the sequence databases, most have shown some relationship to known proteins. As described below, two classes showed strong matches over limited domains to nuclear transcription factors. One clone unexpectedly appeared to encode a fragment of the human clathrin heavy chain. Since cell biology considerations argue that TRβ is quite unlikely to have a biologically relevant interaction with clathrin in mammalian cells, it can be assumed that the sensitivity of the selection system allows isolation of fragments of proteins that show some affinity for TR based solely on simple chemical interactions. Interacting proteins of this sort are useful for the production of peptides which interfere with thyroid hormone receptor function (see below).

Because RXRβ interacts with TR and is expressed in HeLa cells (Lied et al., Cell 68:377–395, 1992), RXR fusions would be expected to activate reporter gene expression and be isolated in this selection. To test this prediction, a fragment encoding the RXRα hinge and ligand binding domains was inserted in frame into the transcriptional activation domain fusion vector used to generate the original cDNA library. As expected, this RXR fusion construct allowed the lexA/TR tester strain, but not strains expressing other lexA chimeras, to survive in the absence of leucine and also activated expression of the lexA/β-galactosidase reporter gene (see Table 2). RXR, however, was not identified in the original screen. This is most likely explained by the fact that, although the original library was large, it was extensively amplified, which can decrease representation of rare cDNAs. Moreover, the fusion to the transcriptional activation domain must be in the correct frame and may be functional if the fusion occurs in only a relatively limited number of positions. Since members of the nuclear hormone receptor superfamily are generally expressed at extremely low levels, it is most likely that appropriate RXR clones were simply not present in the amplified library originally screened.

Unexpectedly, nearly all of the lexA/TR interacting cDNAs showed very strong dependence on hormone for activation. Two proteins, JL1 and JL2, which were isolated in the initial selection in the presence of triac, both interacted with the lexA/TR chimera much more strongly when triac was present, as judged by level of expression of β-galactosidase. This hormone$^+$ group constituted the majority of isolated clones (>10 different classes), although there were a smaller number in a hormone$^-$ group that interacted only when triac was absent. These classes are shown in Table 1.

TABLE 1

| | Class 1 |
|---|---|
| JL1; | homologous to HIV/TAT interacting proteins MSS1 (Nature 357:700–702, 1992), and to yeast SUG1 (Nature 357:698–700, 1992) |
| JL2; | contains LIM domain (Nature 344:876–879, 1992) |
| 112a-; | no significant homology to any known gene in current databank |
| 103a; | homology to homeobox protein CUT (Nature 333:629–635, 1988) |
| 203a; | homologous to bovine phosphatidylethanolamine-binding protein (EUR. J. BIOCHEM. 166, 333–338, 1987) |
| 204b; | homologous to kinesin-related protein (Mol. Cell. Biol. 11:3395–3398, 1991) |
| 205a; | no significant homology to any known gene in current databank |
| 249a; | no significant homology to any known gene in current databank |
| 351a; | homology to BCL3 (Cell 60:991–997, 1990) |
| 101a; | homology to GRP94 (J. Biol. Chem. 262: 8875–8883, 1987) |
| 223a; | no significant homology to any known gene in current databank |
| 239a; | contains HMG box (Nature 357:282–283, 1992) |
| 410a; | contains SH3 domain (Science 252:668–674, 1991) |
| 417a; | identical to human dUTP pyrophosphatase (Proc. Natl. Acad. Sci. U.S.A. 89:8020–8024, 1992) |
| 418a; | no significant homology to any known gene in current databank |
| 419a; | homology to yeast N-myristoyltransferase (Science 243:796–800, 1989) |
| | Class 2 |
| 107a-; | homologous to rat clathrin heavy chain (Proc. Natl. Acad. Sci. U.S.A. 84: 8805–8809, 1987) |
| 213a-; | no significant homology to any known gene in current databank |
| 113a-; | no significant homology to any known gene in current databank |
| 116a-; | no significant homology to any known gene in current databank |
| 309a-; | homologous to mouse perforin (Proc. Natl. Acad. Sci. U.S.A. 86:247–251, 1989) |
| 227b-; | homologous to mitochondrial hsp70 (DNA 8:233–243, 1989) |
| 224a-; | identical to human ferritin heavy chain (EMBO J. 3:23–27, 1984) |
| 312b-; | identical to human hnRNP C1/2 (Proc. Natl. Acad. Sci. U.S.A. 86:9788–9792, 1989) |
| 215a-; | no significant homology to any known gene in current databank |
| 223a-; | homology to (2'-5') oligoadenylate synthetase (EMBO J. 4:2249–2256, 1985) |
| 240a-; | no significant homology to any known gene in current databank |
| | Class 3 |
| 139a; | homology to possible transcription factor VAC1 (J. Biol. Chem. 267:618–623, 1992) |
| 110a-; | no significant homology to any known gene in current databank |

The fact that virtually all of the isolated clones were specific for one hormone state or the other was surprising.

The genetic properties of sample TR-interacting proteins and RXR fusion proteins are summarized in Table 2.

TABLE 2

| TA fusion | | Lex A fusion | | |
| --- | --- | --- | --- | --- |
| | | lexA | lexA/TR | lexA/c-myc |
| B42 (vector) | −T3 | leu$^-$,W | leu$^-$,W | leu$^{-,W}$ |
| | +T3 | " | " | " |
| JL1/JL2 | −T3 | leu$^-$,W | leu$^-$,W | leu$^-$,W |
| | +T3 | " | leu$^+$,B | " |
| RXR | −T3 | leu$^-$,W | leu$^+$,B | leu$^-$,W |
| | +T3 | " | leu$^+$,B | " |

Each of the strains shown in Table 2 contained both the lexAop/LEU2 and the lexAop/β-galactosidase reporter constructs, along with the indicated transcriptional activation (TA) domain fusion proteins; the cDNA cloning vector expressed the B42 transcriptional activation domain alone (Ma and Ptashne, Cell 51:113–119, 1987). Cells containing the indicated TA fusion proteins were transformed with each of the indicated lexA fusion vectors, and phenotypes were tested under various conditions. ±-T3 indicates the presence or absence of $10^{-5}$M triac in the plates (Privalsky et al., Cell 63:1277–1286, 1990); leu$^\pm$ denotes the ability of the transformed cells to grow on plates lacking leucine; W/B indicates formation of white or blue colonies on indicator plates containing the indicator X-gal. As expected, the activation conferred by the JL1, JL2, and RXR fusion proteins was dependent on the specific induction of the GAL10 promoter that controls their expression.

JL-1 and JL-2

The largest class of lexA/TR interacting cDNAs (17 individual isolates) encoded JL1 (also called thyroid hormone receptor-interacting protein 1, or TRIP1). All of the members of the class exhibited the properties summarized above, although some variations in the levels of expression of β-galactosidase in the presence or absence of hormone was observed for clones that varied in position of the junction to the B42 transactivation domain. JL1 is quite similar to several previously identified proteins, particularly TBP1, as indicated in FIG. 2. The functions of this family of proteins are diverse: TBP1 is a nuclear protein that has a poorly understood but apparently important role in transcriptional regulation of HIV (Nelbock et al., Science 248:1650–1653, 1990), while the mammalian protein VCP (Koller and Brownstein, Nature 325:542–545, 1987) and its apparent yeast homolog CDC48 (Frohlich et al., J. Cell. Biol. 114:443–453, 1991) are cytoplasmic proteins of unknown function. TBP1 was isolated by using labeled HIV TAT protein to screen a lambda gt11 expression library and has been found to interact directly with that important viral regulator but not with DNA. Although initially described as an inhibitor of TAT function in cotransfections, a more recent report indicates that TBP1 may act to stimulate TAT activity and may have a direct transcriptional activation function in its own right (Rosen, Abstract. Cold Spring Harbor Symp. Quant. Biol. 57:267, 1992). On these grounds, TBP could be considered a candidate transcriptional coactivator. JL1 is even more homologous to SUG1 (74%, see FIG. 2), a yeast gene recently isolated as a suppressor of a defective version of the GAL4 activator (Swaffield et al., Nature 357:698, 1992). By genetic analysis, SUG1 appears to be a coactivator capable of specifically interacting with GAL4, and JL1 similarly encodes a thyroid hormone-dependent coactivator protein. Functionally, they are at least partially homologous, with expression of JL-1 able to rescue a SUG1 temperature-sensitive lethal mutant in a yeast system in a similar manner to wild-type SUG1 (Swaffield et al., manuscript submitted). This interchangeability indicates that the SUG1 and JL-1 transcriptional function has been highly conserved, most likely within the conserved ATPase-containing domain common to the superfamily. Thus, they are likely to bind the same activation domains and exert transcriptional control in a similar manner.

JL2, encoded by a single recovered cDNA, includes two copies of the LIM domain originally identified as a conserved motif in three putative transcription factors: Lin-11 (Freyd et al., Nature 344:876–879, 1990), Isl-1 (Karlsson et al., Nature 344:879–882, 1990) and Mec-3 (Way, and Chalfie, Cell 54:5–16, 1988). In the context of endocrine control of gene expression, Isl-1 is particularly interesting since it is an activator of the insulin enhancer. It is expressed in both developing and mature islet cells and is thought to be involved in the initial differentiation of the islet cells, in addition to its presumed role in regulating insulin expression. Isl-1 is also expressed in a subset of neurons in the adult and, recently has been shown to be expressed at very early stages of embryonic motor neuron differentiation. The pattern of this early expression suggests that Isl-1 may play a primary role in the initial determination of motor neuron cell fate in response to inductive signals from the notochord and floor plate (Ericson et al., Science 256:155–1560, 1992). Consistent with this possibility, lin-11 and mec-3 are both *C. elegans* developmental regulators, associated with cell lineage determination in mechanosensory neurons and a vulval precursor cell, respectively.

Lin-11, Isl-1, and mec-3 contain a homeobox-type DNA binding domain in addition to two copies of the LIM domain, as do other recently identified members of this family (see, e.g., Cohen et al., Genes & Dev. 6:715–729, 1992; Taira et al., Genes & Dev. 6:356–366, 1992). However, a homeodomain is absent in a three related LIM domain-containing proteins called rhombotins 1–3, at least two of which are the products of putative oncogenes (Rosen, Abstract, Cold Spring Harbor Symp. Quant. Biol. 57:267, 1992). The LIM domain consensus sequence contains conserved cysteine and histidine residues, and it has recently been demonstrated that at least the lin-11 version binds metal ions (2 atoms of Zn and 4 of Fe; Li et al., Proc. Natl. Acad. Sci. U.S.A. 88:9210, 1991). As indicated in FIG. 3, JL2 has a good match with the LIM consensus in lin-11; it does not, however, include a homeobox. In this regard, JL2 appears to be more like the rhombotins than it is like the transcription factors lin-11, Isl-1 , and mec-3.

Figure 29:
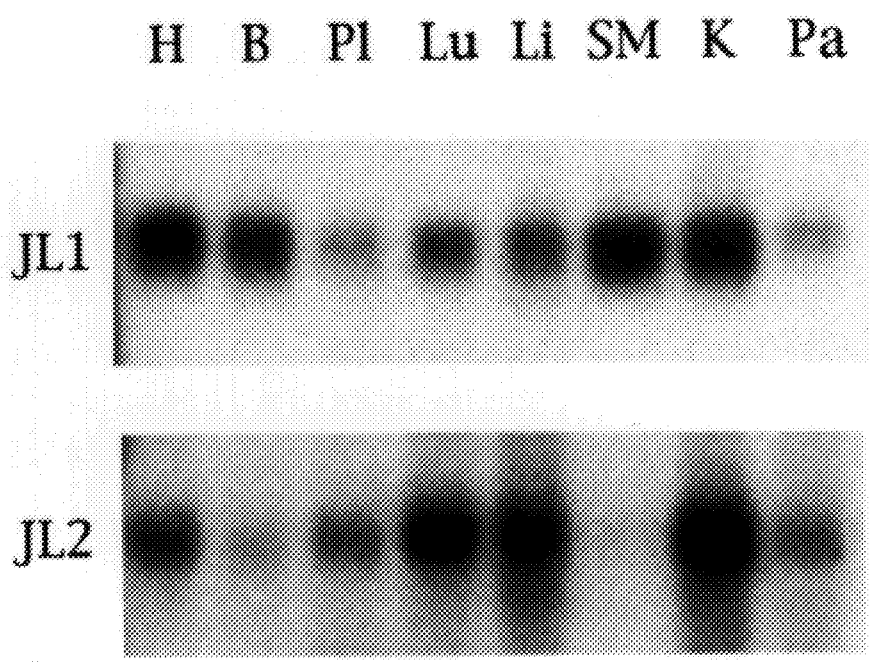
FIG. 29 shows a Northern analysis of JL1 and JL2 expression in various human tissues. Specifically, 2 $\mu$g of poly A$^+$ mRNA from the indicated tissues (H, heart; B, brain; Pl, placenta; Lu, lung; Li, liver; SM, skeletal muscle; K, kidney; Pa, pancreas; all obtained from Clontech, Palo Alto, Calif.) was hybridized to JL1 and JL2 probes by standard techniques and washed at high stringency (see Ausubel et al., infra). Equivalent loading of RNA was verified by hybridization with a human actin cDNA probe.

An initial determination of the pattern of expression of JL1 and JL2 has begun. As indicated in FIG. 29, the approximately 2.1 kb JL1 mRNA is expressed at various levels in all the human tissues examined. The slightly smaller 1.8 kb JL2 mRNA is expressed in a somewhat narrower range of tissues. Based on the amount of time required to visualize the bands, both mRNAs are present at very low levels, consistent with a regulatory role. As judged by exposure time, the JL1 mRNA appears to be expressed at an approximately 6 fold higher level than that of JL2, as would be expected from the higher number of JL1 clones isolated.

S351a

The isolated polypeptide 351a was found to have some homology (about 40% identity at the amino acid level) to BCL3. The BCL3 gene product is characterized by seven 30 amino acid ankyrin repeats (Ohno et al., *Cell* 60:991–997, 1990), so named because of their initial identification in the erythrocyte membrane protein ankyrin. There are now many examples of related proteins, which share the repeated structure consisting of a loosely conserved, approximately 30 amino acid motif (the ankyrin repeat). These related proteins have diverse functions, but one subgroup, including BCL3, IκB, and others have specific functions in the regulation of transcription. These proteins bind specifically to the family of related proteins that form a dimeric transcription factor generically known as NFκB. The interaction of IκB with NFκB inhibits its ability to activate transcription of target genes because the complex is retained in the cytoplasm. This retention is possibly due to IκB binding to and masking NFκB's nuclear localization signals. The interaction with BCL3, in contrast, apparently occurs in the nucleus and leads to a stimulation of transcriptional activity by unknown mechanisms. This family of proteins thus appears to have a modulatory effect on transcription, which allows regulation of a variety of gene products involved in numerous cellular responses. Hence, members of this subgroup can have either inhibitory or stimulatory effects on transcription, and it is unclear what function in this regard the 351a peptide has in its interactions with TR. FIG. 30 shows the similarity between 351a and the relevant portion of BCL3. The ankyrin repeats of BCL3 are underlined. The similarity is clearly greatest over the N-terminal portion of the sequence shown, in the stretch which corresponds to the 4th of the 7 repeats in BCL3. Overall, the relationship is not particularly strong, and may account for the observation the BCL3 does not interact with either TR or RXR in the interaction trap of this invention, while 351a does. 351a clearly has a ligand dependent TR and RXR interaction function not shared by its closest relative within the family of proteins containing ankyrin repeats.

Experiments in yeast have shown that although both the lexA-TR chimera used in the interaction trap and TR alone activate transcription in yeast very poorly in the presence or absence of thyroid hormone, coexpression of the TR heterodimer partner RXR restores hormone dependent transcriptional activation of both (on lexA operators and TR binding sites, respectively). Adding the lexA-351a construct to the intact TR +RXR strongly inhibits this latter activation. This inhibition could be a consequence of a direct inhibition associated with 351a binding, or could be an indirect effect associated with the fact that the lexA-351a chimera is missing essential sequences necessary for a co-stimulatory function analogous to that of BCL3. In an additional series of experiments, lexA-351a alone was also found to be transcriptionally inactive in yeast. However, coexpression of intact TR causes lexA-351a to become a T3-dependent transcriptional activator. This indicates that the interaction of 351a with TR does not result in a complex that is inherently inactive, resolution of the larger question of whether the native 351-TR interaction is stimulatory or inhibitory will require analysis of the function of the full length 351a protein.

From a practical point of view, the inhibitory effect of the lexA-351a chimera provides a direct demonstration of a potentially useful function of the truncated protein, namely inhibition of TR function. Liposomes or other delivery systems known in the art could be employed to deliver this truncated protein or the minimum biologically active fragment thereof for therapeutic uses. The direct demonstration of the negative effect provides a clear demonstration of the general concept of using 351a to block TR action. 351a could provide a therapeutically useful antagonist of TR function analogous to, for instance, the anti-steroid effects of RU486, a drug that inhibits transcription in members of the nuclear hormone receptor family. The mechanism of action of RU486 is distinct from 351a, and does not exert effects on thyroid hormone receptors, and thus the inhibitory effect of 351a on transcriptional regulation in the thyroid hormone receptor system is of potentially major significance.

To determine whether a TR-interacting protein has a positive or a negative effect on TR function, cotransfections of the TR-interacting protein expression vector and a TRβ or TRα expression vector are carried out by standard techniques, preferably, in a host cell line that does not express significant levels of the TR-interacting protein (see, e.g., Ausubel et al., Current Protocols in Molecular Biology, John Wiley & Sons, 1989). A TR-interacting protein which acts as a positive regulator (e.g., a coactivator), is indicated by increased TR activity in such an assay. Conversely, a TR-interacting protein which acts as a negative regulator is indicated by reduced TR activity. Cotransfection assays of this sort are generally described in Ausubel et al. (supra).

In one particular example, the TR-interacting protein-encoding cDNA is inserted into the CDM8 vector (Seed, B., Nature 329:840, 1987), and increasing doses of this plasmid are cotransfected with a TRβ expression vector (Brent et al., J. Biol. Chem. 264:178, 1989) plus one of several different reporter genes containing various T3REs linked, e.g., to the herpes virus thymidine kinase (TK) gene (Brent suPra). In these transfections, the level of total expression vector is maintained at a constant level by addition of CDM8, as necessary. To control for variations in transfection efficiency and for effects of the TR-interacting protein on the TK promoter, transfections also include pTKGH (Selden et al., Moll. Cell. Biol. 6:3173, 1986), a plasmid which directs expression of human growth hormone under the control of the same TK promoter. As controls for regulatory effects, Pit1, c-fos and c-jun may also be cotransfected with TRβ and the T3RE reporters.

Since the relative and absolute levels of expression of TRβ and its potential partners may be crucial for observation of any effect, a negative result is first confirmed at a variety of doses of each vector. Several cell lines are also examined. If however, no evidence for a specific effect of a TR-interacting protein on TR function is observed after these steps, it will be concluded that the interaction with TRβ is likely to be an artifact of the sensitivity of the genetic selection originally used to isolate them.

If, on the other hand, the TR-interacting protein alters TR function, the specificity of the effect is examined. Simple cotransfections of the TR-interacting protein expression vector with RSVCAT or TKCAT vectors is used to confirm that any negative effect is not a consequence of squelching (Ptashne and Gann, Nature 346:329–331, 1990). Cotransfections of appropriate reporters with the TR-interacting protein expression vectors plus vectors expressing TRα, the RARs, VDR, GR, ER or others may also be carried out.

The portions of any particular TR-interacting protein required for functional interaction may be determined initially by standard deletion analysis, with mutant proteins tested by the above cotransfection assay. The results of such mapping may be confirmed and extended by testing the effect of the same mutations on the lexA/TR dependent activation of expression in yeast, and by the following biochemical interaction assays.

To determine directly whether a TR-interacting protein can interact with thyroid hormone receptor, antiserum directed against one of the potential partners is tested for its ability to coimmunoprecipitate the other. This may be assayed directly using bacterially-produced TR proteins and antiserum or monoclonal antibodies that recognize some region of the TRβ protein. In one particular example of such an assay, in vitro translated, $^{35}$S labeled TR-interacting protein is mixed with TRβ protein in the presence or absence of T3, and the mixture is immunoprecipitated with an antiserum that recognizes the N-terminus of the TR. Similarly labeled RXRβ protein, which is known to interact strongly with TRβ in such procedures, is used as a positive control. The immunoprecipitated material is resolved by SDS PAGE, and the presence of the TR-interacting protein or RXR in such immunoprecipitates is assessed by autoradiography. The observation of T3-dependent coimmunoprecipitation of the potential TR binding proteins with the TR provides strong evidence for a direct interaction with the receptor. A general description of in vitro translation of proteins is described in Hope and Struhl, Cell 43:177–188, 1985. Labelling proteins with $^{35}$S, production of antibodies (including monoclonal antibodies), and immunoprecipitation procedures are described in Ausubel (infra).

Lack of such a coimmunoprecipitation may suggest that the interaction of a particular protein with TR is too transient to be detected by this approach. This can be tested by addition of various crosslinking reagents to the binding reactions, as described in the analysis of the interactions of GR with AP-1, for example (Yang-Yen et al., Cell 62:1205–1215, 1990). It is important to control for the variety of artifactual associations that may complicate interpretation of such studies. If crosslinking does not reveal an interaction between a TR-interacting protein and TRβ, even in the presence of extracts that might supply additional cofactors required, it may be that their interaction in yeast is artifactual.

Truncated versions of TR-interacting proteins can also be tested using this method to identify specific portions of each protein required for TR interaction. This is of particular importance from the point of view of potential pharmacologic intervention with the interaction, since such fragments may facilitate the production of specific inhibitors of TR function.

TR-INTERACTING PROTEINS AND ANTIBODIES

Polypeptide Expression

In general, polypeptides according to the invention may be produced by transformation of a suitable host cell with all or part of a TR-interacting protein-encoding cDNA fragment (e.g., the cDNA described above) in a suitable expression vehicle.

Those skilled in the field of molecular biology will understand that any of a wide variety of expression systems may be used to provide the recombinant protein. The precise host cell used is not critical to the invention. The TR-interacting protein may be produced in a prokaryotic host (e.g., *E. coli*) or in a eukaryotic host (e.g., *Saccharomyces cerevisiae* or mammalian cells, e.g., COS 1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1989). The method of transformation or transfection and the choice of expression vehicle will depend on the host system selected. Transformation and transfection methods are described, e.g., in Ausubel et al. (*Current Protocols in Molecular Biology*, John Wiley & Sons, New York, 1989); expression vehicles may be chosen from those provided, e.g., in *Cloning Vectors: A Laboratory Manual* (P. H. Pouwels et al., 1985, Supp. 1987).

One preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a TR-interacting protein would be inserted into the pMAMneo vector in an orientation designed to allow expression. The recombinant TR-interacting protein would be isolated as described below. Other preferable host cells which may be used in conjunction with the pMAMneo expression vehicle include COS cells and CHO cells (ATCC Accession Nos. CRL 1650 and CCL 61, respectively).

Alternatively, a TR-interacting protein is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the TR-interacting protein is cloned into an expression vector which includes the dihydrofolate reductase (DHFR) gene. Integration of the plasmid and, therefore, the TR-interacting protein-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV (A) (described in Ausubel et al., supra). Any of the host cells described above or, preferably, a DHFR-deficient CHO cell line (e.g., CHO DHFR$^-$ cells, ATCC Accession No. CRL 9096) are among the host cells preferred for DHFR selection of a stably-transfected cell line or DHFR-mediated gene amplification.

Once the recombinant TR-interacting protein is expressed, it is isolated, e.g., using affinity chromatography. In one example, an anti-TR-interacting protein antibody (e.g., produced as described herein) may be attached to a column and used to isolate the TR-interacting protein. Lysis and fractionation of TR-interacting protein-harboring cells prior to affinity chromatography may be performed by standard methods (see, e.g., Ausubel et al., supra). Alternatively, a TR-interacting protein fusion protein, for example, a TR-interacting protein-maltose binding protein, a TR-interacting protein-β-galactosidase, or a TR-interacting protein-trpE fusion protein, may be constructed and used for TR-interacting protein isolation (see, e.g., Ausubel et al., supra; New England Biolabs, Beverly, Mass.).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short TR-interacting protein fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful TR-interacting protein fragments or analogs (described herein).

Anti-TR-Interacting Protein Antibodies

Human TR-interacting protein (or immunogenic fragments or analogues) may be used to raise antibodies useful in the invention; such polypeptides may be produced by recombinant or peptide synthetic techniques (see, e.g., *Solid Phase Peptide Synthesis*, supra; Ausubel et al., supra). The peptides may be coupled to a carrier protein, such as KLH as described in Ausubel et al, supra. The KLH-peptide is mixed with Freund's adjuvant and injected into guinea pigs, rats, or preferably rabbits. Antibodies may be purified by peptide antigen affinity chromatography.

Monoclonal antibodies may also be prepared using the TR-interacting proteins described above and standard hybridoma technology (see, e.g., Kohler et al., Nature 256:495, 1975; Kohler et al., *Eur. J. Immunol.* 6:511, 1976; Kohler et al., *Eur. J. Immunol.* 6:292, 1976; Hammerling et al., *In Monoclonal Antibodies and T Cell Hybridomas*, Elsevier, N.Y., 1981; Ausubel et al., supra).

Once produced, polyclonal or monoclonal antibodies are tested for specific TR-interacting protein recognition by Western blot or immunoprecipitation analysis (by the methods described in Ausubel et al., supra). Antibodies which specifically recognize a TR-interacting protein are considered to be useful in the invention; such antibodies may be used, e.g., in an immunoassay to monitor the level of TR-interacting protein produced by a mammal or to determine the subcellular location of any of these thyroid hormone receptor modulatory proteins.

Preferably, antibodies of the invention are produced using fragments of the TR-interacting protein which lie outside highly conserved regions and appear likely to be antigenic, by criteria such as high frequency of charged residues. In one specific example, such fragments are generated by standard techniques of PCR and cloned into the pGEX expression vector (Ausubel, F. M. et al., *Current Protocols in Molecular Biology* (Greene Pub. Assoc., New York, 1992). Fusion proteins are expressed in *E. coli* and purified using a glutathione agarose affinity matrix as described in (Ausubel, F. M. et al., *Current Protocols in Molecular Biology* (Greene Pub. Assoc., New York, 1992)). To attempt to minimize the potential problems of low affinity or specificity of antisera, two or three such fusions are generated for each protein, and each fusion is injected into two rabbits. Antisera are raised by injections in a series including at least three booster injections. This approach has been successfully used by applicants to generate antibodies capable of discriminating between the different TR isoforms.

Antisera is cleared of anti-GST antibodies using GST immobilized on a glutathione column, and the antisera are checked by ELISA for titer and specificity, using GST fusion proteins as controls. Antisera is also checked for its ability to immunoprecipitate in vitro translated TR-interacting proteins or control proteins, such as Pit-1 or RARα. Western blots of total or nuclear vs. cytoplasmic fractionated HeLa cell proteins are also probed with the antisera to assess specificity and to characterize subcellular compartmentalization. In these and other immunologic assays, specificity is confirmed by the specific competition with the GST fusion protein.

Once the specificity of an antiserum is confirmed, it may be used in any standard indirect immunofluorescence procedure to determine the subcellular distribution of the TR-interacting protein in a particular cell type. Based on their similarity to nuclear transcriptional regulators and their interaction with TRs, TR-interacting proteins are likely to be nuclear localized.

Use

The proteins described herein interact with thyroid hormone receptor and are thus likely to mediate or modulate TR function. Because of their effects on thyroid receptor activity, such proteins (or peptides derived from these proteins, particularly, short peptides which are capable of TR interaction), may facilitate the production of pharmacologic modifiers of receptor function.

In particular, TR-interacting proteins of the invention which positively regulate TR function in vivo or in vitro (e.g., as assayed in cotransfections as described above) may be used to produce therapeutic peptides which include a TR interaction domain but which lack a TR activity-enhancing domain, for example, a domain which interacts with the transcriptional apparatus; the efficacy of such peptides may also, e.g., as assayed as described above. Such peptides would bind TR, interfering with receptor binding by the native TR-interacting protein, and thereby reducing TR activity. Peptides of this sort would be useful in the treatment of hyperthyroidism.

Conversely, interacting peptides derived from TR-interacting proteins which negatively regulate TR function, as assayed in vivo or in vitro (again, e.g., by the assays described above) may be used to produce therapeutic peptides which block the normal interaction between the receptor and the negatively acting TR-interacting protein. These peptides may similarly be administered to a mammal to treat thyroid disorders.

Such therapeutic polypeptides of the invention may be administered by any appropriate route, e.g., intravenously, at a dosage which is effective to increase or decrease thyroid function. Treatment may be repeated as necessary for alleviation of disease symptoms.

The polypeptides of the invention are also useful for identifying those compartments of mammalian cells which contain proteins important to the function of the thyroid hormone receptor. Antibodies specific for a particular TR-interacting protein (or any nuclear hormone receptor-interacting protein) may be produced as described above. The normal subcellular location of the protein is then determined either in situ or using fractionated cells by any standard immunological or immunohistochemical procedure (see, e.g., Ausubel et al., supra; Bancroft and Stevens, *Theory and Practice of Histological Techniques*, Churchill Livingstone, 1982).

Antibodies specific for TR-interacting proteins also find diagnostic use in the detection or monitoring of thyroid disorders. Levels of a TR-interacting protein in a sample may be assayed by any standard technique. For example, its expression may be monitored by standard Northern blot analysis or may be aided by PCR (see, e.g., Ausubel et al., supra; *PCR Technology: Principles and Applications for DNA Amplification*, ed., H. A. Ehrlich, Stockton Press, N.Y.). These techniques are enabled by the provision of the TR-interacting protein sequences described herein. Alternatively, standard immunological or immunohistochemical procedures (e.g., those described above) may also be used with the antibodies described herein for TR-interacting protein detection.

Other Embodiments

In other embodiments, the invention includes any protein which is substantially homologous to a human TR-interacting protein (FIGS. 2–28, SEQ ID NOS: 1, 3, 6–30); such homologs include other substantially pure naturally occurring mammalian TR-interacting protein proteins as well as allelic variants; natural mutants; induced mutants;

proteins encoded by DNA that hybridizes to the TR-interacting protein sequence of any of FIGS. 2–28(SEQ ID NOS: 1, 3, 6–30) under high stringency conditions or low stringency conditions (e.g., washing at 2× SSC at 40° C. with a probe length of at least 40 nucleotides); and polypeptides or proteins specifically bound by antisera directed to a TR-interacting protein, especially by antisera to the TR binding domain of the TR-interacting protein. The term also includes chimeric polypeptides that include a TR-interacting protein fragment.

The invention further includes analogs of any naturally occurring TR-interacting protein. Analogs can differ from the naturally occurring TR-interacting protein by amino acid sequence differences, by post-translational modifications, or by both. Analogs of the invention will generally exhibit at least 80%, more preferably 90%, and most preferably 95% or even 99%, homology with all or part of a naturally occurring TR-interacting protein sequence. The length of comparison sequences will be at least 8 amino acid residues, preferably at least 24 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally occurring TR-interacting protein by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, hereby incorporated by reference; or Ausubel et al., *Current Protocols in Molecular Biology*, John Wiley & Sons, 1989, hereby incorporated by reference). Also included are cyclized peptides molecules and analogs which contain residues other than L-amino acids, e.g., D-amino acids or non-naturally occurring or synthetic amino acids, e.g., β or γ amino acids.

In addition to full-length polypeptides, the invention also includes TR-interacting protein fragments. As used herein, the term "fragment", means at least 10 contiguous amino acids, preferably at least 30 contiguous amino acids, more preferably at least 50 contiguous amino acids, and most preferably at least 60 to 80 or more contiguous amino acids. Fragments of TR-interacting proteins can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate interaction of the peptide with a thyroid hormone receptor.

Other embodiments are within the following claims.

SEQUENCE LISTING ( 1 ) GENERAL INFORMATION:

( i i i ) NUMBER OF SEQUENCES: 31

( 2 ) INFORMATION FOR SEQ ID NO: 1:

( i ) SEQUENCE CHARACTERISTICS:
( A ) LENGTH: 406
( B ) TYPE: amino acid
( C ) STRANDEDNESS:
( D ) TOPOLOGY: linear ( x i ) SEQUENCE DESCRIPTION: SEQ ID NO: 1:

```
Met Ala Leu Asp Gly Pro Glu Gln Met Glu Leu Glu Glu Gly Lys Ala
 1               5                  10                  15

Gly Ser Gly Leu Arg Gln Tyr Tyr Leu Ser Lys Ile Glu Glu Leu Gln
            20                  25                  30

Leu Ile Val Asn Asp Lys Ser Gln Asn Leu Arg Arg Leu Gln Ala Gln
        35                  40                  45

Arg Asn Glu Leu Asn Ala Lys Val Arg Leu Leu Arg Glu Glu Leu Gln
    50                  55                  60

Leu Leu Gln Glu Gln Gly Ser Tyr Val Gly Glu Val Val Arg Ala Met
65                  70                  75                  80

Asp Lys Lys Lys Val Leu Val Lys Val His Pro Glu Gly Lys Phe Val
                85                  90                  95

Val Asp Val Asp Lys Asn Ile Asp Ile Asn Asp Val Thr Pro Asn Cys
            100                 105                 110

Arg Val Ala Leu Arg Asn Asp Ser Tyr Thr Leu His Lys Ile Leu Pro
        115                 120                 125

Asn Lys Val Asp Pro Leu Val Ser Leu Met Met Val Glu Lys Val Pro
    130                 135                 140
```

```
Asp  Ser  Thr  Tyr  Glu  Met  Ile  Gly  Gly  Leu  Asp  Lys  Gln  Ile  Lys  Glu
145                      150                      155                      160

Ile  Lys  Glu  Val  Ile  Glu  Leu  Pro  Val  Lys  His  Pro  Glu  Leu  Phe  Glu
                    165                      170                      175

Ala  Leu  Gly  Ile  Ala  Gln  Pro  Lys  Gly  Val  Leu  Leu  Tyr  Gly  Pro  Pro
                    180                      185                      190

Gly  Thr  Gly  Lys  Thr  Leu  Leu  Ala  Arg  Ala  Val  Ala  His  His  Thr  Asp
          195                      200                      205

Cys  Thr  Phe  Ile  Arg  Val  Ser  Gly  Ser  Glu  Leu  Val  Gln  Lys  Phe  Ile
          210                      215                      220

Gly  Glu  Gly  Ala  Arg  Met  Val  Arg  Glu  Leu  Phe  Val  Met  Ala  Arg  Glu
225                      230                      235                      240

His  Ala  Pro  Ser  Ile  Ile  Phe  Met  Asp  Glu  Ile  Asp  Ser  Ile  Gly  Ser
                    245                      250                      255

Ser  Arg  Leu  Glu  Gly  Gly  Ser  Gly  Gly  Ser  Ser  Glu  Val  Gln  Arg  Gln
                260                      265                      270

Met  Leu  Glu  Leu  Leu  Asn  Gln  Leu  Asp  Gly  Phe  Glu  Ala  Thr  Lys  Asn
          275                      280                      285

Ile  Lys  Val  Ile  Met  Ala  Thr  Asn  Arg  Ile  Asp  Met  Leu  Asp  Ser  Ala
     290                      295                      300

Leu  Leu  Arg  Pro  Gly  Arg  Ile  Asp  Arg  Lys  Ile  Glu  Phe  Pro  Pro  Pro
305                      310                      315                      320

Asn  Glu  Glu  Ala  Arg  Leu  Asp  Ile  Leu  Lys  Ile  His  Ser  Arg  Lys  Met
               325                      330                      335

Asn  Leu  Thr  Arg  Gly  Ile  Asn  Leu  Arg  Lys  Ile  Ala  Glu  Leu  Met  Pro
          340                      345                      350

Gly  Ala  Ser  Gly  Ala  Glu  Val  Lys  Gly  Val  Cys  Thr  Glu  Ala  Gly  Met
          355                      360                      365

Tyr  Ala  Leu  Arg  Glu  Arg  Arg  Val  His  Val  Thr  Gln  Glu  Asp  Phe  Glu
     370                      375                      380

Met  Ala  Val  Ala  Lys  Val  Met  Gln  Lys  Asp  Ser  Glu  Lys  Asn  Met  Ser
385                      390                      395                      400

Ile  Lys  Lys  Leu  Trp  Lys
                    405
```

( 2 ) INFORMATION FOR SEQ ID NO: 2:

( i ) SEQUENCE CHARACTERISTICS:
        ( A ) LENGTH: 405
        ( B ) TYPE: amino acid
        ( C ) STRANDEDNESS:
        ( D ) TOPOLOGY: linear ( x i ) SEQUENCE DESCRIPTION: SEQ ID NO: 2:

```
Met  Thr  Ala  Ala  Val  Thr  Ser  Ser  Asn  Ile  Val  Leu  Glu  Thr  His  Glu
1                   5                        10                       15

Ser  Gly  Ile  Lys  Pro  Tyr  Phe  Glu  Gln  Lys  Ile  Gln  Glu  Thr  Glu  Leu
                    20                       25                       30

Lys  Ile  Arg  Ser  Lys  Thr  Glu  Asn  Gly  Arg  Arg  Leu  Glu  Ala  Gln  Arg
               35                       40                       45

Asn  Ala  Leu  Asn  Asp  Lys  Val  Arg  Phe  Ile  Lys  Asp  Glu  Leu  Arg  Leu
     50                       55                       60

Leu  Gln  Glu  Pro  Gly  Ser  Tyr  Val  Gly  Glu  Val  Ile  Lys  Ile  Val  Ser
65                       70                       75                       80

Asp  Lys  Lys  Val  Leu  Val  Lys  Val  Gln  Pro  Glu  Gly  Lys  Tyr  Ile  Val
                    85                       90                       95
```

| | | | | | | | | | | | | | | |
|---|---|---|---|---|---|---|---|---|---|---|---|---|---|---|
| Asp | Val | Ala | Lys<br>100 | Asp | Ile | Asn | Val | Lys<br>105 | Asp | Leu | Lys | Ala | Ser<br>110 | Gln | Arg |
| Val | Cys | Leu<br>115 | Arg | Ser | Asp | Ser | Tyr<br>120 | Met | Leu | His | Lys | Val<br>125 | Leu | Glu | Asn |
| Lys | Ala<br>130 | Asp | Pro | Leu | Val | Ser<br>135 | Ile | Met | Met | Val | Glu<br>140 | Lys | Val | Pro | Asp |
| Ser<br>145 | Thr | Tyr | Asp | Met | Val<br>150 | Gly | Gly | Leu | Thr | Lys<br>155 | Gln | Ile | Lys | Glu | Ile<br>160 |
| Lys | Glu | Val | Ile | Glu<br>165 | Leu | Pro | Val | Lys | His<br>170 | Pro | Glu | Leu | Phe | Glu<br>175 | Ser |
| Leu | Gly | Ile | Ala | Gln<br>180 | Pro | Lys | Gly | Val<br>185 | Ile | Leu | Tyr | Gly | Pro<br>190 | Pro | Gly |
| Thr | Gly | Lys<br>195 | Thr | Leu | Leu | Ala | Arg<br>200 | Ala | Val | Ala | His<br>205 | His | Thr | Asp | Cys |
| Lys | Phe<br>210 | Ile | Arg | Val | Ser | Gly<br>215 | Ala | Glu | Leu | Val | Gln<br>220 | Lys | Tyr | Ile | Gly |
| Glu<br>225 | Gly | Ser | Arg | Met | Val<br>230 | Arg | Glu | Leu | Phe | Val<br>235 | Met | Ala | Arg | Glu | His<br>240 |
| Ala | Pro | Ser | Ile | Ile<br>245 | Phe | Met | Asp | Glu | Ile<br>250 | Asp | Ser | Ile | Gly | Ser<br>255 | Thr |
| Arg | Val | Glu | Gly<br>260 | Ser | Gly | Gly | Gly | Asp<br>265 | Ser | Glu | Val | Gln | Arg<br>270 | Thr | Met |
| Leu | Glu | Leu<br>275 | Leu | Asn | Gln | Leu | Asp<br>280 | Gly | Phe | Glu | Thr | Ser<br>285 | Lys | Asn | Ile |
| Lys | Ile<br>290 | Ile | Met | Ala | Thr | Asn<br>295 | Arg | Leu | Asp | Ile | Leu<br>300 | Asp | Pro | Ala | Leu |
| Leu<br>305 | Arg | Pro | Gly | Arg | Ile<br>310 | Asp | Arg | Lys | Ile | Glu<br>315 | Phe | Pro | Pro | Pro<br>320 | Ser |
| Val | Ala | Ala | Arg | Ala<br>325 | Glu | Ile | Leu | Arg | Ile<br>330 | His | Ser | Arg | Lys | Met<br>335 | Asn |
| Leu | Thr | Arg | Gly<br>340 | Ile | Asn | Leu | Arg | Lys<br>345 | Val | Ala | Glu | Lys | Met<br>350 | Asn | Gly |
| Cys | Ser | Gly<br>355 | Ala | Asp | Val | Lys | Gly<br>360 | Val | Cys | Thr | Glu | Ala<br>365 | Gly | Met | Tyr |
| Ala | Leu<br>370 | Arg | Glu | Arg | Arg | Ile<br>375 | His | Val | Thr | Gln | Glu<br>380 | Asp | Phe | Glu | Leu |
| Ala<br>385 | Val | Gly | Lys | Val | Met<br>390 | Asn | Lys | Asn | Gln | Glu<br>395 | Thr | Ala | Ile | Ser | Val<br>400 |
| Ala | Lys | Leu | Phe | Lys<br>405 | | | | | | | | | | | |

( 2 ) INFORMATION FOR SEQ ID NO: 3:

( i ) SEQUENCE CHARACTERISTICS:
        ( A ) LENGTH: 185
        ( B ) TYPE: amino acid
        ( C ) STRANDEDNESS:
        ( D ) TOPOLOGY: linear ( x i ) SEQUENCE DESCRIPTION: SEQ ID NO: 3:

| | | | | | | | | | | | | | | |
|---|---|---|---|---|---|---|---|---|---|---|---|---|---|---|
| Met<br>1 | Pro | Gly | Pro | Leu<br>5 | Arg | Gly | Gln | His | Phe<br>10 | Tyr | Ala | Val | Glu | Arg<br>15 | Arg |
| Ala | Tyr | Cys | Glu<br>20 | Gly | Cys | Tyr | Val | Ala<br>25 | Thr | Leu | Glu | Lys | Cys<br>30 | Ala | Thr |
| Cys | Ser | Gln<br>35 | Pro | Ile | Leu | Asp | Arg<br>40 | Ile | Leu | Arg | Ala | Met<br>45 | Gly | Lys | Ala |

| Tyr | His | Pro | Gly | Cys | Phe | Thr | Cys | Val | Val | Cys | His | Arg | Gly | Leu | Asp |
|     | 50  |     |     |     |     | 55  |     |     |     |     | 60  |     |     |     |     |

| Gly | Ile | Pro | Phe | Thr | Val | Asp | Ala | Thr | Ser | Gln | Ile | His | Cys | Ile | Glu |
| 65  |     |     |     |     | 70  |     |     |     |     | 75  |     |     |     |     | 80  |

| Asp | Phe | His | Arg | Lys | Phe | Ala | Pro | Arg | Cys | Ser | Val | Cys | Gly | Gly | Ala |
|     |     |     |     | 85  |     |     |     |     | 90  |     |     |     |     | 95  |     |

| Ile | Met | Pro | Glu | Pro | Gly | Gln | Glu | Glu | Thr | Val | Arg | Ile | Val | Ala | Leu |
|     |     |     | 100 |     |     |     |     | 105 |     |     |     |     |     | 110 |     |

| Asp | Arg | Ser | Phe | His | Ile | Gly | Cys | Tyr | Lys | Cys | Glu | Glu | Cys | Gly | Leu |
|     |     | 115 |     |     |     |     | 120 |     |     |     |     | 125 |     |     |     |

| Leu | Leu | Ser | Ser | Glu | Gly | Glu | Cys | Gln | Gly | Cys | Tyr | Pro | Leu | Asp | Gly |
|     | 130 |     |     |     |     | 135 |     |     |     |     | 140 |     |     |     |     |

| His | Ile | Leu | Cys | Lys | Ala | Cys | Arg | Pro | Gly | Ala | Ser | Arg | Ser | Ser | Gln |
| 145 |     |     |     |     | 150 |     |     |     |     | 155 |     |     |     |     | 160 |

| Pro | Pro | Ser | Gly | Leu | Thr | Ala | Glu | Ser | Ser | Met | Lys | Tyr | Leu | Leu | Gly |
|     |     |     |     | 165 |     |     |     |     | 170 |     |     |     |     | 175 |     |

| Ser | Gln | Phe | Gln | Phe | Pro | Ser | Phe | Asp |
|     |     |     | 180 |     |     |     |     | 185 |

( 2 ) INFORMATION FOR SEQ ID NO: 4:

( i ) SEQUENCE CHARACTERISTICS:
        ( A ) LENGTH: 122
        ( B ) TYPE: amino acid
        ( C ) STRANDEDNESS:
        ( D ) TOPOLOGY: linear ( x i ) SEQUENCE DESCRIPTION: SEQ ID NO: 4:

| Cys | Ala | Thr | Cys | Ser | Gln | Pro | Ile | Leu | Asp | Arg | Ile | Leu | Arg | Ala | Met |
| 1   |     |     |     | 5   |     |     |     |     | 10  |     |     |     |     | 15  |     |

| Gly | Lys | Ala | Tyr | His | Pro | Gly | Cys | Phe | Thr | Cys | Val | Val | Cys | His | Arg |
|     |     |     | 20  |     |     |     |     | 25  |     |     |     |     | 30  |     |     |

| Gly | Leu | Asp | Gly | Ile | Pro | Phe | Thr | Val | Asp | Ala | Thr | Ser | Gln | Ile | His |
|     |     | 35  |     |     |     |     | 40  |     |     |     |     | 45  |     |     |     |

| Cys | Ile | Glu | Asp | Phe | His | Arg | Lys | Phe | Ala | Pro | Arg | Cys | Ser | Val | Cys |
|     | 50  |     |     |     |     | 55  |     |     |     |     | 60  |     |     |     |     |

| Gly | Gly | Ala | Ile | Met | Pro | Glu | Pro | Gly | Gln | Glu | Glu | Thr | Val | Arg | Ile |
| 65  |     |     |     |     | 70  |     |     |     |     | 75  |     |     |     |     | 80  |

| Val | Ala | Leu | Asp | Arg | Ser | Phe | His | Ile | Gly | Cys | Tyr | Lys | Cys | Glu | Glu |
|     |     |     |     | 85  |     |     |     |     | 90  |     |     |     |     | 95  |     |

| Cys | Gly | Leu | Leu | Leu | Ser | Ser | Glu | Gly | Glu | Cys | Gln | Gly | Cys | Tyr | Pro |
|     |     |     | 100 |     |     |     |     | 105 |     |     |     |     | 110 |     |     |

| Leu | Asp | Gly | His | Ile | Leu | Cys | Lys | Ala | Cys |
|     |     | 115 |     |     |     |     | 120 |     |     |

( 2 ) INFORMATION FOR SEQ ID NO: 5:

( i ) SEQUENCE CHARACTERISTICS:
        ( A ) LENGTH: 114
        ( B ) TYPE: amino acid
        ( C ) STRANDEDNESS:
        ( D ) TOPOLOGY: linear ( x i ) SEQUENCE DESCRIPTION: SEQ ID NO: 5:

| Cys | Ala | Ala | Cys | Ala | Gln | Pro | Ile | Leu | Asp | Arg | Tyr | Val | Phe | Thr | Val |
| 1   |     |     |     | 5   |     |     |     |     | 10  |     |     |     |     | 15  |     |

| Leu | Gly | Lys | Cys | Trp | His | Gln | Ser | Cys | Leu | Arg | Cys | Cys | Asp | Cys | Arg |
|     |     |     | 20  |     |     |     |     | 25  |     |     |     |     | 30  |     |     |

-continued

```
Ala  Pro  Met  Ser  Met  Thr  Cys  Phe  Ser  Arg  Asp  Gly  Leu  Ile  Leu  Cys
          35                       40                      45

Lys  Thr  Asp  Phe  Ser  Arg  Arg  Tyr  Ser  Gln  Arg  Cys  Ala  Gly  Cys  Asp
     50                       55                      60

Gly  Lys  Leu  Glu  Lys  Glu  Asp  Leu  Val  Arg  Arg  Ala  Arg  Asp  Lys  Val
65                       70                      75                           80

Phe  His  Ile  Arg  Cys  Phe  Gln  Cys  Ser  Val  Cys  Gln  Arg  Leu  Leu  Asp
                    85                       90                           95

Thr  Gly  Asp  Gln  Leu  Tyr  Ile  Met  Glu  Gly  Asn  Arg  Phe  Val  Cys  Gln
               100                      105                      110

Ser  Asp
```

( 2 ) INFORMATION FOR SEQ ID NO: 6:

( i ) SEQUENCE CHARACTERISTICS:
    ( A ) LENGTH: 495
    ( B ) TYPE: nucleic acid
    ( C ) STRANDEDNESS: double
    ( D ) TOPOLOGY: linear ( x i ) SEQUENCE DESCRIPTION: SEQ ID NO: 6:

```
AAC  CCA  ATT  CTT  ACC  AGT  TTG  TTG  CAA  ATC  ACA  GGG  AAC  NGG  GGG  TCT        48
Asn  Pro  Ile  Leu  Thr  Ser  Leu  Leu  Gln  Ile  Thr  Gly  Asn  Xaa  Gly  Ser
1                        5                        10                      15

ACC  ATT  GGC  TCG  AGT  CCG  ACC  CCT  CCT  CAT  CAC  ACG  CCG  CCA  CCT  GTC        96
Thr  Ile  Gly  Ser  Ser  Pro  Thr  Pro  Pro  His  His  Thr  Pro  Pro  Pro  Val
                    20                       25                      30

TCT  TCG  ATG  GCC  GGC  AAC  ACC  AAG  AAC  CAC  CCG  ATG  CTC  ATG  AAC  CTT       144
Ser  Ser  Met  Ala  Gly  Asn  Thr  Lys  Asn  His  Pro  Met  Leu  Met  Asn  Leu
          35                       40                      45

CTT  AAA  GAT  AAT  CCT  GCC  CAG  GAT  TTC  TCA  ACC  CTT  TAT  GGA  AGC  AGC       192
Leu  Lys  Asp  Asn  Pro  Ala  Gln  Asp  Phe  Ser  Thr  Leu  Tyr  Gly  Ser  Ser
     50                       55                      60

CCT  TTA  GAA  AGG  CAG  AAC  TCC  TCT  TTC  GGC  TCA  CCC  CGC  ATG  GAA  ATA       240
Pro  Leu  Glu  Arg  Gln  Asn  Ser  Ser  Phe  Gly  Ser  Pro  Arg  Met  Glu  Ile
65                       70                      75                           80

TGC  TCG  GGG  AGC  AAC  AAG  ACC  AAG  AAA  AAG  AAG  TCA  TCA  AGA  TTA  CCA       288
Cys  Ser  Gly  Ser  Asn  Lys  Thr  Lys  Lys  Lys  Lys  Ser  Ser  Arg  Leu  Pro
                    85                       90                           95

CCT  GAG  AAA  CCA  AAA  CAA  CGC  GAG  GAT  ATA  ATT  GCC  AAA  ACC  AGG  CTT       336
Pro  Glu  Lys  Pro  Lys  Gln  Arg  Glu  Asp  Ile  Ile  Ala  Lys  Thr  Arg  Leu
               100                      105                      110

GAG  GTT  GGT  GAC  TCT  TGA  AAG  ATT  TTC  TTT  CTT  CAG  GCC  TAG  ATC  AGA       384
Glu  Val  Gly  Asp  Ser       Lys  Ile  Phe  Phe  Leu  Gln  Ala       Ile  Arg
               115                      120                      125

AAA  TTA  AGT  GCA  GCA  ATA  TCA  TGA  ATT  CTC  AGA  AGC  CCT  TTC  AGG  GAG       432
Lys  Leu  Ser  Ala  Ala  Ile  Ser       Ile  Leu  Arg  Ser  Pro  Phe  Arg  Glu
     130                      135                      140

CCA  GTG  AGT  CAT  ACA  GTA  TCC  ACA  GTT  GAG  TCA  CTT  AAA  GAT  GTC  AGT       480
Pro  Val  Ser  His  Thr  Val  Ser  Thr  Val  Glu  Ser  Leu  Lys  Asp  Val  Ser
145                      150                      155                          160

ATA  CGA  AAC  ATT  ATT                                                             495
Ile  Arg  Asn  Ile  Ile
                    165
```

( 2 ) INFORMATION FOR SEQ ID NO: 7:

( i ) SEQUENCE CHARACTERISTICS:
    ( A ) LENGTH: 885
    ( B ) TYPE: nucleic acid
    ( C ) STRANDEDNESS: double
    ( D ) TOPOLOGY: linear ( x i ) SEQUENCE DESCRIPTION: SEQ ID NO: 7:

```
CTC AAA TGT AGC ACC GTC GTC TGC GTG ATC TGC TTG GAG AAG CCC AAA      48
Leu Lys Cys Ser Thr Val Val Cys Val Ile Cys Leu Glu Lys Pro Lys
1                5                   10                  15

TAC CGC TGT CCA GCC TGC CGC GTG CCC TAC TGC TCG GTA GTC TGC TTC      96
Tyr Arg Cys Pro Ala Cys Arg Val Pro Tyr Cys Ser Val Val Cys Phe
                20              25                  30

CGG AAG CAC AAA GAA CAG TGC AAC CCT GAA ACT CGT CCT GTT GAG AAA     144
Arg Lys His Lys Glu Gln Cys Asn Pro Glu Thr Arg Pro Val Glu Lys
            35              40                  45

AAA ATA AGA TCA GCT CTT CCT ACC AAA ACC GTA AAG CCT GTG GAA AAC     192
Lys Ile Arg Ser Ala Leu Pro Thr Lys Thr Val Lys Pro Val Glu Asn
        50              55                  60

AAA GAT GAT GAT GAC TCT ATA GCT GAT TTT CTC AAT AGT GAT GAG GAA     240
Lys Asp Asp Asp Asp Ser Ile Ala Asp Phe Leu Asn Ser Asp Glu Glu
65              70                  75                      80

GAA GAC AGA GTT TCT TTG CAG AAT TTA AAG AAT TTA GGG GAA TCT GCA     288
Glu Asp Arg Val Ser Leu Gln Asn Leu Lys Asn Leu Gly Glu Ser Ala
                85                  90                  95

ACA TTA AGA AGC TTA TTG CTC AAT CCA CAC CTC AGG CAG TTG ATG GTC     336
Thr Leu Arg Ser Leu Leu Leu Asn Pro His Leu Arg Gln Leu Met Val
            100                 105                 110

AAC CTC GAT CAG GGA GAA GAC AAA GCA AAG CTC ATG AGA GCT TAC ATG     384
Asn Leu Asp Gln Gly Glu Asp Lys Ala Lys Leu Met Arg Ala Tyr Met
        115                 120                 125

CAA GAG CCT TTG TTT GTG GAG TTT GCA GAC TGT TGT TTA GGA ATT GTG     432
Gln Glu Pro Leu Phe Val Glu Phe Ala Asp Cys Cys Leu Gly Ile Val
130                 135                 140

GAG CCA TCC CAG AAT GAG GAG TCT TAA GAT GGA TTA TTG TGC TGC TTG     480
Glu Pro Ser Gln Asn Glu Glu Ser     Asp Gly Leu Leu Cys Cys Leu
145                 150                 155                 160

CTC AAG CGT GTG CTT GAC TCC TGG AAC CTG CCT GCT CCC TCT CCC AGA     528
Leu Lys Arg Val Leu Asp Ser Trp Asn Leu Pro Ala Pro Ser Pro Arg
                165                 170                 175

CCA GCT AGT TTG GGG CTG GGG AGC TCA GGC AAA AGA GGT TTC CAG GAT     576
Pro Ala Ser Leu Gly Leu Gly Ser Ser Gly Lys Arg Gly Phe Gln Asp
            180                 185                 190

GCA GAT TAG GTC ATG CAG GCC TTT ACC GGC ATT GAT GTG GCT CAT GTT     624
Ala Asp     Val Met Gln Ala Phe Thr Gly Ile Asp Val Ala His Val
        195                 200                 205

TCA GGC AGA CTT GGG GTC CTT AAG GTG GCA AGT CCT TTA TGG AGA GAA     672
Ser Gly Arg Leu Gly Val Leu Lys Val Ala Ser Pro Leu Trp Arg Glu
210                 215                 220

AAC TTG ACA TTC AGA TGA TTG TTT TTA AAT GTT TTA CTT TTG GTA CAG     720
Asn Leu Thr Phe Arg     Leu Phe Leu Asn Val Leu Leu Leu Val Gln
225                 230                 235                 240

TTG ATA GAC ATC ATA AAC GAT ATC AAG CTT ACA CTT CAT ATG GAG TTA     768
Leu Ile Asp Ile Ile Asn Asp Ile Lys Leu Thr Leu His Met Glu Leu
                245                 250                 255

AAC TTG GTC AGT GTT AAT AAA ATC AAA ACG TGA TTC TAC TGT ACA TTG     816
Asn Leu Val Ser Val Asn Lys Ile Lys Thr     Phe Tyr Cys Thr Leu
            260                 265                 270

CAT TAT TCA TAA TTT AAT TGT TTG AAA TTA CAT TAA ATA AAT CAA CTA     864
His Tyr Ser     Phe Asn Cys Leu Lys Leu His     Ile Asn Gln Leu
        275                 280                 285

ATT AAA AAA AAA AAA AAA AAA                                         885
Ile Lys Lys Lys Lys Lys Lys
290                 295
```

( 2 ) INFORMATION FOR SEQ ID NO: 8:

( i ) SEQUENCE CHARACTERISTICS:
        ( A ) LENGTH: 201
        ( B ) TYPE: nucleic acid
        ( C ) STRANDEDNESS: double
        ( D ) TOPOLOGY: linear ( x i ) SEQUENCE DESCRIPTION: SEQ ID NO: 8:

```
TCG  CTC  GTG  CTC  GCC  CGC  GCC  TGG  CCT  ACC  GCG  GCA  CTC  CCG  GCT  GCA    48
Ser  Leu  Val  Leu  Ala  Arg  Ala  Trp  Pro  Thr  Ala  Ala  Leu  Pro  Ala  Ala
1                        5                        10                       15

CGC  TCT  GCT  TGG  CCT  CGC  ATG  CCG  GTG  GAC  CTC  AGC  AAG  TGG  TCC  GGG    96
Arg  Ser  Ala  Trp  Pro  Arg  Met  Pro  Val  Asp  Leu  Ser  Lys  Trp  Ser  Gly
               20                        25                       30

CCC  TTG  AGC  CTG  CAA  GAA  GTG  GAC  GAG  CAG  CCG  CAG  CAC  CCG  CTG  CAT   144
Pro  Leu  Ser  Leu  Gln  Glu  Val  Asp  Glu  Gln  Pro  Gln  His  Pro  Leu  His
               35                        40                       45

GTC  ACC  TAC  GCC  GGG  GCG  CGT  GGA  CGA  GCT  GGG  CAA  CGT  GCT  GAC  GCC   192
Val  Thr  Tyr  Ala  Gly  Ala  Arg  Gly  Arg  Ala  Gly  Gln  Arg  Ala  Asp  Ala
          50                        55                       60

CAC  CCA  GGT                                                                    201
His  Pro  Gly
65
```

( 2 ) INFORMATION FOR SEQ ID NO: 9:

( i ) SEQUENCE CHARACTERISTICS:
        ( A ) LENGTH: 237
        ( B ) TYPE: nucleic acid
        ( C ) STRANDEDNESS: double
        ( D ) TOPOLOGY: linear ( x i ) SEQUENCE DESCRIPTION: SEQ ID NO: 9:

```
TCT  CAA  GAG  ACT  GAA  CAG  AGA  TGT  GAA  TCT  CTG  AAC  ACA  AGA  ACA  GTT    48
Ser  Gln  Glu  Thr  Glu  Gln  Arg  Cys  Glu  Ser  Leu  Asn  Thr  Arg  Thr  Val
1                        5                        10                       15

TAT  TTT  TCT  GAA  CAG  TGG  GTA  TCT  TCC  TTA  AAT  GAA  AGG  GAA  CAG  GAA    96
Tyr  Phe  Ser  Glu  Gln  Trp  Val  Ser  Ser  Leu  Asn  Glu  Arg  Glu  Gln  Glu
               20                        25                       30

CTT  CAC  AAC  TTA  TTG  GAG  GTT  GTA  AGC  CAA  TGT  TGT  GAG  GCT  TCA  AGT   144
Leu  His  Asn  Leu  Leu  Glu  Val  Val  Ser  Gln  Cys  Cys  Glu  Ala  Ser  Ser
               35                        40                       45

TCA  GAC  ATC  ACT  GAG  AAA  TCA  GAT  GGA  CGT  AAG  GCA  GCT  CAT  GAG  AAA   192
Ser  Asp  Ile  Thr  Glu  Lys  Ser  Asp  Gly  Arg  Lys  Ala  Ala  His  Glu  Lys
          50                        55                       60

CAG  CAT  AAC  ATT  TTT  CTT  GAT  CAG  ATG  ACT  ATT  GAT  GAA  GAT  AAA        237
Gln  His  Asn  Ile  Phe  Leu  Asp  Gln  Met  Thr  Ile  Asp  Glu  Asp  Lys
65                       70                       75
```

( 2 ) INFORMATION FOR SEQ ID NO: 10:

( i ) SEQUENCE CHARACTERISTICS:
        ( A ) LENGTH: 126
        ( B ) TYPE: nucleic acid
        ( C ) STRANDEDNESS: double
        ( D ) TOPOLOGY: linear ( x i ) SEQUENCE DESCRIPTION: SEQ ID NO: 10:

```
GAA  GAT  CAA  GAT  ACC  TCA  AAG  AAT  TCT  AAG  CTA  AAC  TCA  CAC  CAG  AAA    48
Glu  Asp  Gln  Asp  Thr  Ser  Lys  Asn  Ser  Lys  Leu  Asn  Ser  His  Gln  Lys
1                        5                        10                       15

GTA  ACA  CTT  CTT  CAA  TTG  CTA  CTT  GGC  CAT  AAG  AAT  GAA  GAA  AAT  GTA    96
Val  Thr  Leu  Leu  Gln  Leu  Leu  Leu  Gly  His  Lys  Asn  Glu  Glu  Asn  Val
               20                        25                       30
```

```
GAA AAA AAC ACC AGC TGC AGG TGA TGA TGA                                         126
Glu Lys Asn Thr Ser Cys Arg
         35
```

(2) INFORMATION FOR SEQ ID NO: 11:

(i) SEQUENCE CHARACTERISTICS:
        (A) LENGTH: 570
        (B) TYPE: nucleic acid
        (C) STRANDEDNESS: double
        (D) TOPOLOGY: linear (xi) SEQUENCE DESCRIPTION: SEQ ID NO: 11:

```
CTT ACC TTA GAA AAC CAA ATT AAA GAA GAA AGA GAA CAA GAC AAC TCT                 48
Leu Thr Leu Glu Asn Gln Ile Lys Glu Glu Arg Glu Gln Asp Asn Ser
1               5                   10                  15

GAA TCT CCA AAT GGC AGA ACA TCA CCT CTT GTG TCC CAG AAT AAT GAA                 96
Glu Ser Pro Asn Gly Arg Thr Ser Pro Leu Val Ser Gln Asn Asn Glu
                20                  25                  30

CAA GGC TCA ACC TTA CGG GAT TTG CTG ACT ACA ACA GCT GGA AAG CTA                144
Gln Gly Ser Thr Leu Arg Asp Leu Leu Thr Thr Thr Ala Gly Lys Leu
            35                  40                  45

CGT GTG GGG TCT ACA GAT GCT GGC ATT GCC TTT GCC CCA GTA TAT GCA                192
Arg Val Gly Ser Thr Asp Ala Gly Ile Ala Phe Ala Pro Val Tyr Ala
        50                  55                  60

ATG GGA GCC CCA AGT AGC AAA AGT GGA CGG ACT ATG CCT AAC ATT CTT                240
Met Gly Ala Pro Ser Ser Lys Ser Gly Arg Thr Met Pro Asn Ile Leu
65                  70                  75                  80

GAT GAC ATA ATT GCT TCA GTT GTT GAA AAC AAA ATT CCA CCA AGT AAA                288
Asp Asp Ile Ile Ala Ser Val Val Glu Asn Lys Ile Pro Pro Ser Lys
                85                  90                  95

ACC TCC AAG ATA AAT GTA AAA CCA GAG CTT AAA GAA GAG CCT GAA GAA                336
Thr Ser Lys Ile Asn Val Lys Pro Glu Leu Lys Glu Glu Pro Glu Glu
            100                 105                 110

AGC ATA ATA TCT GCA GTG GAT GAA AAT AAT AAA TTA TAC AGT GAT ATA                384
Ser Ile Ile Ser Ala Val Asp Glu Asn Asn Lys Leu Tyr Ser Asp Ile
        115                 120                 125

CCA CAT TCT TGG ATC TGT GAG AAG CAT ATT TTA TGG CTT AGG ATT ATA                432
Pro His Ser Trp Ile Cys Glu Lys His Ile Leu Trp Leu Arg Ile Ile
130                 135                 140

AGA ATA GCA GTA ATT GGA AGC TTT TCA AAG AAT GTT GGA AAC AAG GAC                480
Arg Ile Ala Val Ile Gly Ser Phe Ser Lys Asn Val Gly Asn Lys Asp
145                 150                 155                 160

AGC CTG CAG TGG TTT CTG GTG TGC ATA AGA AAA TGA ACA TTA GCC TAT                528
Ser Leu Gln Trp Phe Leu Val Cys Ile Arg Lys     Thr Leu Ala Tyr
                165                 170                 175

GGA AGG CGG AAT CAA TTA GTC TTG ATT TTG GAG ACC ACC AAG                        570
Gly Arg Arg Asn Gln Leu Val Leu Ile Leu Glu Thr Thr Lys
            180                 185                 190
```

(2) INFORMATION FOR SEQ ID NO: 12:

(i) SEQUENCE CHARACTERISTICS:
        (A) LENGTH: 624
        (B) TYPE: nucleic acid
        (C) STRANDEDNESS: double
        (D) TOPOLOGY: linear (xi) SEQUENCE DESCRIPTION: SEQ ID NO: 12:

```
AAC CAT ACC CCT GGC GCC TTG TAC CCC GAT TCC GAC TTG GAG AAG GAA                 48
Asn His Thr Pro Gly Ala Leu Tyr Pro Asp Ser Asp Leu Glu Lys Glu
1               5                   10                  15

GAA GAG GAG AGT GAG GAG GAC TGG AAG CTG CAG CTG GAG GCT GAA AAC                 96
Glu Glu Glu Ser Glu Glu Asp Trp Lys Leu Gln Leu Glu Ala Glu Asn
```

```
                    20                              25                              30
TAC  GAG  GGC  CAC  ACC  CCA  CTC  CAC  GTG  GCC  GTT  ATC  CAC  AAA  GAT  GTG        144
Tyr  Glu  Gly  His  Thr  Pro  Leu  His  Val  Ala  Val  Ile  His  Lys  Asp  Val
          35                       40                       45

GAG  ATG  GTC  CGG  CTG  CTC  CGA  GAT  GCT  GGA  GCT  GAC  CTT  GAC  AAA  CCG        192
Glu  Met  Val  Arg  Leu  Leu  Arg  Asp  Ala  Gly  Ala  Asp  Leu  Asp  Lys  Pro
     50                            55                       60

GAG  CCC  ACG  TGC  GGC  CGG  AGC  CCC  TTC  ATT  TGG  CAG  TGG  AGG  CCA  GGC        240
Glu  Pro  Thr  Cys  Gly  Arg  Ser  Pro  Phe  Ile  Trp  Gln  Trp  Arg  Pro  Gly
65                       70                       75                       80

AGC  CGA  TGT  GCT  GGA  GCT  TCT  CTG  AGG  GCA  GGC  GCG  AAC  CCT  GCT  GCC        288
Ser  Arg  Cys  Ala  Gly  Ala  Ser  Leu  Arg  Ala  Gly  Ala  Asn  Pro  Ala  Ala
                    85                       90                       95

CGC  ATG  TAC  GGT  GGC  CGC  ACC  CCA  CTC  GGC  AGT  GCC  ATG  CTC  CGG  CCC        336
Arg  Met  Tyr  Gly  Gly  Arg  Thr  Pro  Leu  Gly  Ser  Ala  Met  Leu  Arg  Pro
               100                      105                      110

AAC  CCC  ATC  CTC  GCC  CGC  CTC  CTC  CGT  GCA  CAC  GGA  GCC  CCT  GAG  CCC        384
Asn  Pro  Ile  Leu  Ala  Arg  Leu  Leu  Arg  Ala  His  Gly  Ala  Pro  Glu  Pro
          115                      120                      125

GAG  GGG  AAG  GAC  GAG  AAA  TCC  GGC  CCC  TGC  AGC  AGC  AGT  AGC  GAG  CAC        432
Glu  Gly  Lys  Asp  Glu  Lys  Ser  Gly  Pro  Cys  Ser  Ser  Ser  Ser  Glu  His
     130                      135                      140

GAC  NAG  AGA  NGA  CGA  GGG  CGA  TGA       ATA  CGA  CGA  CAT  TGT  GGT  TCA  CAG   480
Asp  Xaa  Arg  Xaa  Arg  Gly  Arg            Ile  Arg  Arg  His  Cys  Gly  Ser  Gln
145                           150                     155                      160

CAG  CCG  CAG  CCA  AAC  CCG  GCT  GCC  TCC  CAC  CCC  AGC  CTC  AAA  ACC  TCT        528
Gln  Pro  Gln  Pro  Asn  Pro  Ala  Ala  Ser  His  Pro  Ser  Leu  Lys  Thr  Ser
                    165                      170                      175

TCC  TGA  CGA  CCC  CCG  CCC  CGT  GTG  ATT  TGT  TTC  ATT  GTT  AAT  ATA  ATT        576
Ser       Arg  Pro  Pro  Pro  Arg  Val  Ile  Cys  Phe  Ile  Val  Asn  Ile  Ile
               180                      185                      190

TCC  AGT  TTA  ATA  AAC  AAA  ACC  CTA  GTT  CTG  ACA  ACC  AGA  AAA  AAA  AAA        624
Ser  Ser  Leu  Ile  Asn  Lys  Thr  Leu  Val  Leu  Thr  Thr  Arg  Lys  Lys  Lys
               195                      200                      205
```

( 2 ) INFORMATION FOR SEQ ID NO: 13:

( i ) SEQUENCE CHARACTERISTICS:
        ( A ) LENGTH: 99
        ( B ) TYPE: nucleic acid
        ( C ) STRANDEDNESS: double
        ( D ) TOPOLOGY: linear ( x i ) SEQUENCE DESCRIPTION: SEQ ID NO: 13:

```
AGA  CAC  CCG  CTG  ATC  AGA  GAC  ATG  CTT  CGA  CGA  ATT  AAG  GAA  GAA  GAG         48
Arg  His  Pro  Leu  Ile  Arg  Asp  Met  Leu  Arg  Arg  Ile  Lys  Glu  Glu  Glu
1                        5                        10                       15

GAT  CTG  GGT  AAA  AGT  AGA  GAA  GGA  TCA  AGG  ACG  GAT  GAT  GAA  GTA  GTA         96
Asp  Leu  Gly  Lys  Ser  Arg  Glu  Gly  Ser  Arg  Thr  Asp  Asp  Glu  Val  Val
               20                       25                       30

CAG                                                                                    99
Gln
```

( 2 ) INFORMATION FOR SEQ ID NO: 14:

( i ) SEQUENCE CHARACTERISTICS:
        ( A ) LENGTH: 216
        ( B ) TYPE: nucleic acid
        ( C ) STRANDEDNESS: double
        ( D ) TOPOLOGY: linear ( x i ) SEQUENCE DESCRIPTION: SEQ ID NO: 14:

```
CAG  GTG  GAA  GAA  AAC  ACC  CCG  TAC  TGG  CAG  GCA  TGG  AGC  CAA  CAA  GGA         48
```

|  |  |  |  |  |  |  |  |  |  |  |  |  |  |  |  |
|---|---|---|---|---|---|---|---|---|---|---|---|---|---|---|---|
| Gln | Val | Glu | Glu | Asn | Thr | Pro | Tyr | Trp | Gln | Ala | Trp | Ser | Gln | Gln | Gly |
| 1 |  |  |  | 5 |  |  |  |  | 10 |  |  |  |  | 15 |  |

| GAA | CCT | GGA | GCT | CAA | CGG | CAG | CAT | CCT | GAG | TGC | GAG | AAC | TTT | CAA | AGG | 96 |
|---|---|---|---|---|---|---|---|---|---|---|---|---|---|---|---|---|
| Glu | Pro | Gly | Ala | Gln | Arg | Gln | His | Pro | Glu | Cys | Glu | Asn | Phe | Gln | Arg |  |
|  |  |  | 20 |  |  |  | 25 |  |  |  |  |  | 30 |  |  |  |

| CTT | CCA | AAT | CTG | ATG | CTA | CTT | CTG | GAA | TCC | TCA | ATT | CAA | CCA | ACA | TCC | 144 |
|---|---|---|---|---|---|---|---|---|---|---|---|---|---|---|---|---|
| Leu | Pro | Asn | Leu | Met | Leu | Leu | Leu | Glu | Ser | Ser | Ile | Gln | Pro | Thr | Ser |  |
|  |  | 35 |  |  |  |  | 40 |  |  |  |  | 45 |  |  |  |  |

| AGT | CCT | GAG | AAG | CCC | TGA | TCA | GTC | AAC | CAG | CTG | TGG | CTT | CCT | GTG | CCT | 192 |
|---|---|---|---|---|---|---|---|---|---|---|---|---|---|---|---|---|
| Ser | Pro | Glu | Lys | Pro |  | Ser | Val | Asn | Gln | Leu | Trp | Leu | Pro | Val | Pro |  |
|  | 50 |  |  |  |  | 55 |  |  |  |  | 60 |  |  |  |  |  |

| AGA | CTG | GAC | CTA | ATT | ATA | TGG | GGG |  |  |  |  |  |  |  |  | 216 |
|---|---|---|---|---|---|---|---|---|---|---|---|---|---|---|---|---|
| Arg | Leu | Asp | Leu | Ile | Ile | Trp | Gly |  |  |  |  |  |  |  |  |  |
| 65 |  |  |  |  | 70 |  |  |  |  |  |  |  |  |  |  |  |

( 2 ) INFORMATION FOR SEQ ID NO: 15:

( i ) SEQUENCE CHARACTERISTICS:
        ( A ) LENGTH: 634
        ( B ) TYPE: nucleic acid
        ( C ) STRANDEDNESS: double
        ( D ) TOPOLOGY: linear ( x i ) SEQUENCE DESCRIPTION: SEQ ID NO: 15:

| TGC | CGC | TGC | AGC | AGC | GCA | GTT | CCA | GTC | CGT | TGC | TTT | ACT | TTT | TGC | TTC | 48 |
|---|---|---|---|---|---|---|---|---|---|---|---|---|---|---|---|---|
| Cys | Arg | Cys | Ser | Ser | Ala | Val | Pro | Val | Arg | Cys | Phe | Thr | Phe | Cys | Phe |  |
| 1 |  |  |  | 5 |  |  |  |  | 10 |  |  |  |  | 15 |  |  |

| ACC | GAC | ATA | GTC | ATT | ATG | CCG | AAG | AGA | AAG | TCT | CCA | GAG | AAT | ACA | GAG | 96 |
|---|---|---|---|---|---|---|---|---|---|---|---|---|---|---|---|---|
| Thr | Asp | Ile | Val | Ile | Met | Pro | Lys | Arg | Lys | Ser | Pro | Glu | Asn | Thr | Glu |  |
|  |  |  | 20 |  |  |  | 25 |  |  |  |  |  | 30 |  |  |  |

| GGC | AAA | GAT | GGA | TCC | AAA | GTA | ACT | AAA | CAG | GAG | CCC | ACA | AGA | CGG | TCT | 144 |
|---|---|---|---|---|---|---|---|---|---|---|---|---|---|---|---|---|
| Gly | Lys | Asp | Gly | Ser | Lys | Val | Thr | Lys | Gln | Glu | Pro | Thr | Arg | Arg | Ser |  |
|  |  | 35 |  |  |  |  | 40 |  |  |  |  | 45 |  |  |  |  |

| GCC | AGA | TTG | TCA | GCG | AAA | CCT | GCT | CCA | CCA | AAA | CCT | GAA | CCC | AAA | CCA | 192 |
|---|---|---|---|---|---|---|---|---|---|---|---|---|---|---|---|---|
| Ala | Arg | Leu | Ser | Ala | Lys | Pro | Ala | Pro | Pro | Lys | Pro | Glu | Pro | Lys | Pro |  |
|  | 50 |  |  |  |  | 55 |  |  |  |  | 60 |  |  |  |  |  |

| AGA | AAA | ACA | TCT | GCT | AAG | AAA | GAA | CCT | GGA | GCA | AAG | ATT | AGC | AGA | GGT | 240 |
|---|---|---|---|---|---|---|---|---|---|---|---|---|---|---|---|---|
| Arg | Lys | Thr | Ser | Ala | Lys | Lys | Glu | Pro | Gly | Ala | Lys | Ile | Ser | Arg | Gly |  |
| 65 |  |  |  |  | 70 |  |  |  |  | 75 |  |  |  |  | 80 |  |

| GCT | AAA | GGG | AGG | AAG | GAG | GAA | AAG | CAG | GAA | GCT | GGA | AAG | GAA | GGT | ACT | 288 |
|---|---|---|---|---|---|---|---|---|---|---|---|---|---|---|---|---|
| Ala | Lys | Gly | Arg | Lys | Glu | Glu | Lys | Gln | Glu | Ala | Gly | Lys | Glu | Gly | Thr |  |
|  |  |  |  | 85 |  |  |  |  | 90 |  |  |  |  | 95 |  |  |

| GCA | CCA | TCT | GAA | AAT | GGT | GAA | ACT | AAA | GCT | GAA | GAG | GCA | CAG | AAA | ACT | 336 |
|---|---|---|---|---|---|---|---|---|---|---|---|---|---|---|---|---|
| Ala | Pro | Ser | Glu | Asn | Gly | Glu | Thr | Lys | Ala | Glu | Glu | Ala | Gln | Lys | Thr |  |
|  |  |  |  | 100 |  |  |  |  | 105 |  |  |  |  | 110 |  |  |

| GAA | TCT | GTA | GAT | AAC | GAG | GGA | GAA | TGA | ATT | GTC | ATG | AAA | AAT | TGG | GGT | 384 |
|---|---|---|---|---|---|---|---|---|---|---|---|---|---|---|---|---|
| Glu | Ser | Val | Asp | Asn | Glu | Gly | Glu |  | Ile | Val | Met | Lys | Asn | Trp | Gly |  |
|  |  | 115 |  |  |  |  | 120 |  |  |  |  | 125 |  |  |  |  |

| TGA | TTT | TAT | GTA | TCT | CTT | GGG | ACA | ACT | TTT | AAA | AGC | TAT | TTT | TAC | CAA | 432 |
|---|---|---|---|---|---|---|---|---|---|---|---|---|---|---|---|---|
|  | Phe | Tyr | Val | Ser | Leu | Gly | Thr | Thr | Phe | Lys | Ser | Tyr | Phe | Tyr | Gln |  |
|  | 130 |  |  |  |  | 135 |  |  |  |  | 140 |  |  |  |  |  |

| GTA | TTT | TGT | AAA | TGC | TAA | TTT | TTT | AGG | ACT | CTA | CTA | GTT | GGC | ATA | CGA | 480 |
|---|---|---|---|---|---|---|---|---|---|---|---|---|---|---|---|---|
| Val | Phe | Cys | Lys | Cys |  | Phe | Phe | Arg | Thr | Leu | Leu | Val | Gly | Ile | Arg |  |
| 145 |  |  |  |  | 150 |  |  |  |  | 155 |  |  |  |  | 160 |  |

| AAA | TAT | ATA | AGG | ATG | GAC | ATT | TAT | CGT | CTC | ATA | GTC | ATG | CTT | TTT | GGA | 528 |
|---|---|---|---|---|---|---|---|---|---|---|---|---|---|---|---|---|
| Lys | Tyr | Ile | Arg | Met | Asp | Ile | Tyr | Arg | Leu | Ile | Val | Met | Leu | Phe | Gly |  |
|  |  |  |  | 165 |  |  |  |  | 170 |  |  |  |  | 175 |  |  |

| ATT | TNN | NNN | NNN | NNN | NNN | NNN | NNN | NNN | NCA | GGA | AGT | TTG | CCC | CAA | 576 |
|---|---|---|---|---|---|---|---|---|---|---|---|---|---|---|---|
| Ile | Xaa | Xaa | Xaa | Xaa | Xaa | Xaa | Xaa | Xaa | Xaa | Gly | Ser | Leu | Pro | Gln |  |
|  |  |  | 180 |  |  |  |  | 185 |  |  |  | 190 |  |  |  |

| GAT | GCT | CAG | TGT | GCC | GTG | GGG | CCA | TAA | CTG | CCT | GAG | CCA | GGT | CAG | GAG | 624 |
|---|---|---|---|---|---|---|---|---|---|---|---|---|---|---|---|---|
| Asp | Ala | Gln | Cys | Ala | Val | Gly | Pro |  | Leu | Pro | Glu | Pro | Gly | Gln | Glu |  |

```
                    1 9 5                         2 0 0                              2 0 5

GAG  ACT  GCT  G                                                                                          6 3 4
Glu  Thr  Ala
     2 1 0
```

( 2 ) INFORMATION FOR SEQ ID NO: 16:

( i ) SEQUENCE CHARACTERISTICS:
        ( A ) LENGTH: 638
        ( B ) TYPE: nucleic acid
        ( C ) STRANDEDNESS: double
        ( D ) TOPOLOGY: linear ( x i ) SEQUENCE DESCRIPTION: SEQ ID NO: 16:

```
AAA  CAT  CCT  ATC  ATC  TGT  AGG  CTC  ATT  CAT  TTC  TCT  AAC  AGC  AGC  AGC       4 8
Lys  His  Pro  Ile  Ile  Cys  Arg  Leu  Ile  His  Phe  Ser  Asn  Ser  Ser  Ser
1                   5                        1 0                      1 5

AAC  AGC  GCA  TCA  CAG  GAC  ACC  AAG  GAG  AGC  TCT  GAA  GAG  CCT  CCC  TCA       9 6
Asn  Ser  Ala  Ser  Gln  Asp  Thr  Lys  Glu  Ser  Ser  Glu  Glu  Pro  Pro  Ser
               2 0                      2 5                      3 0

GAA  GAG  AGC  CAG  GAC  ACC  CCC  ATT  TAC  ACG  GAG  TTT  GAT  GAG  GAT  TTC      1 4 4
Glu  Glu  Ser  Gln  Asp  Thr  Pro  Ile  Tyr  Thr  Glu  Phe  Asp  Glu  Asp  Phe
          3 5                      4 0                           4 5

GAG  GAG  GAA  CCC  ACA  TCC  CCC  ATA  GGT  CAC  TGT  GTG  GCC  ATC  TAC  CAC      1 9 2
Glu  Glu  Glu  Pro  Thr  Ser  Pro  Ile  Gly  His  Cys  Val  Ala  Ile  Tyr  His
     5 0                           5 5                      6 0

TTT  GAA  GGG  TCC  AGC  GAG  GGC  ACT  ATC  TCT  ATG  GCC  GAG  GGT  GAA  GAC      2 4 0
Phe  Glu  Gly  Ser  Ser  Glu  Gly  Thr  Ile  Ser  Met  Ala  Glu  Gly  Glu  Asp
6 5                      7 0                      7 5                      8 0

CTC  AGT  CTT  ATG  GAA  GAA  GAC  AAA  GGG  GAC  GGC  TGG  ACC  CGG  GTC  AGG      2 8 8
Leu  Ser  Leu  Met  Glu  Glu  Asp  Lys  Gly  Asp  Gly  Trp  Thr  Arg  Val  Arg
               8 5                      9 0                      9 5

CGG  AAA  GAG  GGA  GGC  GAG  GGC  TAC  GTG  CCC  ACC  TCC  TAC  CTC  CGA  GTC      3 3 6
Arg  Lys  Glu  Gly  Gly  Glu  Gly  Tyr  Val  Pro  Thr  Ser  Tyr  Leu  Arg  Val
               1 0 0                     1 0 5                     1 1 0

ACG  CTC  AAT  TGA  ACC  CTG  CCA  GAG  ACG  GGA  AGA  GGG  GGG  CTG  TCG  GCT      3 8 4
Thr  Leu  Asn       Thr  Leu  Pro  Glu  Thr  Gly  Arg  Gly  Gly  Leu  Ser  Ala
          1 1 5                     1 2 0                     1 2 5

GCT  GCT  TCT  GGG  CCA  CGG  GGA  GCC  CCA  GGA  CCT  ATG  CAC  TTT  ATT  TCT      4 3 2
Ala  Ala  Ser  Gly  Pro  Arg  Gly  Ala  Pro  Gly  Pro  Met  His  Phe  Ile  Ser
          1 3 0                     1 3 5                     1 4 0

GAC  CCC  GTG  GCT  TCG  GCT  GAG  ACC  TGT  GTA  ACC  TGC  TGC  CCC  CTC  CAC      4 8 0
Asp  Pro  Val  Ala  Ser  Ala  Glu  Thr  Cys  Val  Thr  Cys  Cys  Pro  Leu  His
1 4 5                     1 5 0                     1 5 5                     1 6 0

CCC  CAA  CCC  AGT  CCT  ACC  TGT  CAC  ACC  GGA  CGG  ACC  CGC  TGT  GCC  TTC      5 2 8
Pro  Gln  Pro  Ser  Pro  Thr  Cys  His  Thr  Gly  Arg  Thr  Arg  Cys  Ala  Phe
               1 6 5                     1 7 0                     1 7 5

TAC  CAT  CGT  TCC  ACC  ATT  GAT  GTA  CAT  ACT  CAT  GTT  TTA  CAT  CTT  TTC      5 7 6
Tyr  His  Arg  Ser  Thr  Ile  Asp  Val  His  Thr  His  Val  Leu  His  Leu  Phe
               1 8 0                     1 8 5                     1 9 0

TTT  CTG  CGC  TCG  GCT  CCG  GCC  ATT  TTG  TTT  TAT  ACA  AAA  ATG  GGA  AAA      6 2 4
Phe  Leu  Arg  Ser  Ala  Pro  Ala  Ile  Leu  Phe  Tyr  Thr  Lys  Met  Gly  Lys
          1 9 5                     2 0 0                     2 0 5

AAA  AAA  AAA  AAA  AA                                                               6 3 8
Lys  Lys  Lys  Lys
     2 1 0
```

( 2 ) INFORMATION FOR SEQ ID NO: 17:

( i ) SEQUENCE CHARACTERISTICS:
        ( A ) LENGTH: 862
        ( B ) TYPE: nucleic acid
        ( C ) STRANDEDNESS: double ( D ) TOPOLOGY: linear ( x i ) SEQUENCE DESCRIPTION: SEQ ID NO: 17:

```
GGC  ACG  AGG  CGT  GAC  GTC  CGA  CAA  GAA  ATG  CTG  GAT  GAT  GTA  CAA  AAG     48
Gly  Thr  Arg  Arg  Asp  Val  Arg  Gln  Glu  Met  Leu  Asp  Asp  Val  Gln  Lys
1              5                        10                       15

AAA  TTG  ATG  AGC  TTA  GCA  AAC  AGC  TCA  GAA  GGA  AAA  GTA  GAC  AAA  GTC     96
Lys  Leu  Met  Ser  Leu  Ala  Asn  Ser  Ser  Glu  Gly  Lys  Val  Asp  Lys  Val
                20                       25                       30

CTA  ATG  AGA  AAC  CTC  TTC  ATT  GGT  CAT  TTC  CAC  ACA  CCG  AAA  AAT  CAG    144
Leu  Met  Arg  Asn  Leu  Phe  Ile  Gly  His  Phe  His  Thr  Pro  Lys  Asn  Gln
          35                       40                       45

CGT  CAT  GAA  GTG  TTA  CGG  TTA  ATG  GGG  AGC  ATC  CTG  GGC  GTC  AGA  AGG    192
Arg  His  Glu  Val  Leu  Arg  Leu  Met  Gly  Ser  Ile  Leu  Gly  Val  Arg  Arg
     50                       55                       60

GAG  GAG  ATG  GAG  CAG  TTG  TTT  CAT  GAC  GAT  CAG  GGC  AGT  GTT  ACC  AGG    240
Glu  Glu  Met  Glu  Gln  Leu  Phe  His  Asp  Asp  Gln  Gly  Ser  Val  Thr  Arg
65                       70                       75                       80

TGG  ATG  ACT  GGG  TGG  CTT  GGA  GGA  GGA  TCA  AAA  AGT  GTT  CCC  AAC  ACA    288
Trp  Met  Thr  Gly  Trp  Leu  Gly  Gly  Gly  Ser  Lys  Ser  Val  Pro  Asn  Thr
                85                       90                       95

CCT  TTG  AGA  CCA  AAT  CAG  CAA  TCT  GTG  GTT  AAT  AGT  TCT  TTT  TCA  GAA    336
Pro  Leu  Arg  Pro  Asn  Gln  Gln  Ser  Val  Val  Asn  Ser  Ser  Phe  Ser  Glu
          100                      105                      110

CTT  TTT  GTT  AAA  TTT  CTA  GAA  ACA  GAA  TCT  CAT  CCA  TCC  ATT  CCA  CCA    384
Leu  Phe  Val  Lys  Phe  Leu  Glu  Thr  Glu  Ser  His  Pro  Ser  Ile  Pro  Pro
     115                      120                      125

CCA  AAG  CTT  TCT  GTT  CAT  GAT  ATG  AAA  CCT  CTG  GAT  TCA  CCA  GGA  AGA    432
Pro  Lys  Leu  Ser  Val  His  Asp  Met  Lys  Pro  Leu  Asp  Ser  Pro  Gly  Arg
     130                      135                      140

AGA  AAA  AGA  GAT  ACA  AAT  GCA  CCA  GAA  AGT  TTT  AAA  GAT  ACA  GCA  GAA    480
Arg  Lys  Arg  Asp  Thr  Asn  Ala  Pro  Glu  Ser  Phe  Lys  Asp  Thr  Ala  Glu
145                      150                      155                      160

TCC  AGG  TCT  GGT  AGA  AGA  ACA  GAT  GTA  AAT  CCG  TTT  TTG  GCT  CCT  CGC    528
Ser  Arg  Ser  Gly  Arg  Arg  Thr  Asp  Val  Asn  Pro  Phe  Leu  Ala  Pro  Arg
                165                      170                      175

TCG  GCA  GCT  GTA  CCT  CTT  ATT  AAC  CCA  GCT  GGA  CTT  GGA  CCT  GGT  GGG    576
Ser  Ala  Ala  Val  Pro  Leu  Ile  Asn  Pro  Ala  Gly  Leu  Gly  Pro  Gly  Gly
          180                      185                      190

CCG  GGC  ATC  TTC  TTC  TGA  AAC  CCA  TCT  CAG  ATG  TTT  TGC  CCA  CAT  TTA    624
Pro  Gly  Ile  Phe  Phe       Asn  Pro  Ser  Gln  Met  Phe  Cys  Pro  His  Leu
     195                      200                      205

CAC  CTT  TGC  CAG  CGT  TAC  CTG  ACA  ACA  GTG  CTG  GGG  TTG  TGC  TGA  AAG    672
His  Leu  Cys  Gln  Arg  Tyr  Leu  Thr  Thr  Val  Leu  Gly  Leu  Cys       Lys
210                      215                      220

CCT  TTT  AAA  GCA  ATA  GAT  GAT  TCT  CAA  GCC  AGA  GAC  AAT  CTA  GCA  CTT    720
Pro  Phe  Lys  Ala  Ile  Asp  Asp  Ser  Gln  Ala  Arg  Asp  Asn  Leu  Ala  Leu
225                      230                      235                      240

TAA  AGA  AAC  CAT  GAA  CAC  TAT  ATG  TAT  GTA  CTT  TAT  CAC  AAA  GTG  GCC    768
     Arg  Asn  His  Glu  His  Tyr  Met  Tyr  Val  Leu  Tyr  His  Lys  Val  Ala
                    245                      250                      255

TTT  GGG  GAG  AAA  GTC  ATG  TAT  TTG  TTC  GCA  ATT  ATG  CTT  TCT  CTG  AAT    816
Phe  Gly  Glu  Lys  Val  Met  Tyr  Leu  Phe  Ala  Ile  Met  Leu  Ser  Leu  Asn
               260                      265                      270

TTA  ATA  AAA  ATA  TTC  CTA  ATG  CTT  TTA  GAA  AAA  AAA  AAA  AAA  AAA  A      862
Leu  Ile  Lys  Ile  Phe  Leu  Met  Leu  Leu  Glu  Lys  Lys  Lys  Lys  Lys
          275                      280                      285
```

( 2 ) INFORMATION FOR SEQ ID NO: 18:

( i ) SEQUENCE CHARACTERISTICS:

(A) LENGTH: 247
(B) TYPE: nucleic acid
(C) STRANDEDNESS: double
(D) TOPOLOGY: linear (xi) SEQUENCE DESCRIPTION: SEQ ID NO: 18:

| GGC | ACG | AGG | CGA | GTT | CTC | CCA | CCT | GAG | CAG | AAA | TAT | GAC | CAT | GCA | GCG | 48 |
| Gly | Thr | Arg | Arg | Val | Leu | Pro | Pro | Glu | Gln | Lys | Tyr | Asp | His | Ala | Ala | |
| 1 | | | | 5 | | | | | 10 | | | | | 15 | | |

| CAC | CAT | GAA | GCT | CTA | CCG | ACT | GCC | AGA | GAC | TCC | CAA | GAC | AGC | TGG | GCT | 96 |
| His | His | Glu | Ala | Leu | Pro | Thr | Ala | Arg | Asp | Ser | Gln | Asp | Ser | Trp | Ala | |
| | | | 20 | | | | | 25 | | | | | 30 | | | |

| GCG | ACC | AAT | GGA | AAC | AAA | GGA | CAT | TCC | AGT | AGT | GCA | CCA | GCT | CCT | CAC | 144 |
| Ala | Thr | Asn | Gly | Asn | Lys | Gly | His | Ser | Ser | Ser | Ala | Pro | Ala | Pro | His | |
| | | 35 | | | | | 40 | | | | | 45 | | | | |

| CAG | GTA | CTT | GAA | GCA | ATT | TCA | CCT | TAC | GCC | CGT | CAT | GAG | CCA | GGA | GGA | 192 |
| Gln | Val | Leu | Glu | Ala | Ile | Ser | Pro | Tyr | Ala | Arg | His | Glu | Pro | Gly | Gly | |
| | 50 | | | | | 55 | | | | | 60 | | | | | |

| GGT | GGA | GCA | CTG | GTT | CTA | CCC | CCA | GGA | GAA | TAT | CAT | CGA | CAC | TTT | CGT | 240 |
| Gly | Gly | Ala | Leu | Val | Leu | Pro | Pro | Gly | Glu | Tyr | His | Arg | His | Phe | Arg | |
| 65 | | | | | 70 | | | | | 75 | | | | | 80 | |

| GGT | GGA | G | | | | | | | | | | | | | | 247 |
| Gly | Gly | | | | | | | | | | | | | | | |

(2) INFORMATION FOR SEQ ID NO: 19:

(i) SEQUENCE CHARACTERISTICS:
(A) LENGTH: 102
(B) TYPE: nucleic acid
(C) STRANDEDNESS: double
(D) TOPOLOGY: linear (xi) SEQUENCE DESCRIPTION: SEQ ID NO: 19:

| AGG | GCG | CAC | CTG | GAG | CTG | TTC | TGG | TCT | AGA | GTG | AAT | ATC | CCC | AAG | GTG | 48 |
| Arg | Ala | His | Leu | Glu | Leu | Phe | Trp | Ser | Arg | Val | Asn | Ile | Pro | Lys | Val | |
| 1 | | | | 5 | | | | | 10 | | | | | 15 | | |

| CTA | AGA | GCT | GCA | GAA | CAA | GCT | CAT | CTT | TGG | GCA | GAC | TGG | TGT | TTT | TGT | 96 |
| Leu | Arg | Ala | Ala | Glu | Gln | Ala | His | Leu | Trp | Ala | Asp | Trp | Cys | Phe | Cys | |
| | | | 20 | | | | | 25 | | | | | 30 | | | |

| ATG | ACA | | | | | | | | | | | | | | | 102 |
| Met | Thr | | | | | | | | | | | | | | | |

(2) INFORMATION FOR SEQ ID NO: 20:

(i) SEQUENCE CHARACTERISTICS:
(A) LENGTH: 219
(B) TYPE: nucleic acid
(C) STRANDEDNESS: double
(D) TOPOLOGY: linear (xi) SEQUENCE DESCRIPTION: SEQ ID NO: 20:

| GTT | AGC | TCT | AGA | GGC | CAT | TCT | TTT | GCT | GAT | CCT | GCC | AGT | AAT | CTT | GGG | 48 |
| Val | Ser | Ser | Arg | Gly | His | Ser | Phe | Ala | Asp | Pro | Ala | Ser | Asn | Leu | Gly | |
| 1 | | | | 5 | | | | | 10 | | | | | 15 | | |

| CTG | GAA | GAC | ATT | ATC | AGG | AAG | GCT | CTC | ATG | GGA | AGC | TTT | GAT | GAC | AAA | 96 |
| Leu | Glu | Asp | Ile | Ile | Arg | Lys | Ala | Leu | Met | Gly | Ser | Phe | Asp | Asp | Lys | |
| | | | 20 | | | | | 25 | | | | | 30 | | | |

| GTT | GAG | GAT | CAT | GGA | GTT | GTC | ATG | TCC | CAG | CCT | ATG | GGA | GTA | GTG | CCT | 144 |
| Val | Glu | Asp | His | Gly | Val | Val | Met | Ser | Gln | Pro | Met | Gly | Val | Val | Pro | |
| | | 35 | | | | | 40 | | | | | 45 | | | | |

| GGT | ACT | GCC | AAC | ACC | GAT | TGC | ATG | TGC | TCC | CTC | TGC | GGT | GAA | CCA | AGC | 192 |
| Gly | Thr | Ala | Asn | Thr | Asp | Cys | Met | Cys | Ser | Leu | Cys | Gly | Glu | Pro | Ser | |
| | 50 | | | | | 55 | | | | | 60 | | | | | |

| AGC | TCC | TCA | CCA | ACA | GAA | CAG | GAT | CTG | | | | | | | | 219 |

```
Ser  Ser  Ser  Pro  Thr  Glu  Gln  Asp  Leu
65                  70
```

( 2 ) INFORMATION FOR SEQ ID NO: 21:

( i ) SEQUENCE CHARACTERISTICS:
        ( A ) LENGTH: 553
        ( B ) TYPE: nucleic acid
        ( C ) STRANDEDNESS: double
        ( D ) TOPOLOGY: linear ( x i ) SEQUENCE DESCRIPTION: SEQ ID NO: 21:

```
AAT  ATC  GAA  CTG  AAG  AAA  GGA  GGG  AAG  GAT  ATA  CCA  GTC  ACT  ATC  CAC      48
Asn  Ile  Glu  Leu  Lys  Lys  Gly  Gly  Lys  Asp  Ile  Pro  Val  Thr  Ile  His
1                   5                        10                       15

AAT  TTA  GAG  GAG  TAT  CTA  AGA  CTG  GTT  ATA  TTC  TGG  GCA  CTA  AAT  GAA      96
Asn  Leu  Glu  Glu  Tyr  Leu  Arg  Leu  Val  Ile  Phe  Trp  Ala  Leu  Asn  Glu
                    20                       25                       30

GGC  GTT  TCT  AGG  CAA  TTT  GAT  TCG  TTC  AGA  GAT  GGA  TTT  GAA  TCA  GTC     144
Gly  Val  Ser  Arg  Gln  Phe  Asp  Ser  Phe  Arg  Asp  Gly  Phe  Glu  Ser  Val
               35                       40                       45

TTC  CCA  CTC  AGT  CAT  CTT  CAG  TAC  TTC  TAC  CCG  GAG  GAA  CTG  GAT  CAG     192
Phe  Pro  Leu  Ser  His  Leu  Gln  Tyr  Phe  Tyr  Pro  Glu  Glu  Leu  Asp  Gln
          50                       55                       60

CTC  CTT  TGT  GGC  AGT  AAA  GCA  GAC  ACT  TGG  GAT  GCA  AAG  ACA  CTG  ATG     240
Leu  Leu  Cys  Gly  Ser  Lys  Ala  Asp  Thr  Trp  Asp  Ala  Lys  Thr  Leu  Met
65                       70                       75                       80

GAA  TGC  TGT  AGG  CCT  GAT  CAT  GGT  TAT  ACT  CAT  GAC  AGT  CGG  GCT  GTG     288
Glu  Cys  Cys  Arg  Pro  Asp  His  Gly  Tyr  Thr  His  Asp  Ser  Arg  Ala  Val
                    85                       90                       95

AAG  TTT  TTG  TTT  GAG  ATT  CTC  AGT  AGT  TTT  GAT  AAT  GAG  CAG  CAG  AGG     336
Lys  Phe  Leu  Phe  Glu  Ile  Leu  Ser  Ser  Phe  Asp  Asn  Glu  Gln  Gln  Arg
               100                      105                      110

TTA  TTT  CTC  CAG  TTT  GTG  ACT  GGT  AGC  CCA  AGA  TTG  CCT  GTT  GGA  GGA     384
Leu  Phe  Leu  Gln  Phe  Val  Thr  Gly  Ser  Pro  Arg  Leu  Pro  Val  Gly  Gly
          115                      120                      125

TTC  CGG  AGT  TTG  AAT  CCA  CCT  TTG  ACA  ATT  GTC  CGA  AAG  ACG  TTT  GAA     432
Phe  Arg  Ser  Leu  Asn  Pro  Pro  Leu  Thr  Ile  Val  Arg  Lys  Thr  Phe  Glu
     130                      135                      140

TCA  ACA  GAA  AAC  CCA  GAT  GAC  TTC  TTG  CCC  TCT  GTA  ATG  ACT  TGT  GTG     480
Ser  Thr  Glu  Asn  Pro  Asp  Asp  Phe  Leu  Pro  Ser  Val  Met  Thr  Cys  Val
145                      150                      155                      160

AAC  TAT  CTT  AAG  TTG  CCG  GAC  TAT  CAA  GCA  TTG  AGA  TAT  GCG  TGA  AAA     528
Asn  Tyr  Leu  Lys  Leu  Pro  Asp  Tyr  Gln  Ala  Leu  Arg  Tyr  Ala       Lys
                    165                      170                      175

ACT  GTT  GAT  AGC  AGC  AAG  AGA  AGG  G                                           553
Thr  Val  Asp  Ser  Ser  Lys  Arg  Arg
               180
```

( 2 ) INFORMATION FOR SEQ ID NO: 22:

( i ) SEQUENCE CHARACTERISTICS:
        ( A ) LENGTH: 186
        ( B ) TYPE: nucleic acid
        ( C ) STRANDEDNESS: double
        ( D ) TOPOLOGY: linear ( x i ) SEQUENCE DESCRIPTION: SEQ ID NO: 22:

```
GAA  GCA  AAA  AAC  GAG  CCC  TGG  AAG  AAG  AAA  AAC  CAC  GCC  GGG  AAA  TCC      48
Glu  Ala  Lys  Asn  Glu  Pro  Trp  Lys  Lys  Lys  Asn  His  Ala  Gly  Lys  Ser
1                   5                        10                       15

TGG  AAA  AAC  GAT  TAC  AGG  AAG  AAA  CTA  GCC  AGA  GGA  GAA  GTT  AAT  AGA      96
Trp  Lys  Asn  Asp  Tyr  Arg  Lys  Lys  Leu  Ala  Arg  Gly  Glu  Val  Asn  Arg
                    20                       25                       30
```

```
AAA  GGA  AGT  AAA  AAT  AAG  GGA  GAG  ACA  AAG  GGC  ACA  GGC  TCG  TCC  TTT       144
Lys  Gly  Ser  Lys  Asn  Lys  Gly  Glu  Thr  Lys  Gly  Thr  Gly  Ser  Ser  Phe
          35                      40                      45

GAC  ACG  CTA  CCT  GCC  TGT  CCG  GAA  GAA  GAC  TTT  GAT  TTG  CGG                 186
Asp  Thr  Leu  Pro  Ala  Cys  Pro  Glu  Glu  Asp  Phe  Asp  Leu  Arg
          50                      55                      60
```

( 2 ) INFORMATION FOR SEQ ID NO: 23:

( i ) SEQUENCE CHARACTERISTICS:
        ( A ) LENGTH: 66
        ( B ) TYPE: nucleic acid
        ( C ) STRANDEDNESS: double
        ( D ) TOPOLOGY: linear ( x i ) SEQUENCE DESCRIPTION: SEQ ID NO: 23:

```
AGG  GTA  CGG  GAA  GCT  GCT  GAA  AAG  GCT  AAG  TCT  GAA  CTC  TCC  TCA  TCT       48
Arg  Val  Arg  Glu  Ala  Ala  Glu  Lys  Ala  Lys  Ser  Glu  Leu  Ser  Ser  Ser
1              5                        10                      15

GTG  CAG  ACT  GAC  ATC  AAT                                                         66
Val  Gln  Thr  Asp  Ile  Asn
               20
```

( 2 ) INFORMATION FOR SEQ ID NO: 24:

( i ) SEQUENCE CHARACTERISTICS:
        ( A ) LENGTH: 192
        ( B ) TYPE: nucleic acid
        ( C ) STRANDEDNESS: double
        ( D ) TOPOLOGY: linear ( x i ) SEQUENCE DESCRIPTION: SEQ ID NO: 24:

```
CAT  TTG  AAT  ATG  AAG  TTG  ACC  CGT  GCT  CAA  TTT  GAA  GGG  ATT  GTC  ACT       48
His  Leu  Asn  Met  Lys  Leu  Thr  Arg  Ala  Gln  Phe  Glu  Gly  Ile  Val  Thr
1              5                        10                      15

GAT  CTA  ATC  AGA  AGG  ACT  ATC  GCT  CCA  TGC  CAA  AAA  GCT  ATG  CAA  GAT       96
Asp  Leu  Ile  Arg  Arg  Thr  Ile  Ala  Pro  Cys  Gln  Lys  Ala  Met  Gln  Asp
               20                       25                      30

GCA  GAA  GTC  AGC  AAG  AGT  GAC  ATA  GGA  GAA  GTG  ATT  CTT  GTG  GGT  GGC       144
Ala  Glu  Val  Ser  Lys  Ser  Asp  Ile  Gly  Glu  Val  Ile  Leu  Val  Gly  Gly
          35                      40                      45

ATG  ACT  AGG  ATG  CCC  AAG  GTT  CAG  CAG  ACT  GTA  CAG  GAC  TTT  TTG  GCA       192
Met  Thr  Arg  Met  Pro  Lys  Val  Gln  Gln  Thr  Val  Gln  Asp  Phe  Leu  Ala
          50                      55                      60
```

( 2 ) INFORMATION FOR SEQ ID NO: 25:

( i ) SEQUENCE CHARACTERISTICS:
        ( A ) LENGTH: 582
        ( B ) TYPE: nucleic acid
        ( C ) STRANDEDNESS: double
        ( D ) TOPOLOGY: linear ( x i ) SEQUENCE DESCRIPTION: SEQ ID NO: 25:

```
GGG  GGC  AGT  GGA  CGA  GGC  CGT  GGC  GAC  CTG  AAG  CAG  GCG  CTT  CCC  TGT       48
Gly  Gly  Ser  Gly  Arg  Gly  Arg  Gly  Asp  Leu  Lys  Gln  Ala  Leu  Pro  Cys
1              5                        10                      15

GTG  GCC  GAG  TCG  CCA  ACG  GTC  CAC  GTG  GAG  GTG  CAT  CAG  CGC  GGC  AGC       96
Val  Ala  Glu  Ser  Pro  Thr  Val  His  Val  Glu  Val  His  Gln  Arg  Gly  Ser
               20                       25                      30

AGC  ACT  GCA  AAG  AAA  GAA  GAC  ATA  AAC  CTG  AGT  GTT  AGA  AAG  CTA  CTC       144
Ser  Thr  Ala  Lys  Lys  Glu  Asp  Ile  Asn  Leu  Ser  Val  Arg  Lys  Leu  Leu
          35                      40                      45

AAC  AGA  CAT  AAT  ATT  GTG  TTT  GGC  GAT  TAC  ACA  TGG  ACT  GAG  TTT  GAT       192
Asn  Arg  His  Asn  Ile  Val  Phe  Gly  Asp  Tyr  Thr  Trp  Thr  Glu  Phe  Asp
```

|  |  |  |  |  |  |  |  |  |  |  |  |  |  |  |  |
|---|---|---|---|---|---|---|---|---|---|---|---|---|---|---|---|
| | | | | 50 | | | | | 55 | | | | | 60 | |

```
GAA  CCT  TTT  TTG  ACC  AGA  AAT  GTG  CAG  TCT  GTG  TCT  ATT  ATT  GAC  ACA        240
Glu  Pro  Phe  Leu  Thr  Arg  Asn  Val  Gln  Ser  Val  Ser  Ile  Ile  Asp  Thr
65             70                       75                       80

GAA  TTA  AAG  GTT  AAA  GAC  TCA  CAG  CCC  ATC  GAT  TTG  AGT  GCA  TGC  ACT        288
Glu  Leu  Lys  Val  Lys  Asp  Ser  Gln  Pro  Ile  Asp  Leu  Ser  Ala  Cys  Thr
                    85                       90                       95

GTT  GCA  CTT  CAC  ATT  TTC  CAG  CTG  AAT  GAA  GAT  GGC  CCC  AGC  AGT  GAA        336
Val  Ala  Leu  His  Ile  Phe  Gln  Leu  Asn  Glu  Asp  Gly  Pro  Ser  Ser  Glu
               100                      105                      110

AAT  CTG  GAG  GAA  GAG  ACA  GAA  AAC  ATA  ATT  GCA  GCA  AAT  CAC  TGG  GTT        384
Asn  Leu  Glu  Glu  Glu  Thr  Glu  Asn  Ile  Ile  Ala  Ala  Asn  His  Trp  Val
          115                      120                      125

CTA  CCT  GCA  GCT  GAA  TTC  CAT  GGG  CTT  TGG  GAC  AGC  TTG  GTA  TAC  GAT        432
Leu  Pro  Ala  Ala  Glu  Phe  His  Gly  Leu  Trp  Asp  Ser  Leu  Val  Tyr  Asp
     130                      135                      140

GTG  GAA  GTC  AAA  TCC  CAT  CTC  CTC  GAT  TAT  GTG  ATG  ACA  ACT  TTA  CTG        480
Val  Glu  Val  Lys  Ser  His  Leu  Leu  Asp  Tyr  Val  Met  Thr  Thr  Leu  Leu
145                      150                      155                      160

TTT  TCA  GAC  AAG  AAC  GTC  AAC  AGC  AAC  CTC  ATC  ACC  ATA  GAG  GGG  TTC        528
Phe  Ser  Asp  Lys  Asn  Val  Asn  Ser  Asn  Leu  Ile  Thr  Ile  Glu  Gly  Phe
                    165                      170                      175

CTC  CAG  GCC  CTG  TCT  CTG  GCA  GTG  GAC  AAG  CAG  TTT  GAA  GAG  AGA  AAG        576
Leu  Gln  Ala  Leu  Ser  Leu  Ala  Val  Asp  Lys  Gln  Phe  Glu  Glu  Arg  Lys
               180                      185                      190

AAG  CTT                                                                              582
Lys  Leu
```

( 2 ) INFORMATION FOR SEQ ID NO: 26:

( i ) SEQUENCE CHARACTERISTICS:
        ( A ) LENGTH: 487
        ( B ) TYPE: nucleic acid
        ( C ) STRANDEDNESS: double
        ( D ) TOPOLOGY: linear ( x i ) SEQUENCE DESCRIPTION: SEQ ID NO: 26:

```
TTC  ACC  ACT  GTG  ATG  GAC  CTG  CTC  CTG  GAG  TAT  GAA  GTC  ATC  TGT  ATC         48
Phe  Thr  Thr  Val  Met  Asp  Leu  Leu  Leu  Glu  Tyr  Glu  Val  Ile  Cys  Ile
1                   5                        10                       15

TAC  TGG  ACC  AAG  TAC  TAC  ACA  CTC  CAC  AAT  GCA  ATC  ATT  GAG  GAT  TGT         96
Tyr  Trp  Thr  Lys  Tyr  Tyr  Thr  Leu  His  Asn  Ala  Ile  Ile  Glu  Asp  Cys
               20                       25                       30

GTC  AGA  AAA  CAG  CTC  AAA  AAA  GAG  AGG  CCC  ATC  ATC  CTG  GAT  CCG  GCC        144
Val  Arg  Lys  Gln  Leu  Lys  Lys  Glu  Arg  Pro  Ile  Ile  Leu  Asp  Pro  Ala
          35                       40                       45

GAC  CCC  ACC  CTC  AAC  GTG  GCA  GAA  GGG  TAC  AGA  TGG  GAC  ATC  GTT  GCT        192
Asp  Pro  Thr  Leu  Asn  Val  Ala  Glu  Gly  Tyr  Arg  Trp  Asp  Ile  Val  Ala
     50                       55                       60

CAG  AGG  GCC  TCC  CAG  TGC  CTG  AAA  CAG  GAC  TGT  TGC  TAT  GAC  AAC  AGG        240
Gln  Arg  Ala  Ser  Gln  Cys  Leu  Lys  Gln  Asp  Cys  Cys  Tyr  Asp  Asn  Arg
65                       70                       75                       80

GAG  AAG  GGG  ATC  TCC  AGC  TGG  AAC  GTG  AAG  AGG  GCA  CGA  GAC  ATC  CAC        288
Glu  Lys  Gly  Ile  Ser  Ser  Trp  Asn  Val  Lys  Arg  Ala  Arg  Asp  Ile  His
                    85                       90                       95

TTG  ACA  GTG  GAG  CAG  AGG  GGT  TAC  CCA  GAT  TTC  AAC  CTC  ATC  GTG  AAC        336
Leu  Thr  Val  Glu  Gln  Arg  Gly  Tyr  Pro  Asp  Phe  Asn  Leu  Ile  Val  Asn
               100                      105                      110

CCT  TAT  GAG  CCC  ATA  AGG  AAG  GTT  AAA  GAG  AAA  ATC  CGG  AGA  CCA  GGG        384
Pro  Tyr  Glu  Pro  Ile  Arg  Lys  Val  Lys  Glu  Lys  Ile  Arg  Arg  Pro  Gly
          115                      120                      125
```

| | | | | | | | | | | | | | | | | |
|---|---|---|---|---|---|---|---|---|---|---|---|---|---|---|---|---|
| GCT | ACT | CTG | GCC | TGC | AGC | GTC | TGT | CCT | TCC | AGG | TTC | CTG | GCA | GTG | AGA | 432 |
| Ala | Thr | Leu | Ala | Cys | Ser | Val | Cys | Pro | Ser | Arg | Phe | Leu | Ala | Val | Arg | |
| | 130 | | | | 135 | | | | | 140 | | | | | | |
| GGC | AGC | TTC | TCA | GCA | GCA | GGT | GCT | CCT | TAG | CCA | AAT | ATG | GGA | TCT | TCT | 480 |
| Gly | Ser | Phe | Ser | Ala | Ala | Gly | Ala | Pro | | Pro | Asn | Met | Gly | Ser | Ser | |
| 145 | | | | | 150 | | | | | 155 | | | | | 160 | |
| CCC | ACA | C | | | | | | | | | | | | | | 487 |
| Pro | Thr | | | | | | | | | | | | | | | |

( 2 ) INFORMATION FOR SEQ ID NO: 27:

( i ) SEQUENCE CHARACTERISTICS:
        ( A ) LENGTH: 768
        ( B ) TYPE: nucleic acid
        ( C ) STRANDEDNESS: double
        ( D ) TOPOLOGY: linear ( x i ) SEQUENCE DESCRIPTION: SEQ ID NO: 27:

| | | | | | | | | | | | | | | | | |
|---|---|---|---|---|---|---|---|---|---|---|---|---|---|---|---|---|
| ATG | GAG | GAT | GAT | TTC | ATG | TGC | GAT | GAT | GAG | GAG | GAC | TAC | GAC | CTG | GAA | 48 |
| Met | Glu | Asp | Asp | Phe | Met | Cys | Asp | Asp | Glu | Glu | Asp | Tyr | Asp | Leu | Glu | |
| 1 | | | | 5 | | | | | 10 | | | | | 15 | | |
| TAC | TCT | GAA | GAT | AGT | AAC | TCC | GAG | CCA | AAT | GTG | GAT | TTG | GAA | AAT | CAG | 96 |
| Tyr | Ser | Glu | Asp | Ser | Asn | Ser | Glu | Pro | Asn | Val | Asp | Leu | Glu | Asn | Gln | |
| | | | 20 | | | | | 25 | | | | | 30 | | | |
| TAC | TAT | AAT | TCC | AAA | GCA | TTA | AAA | GAA | GAT | GAC | CCA | AAA | GCG | GCA | TTA | 144 |
| Tyr | Tyr | Asn | Ser | Lys | Ala | Leu | Lys | Glu | Asp | Asp | Pro | Lys | Ala | Ala | Leu | |
| | | 35 | | | | | 40 | | | | | 45 | | | | |
| AGC | AGT | TTC | CAA | AAG | GTT | TTG | GAA | CTT | GAA | GGT | GAA | AAA | GGA | GAA | TGG | 192 |
| Ser | Ser | Phe | Gln | Lys | Val | Leu | Glu | Leu | Glu | Gly | Glu | Lys | Gly | Glu | Trp | |
| | 50 | | | | | 55 | | | | | 60 | | | | | |
| GGA | TTT | AAA | GCA | CTG | AAA | CAA | ATG | ATT | AAG | ATT | AAC | TTC | AAG | TTG | ACA | 240 |
| Gly | Phe | Lys | Ala | Leu | Lys | Gln | Met | Ile | Lys | Ile | Asn | Phe | Lys | Leu | Thr | |
| 65 | | | | | 70 | | | | | 75 | | | | | 80 | |
| AAC | TTT | CCA | GAA | ATG | ATG | AAT | AGA | TAT | AAG | CAG | CTA | TTG | ACC | TAT | ATT | 288 |
| Asn | Phe | Pro | Glu | Met | Met | Asn | Arg | Tyr | Lys | Gln | Leu | Leu | Thr | Tyr | Ile | |
| | | | | 85 | | | | | 90 | | | | | 95 | | |
| CGG | AGT | GCA | GTC | ACA | AGA | AAT | TAT | TCT | GAA | AAA | TCC | ATT | AAT | TCT | ATT | 336 |
| Arg | Ser | Ala | Val | Thr | Arg | Asn | Tyr | Ser | Glu | Lys | Ser | Ile | Asn | Ser | Ile | |
| | | | 100 | | | | | 105 | | | | | 110 | | | |
| CTT | GAT | TAT | ATC | TCT | ACT | TCT | AAA | CAG | ATG | GAT | TTA | CTG | CAG | GAA | TTC | 384 |
| Leu | Asp | Tyr | Ile | Ser | Thr | Ser | Lys | Gln | Met | Asp | Leu | Leu | Gln | Glu | Phe | |
| | | 115 | | | | | 120 | | | | | 125 | | | | |
| TAT | GAA | ACA | ACA | CTG | GAA | GCT | TTG | AAA | GAT | GCT | AAG | AAT | GAT | AGA | CTG | 432 |
| Tyr | Glu | Thr | Thr | Leu | Glu | Ala | Leu | Lys | Asp | Ala | Lys | Asn | Asp | Arg | Leu | |
| | 130 | | | | | 135 | | | | | 140 | | | | | |
| TGG | TTT | AAG | ACA | AAC | ACA | AAG | CTT | GGA | AAA | TTA | TAT | TTA | GAA | CGA | GAG | 480 |
| Trp | Phe | Lys | Thr | Asn | Thr | Lys | Leu | Gly | Lys | Leu | Tyr | Leu | Glu | Arg | Glu | |
| 145 | | | | | 150 | | | | | 155 | | | | | 160 | |
| GAA | TAT | GGA | AAG | CTT | CAA | AAA | ATT | TTA | CGC | CAG | TTA | CAT | CAG | TCG | TGC | 528 |
| Glu | Tyr | Gly | Lys | Leu | Gln | Lys | Ile | Leu | Arg | Gln | Leu | His | Gln | Ser | Cys | |
| | | | | 165 | | | | | 170 | | | | | 175 | | |
| CAG | ACT | GAT | GAT | GGA | GAA | GAT | GAT | CTG | AAA | AAA | GGT | ACA | CAG | TTA | TTA | 576 |
| Gln | Thr | Asp | Asp | Gly | Glu | Asp | Asp | Leu | Lys | Lys | Gly | Thr | Gln | Leu | Leu | |
| | | | | 180 | | | | | 185 | | | | | 190 | | |
| GAA | ATA | TAT | GCT | TTG | GAA | ATT | CAA | ATG | TAC | ACA | GCA | CAG | AAA | AAT | AAC | 624 |
| Glu | Ile | Tyr | Ala | Leu | Glu | Ile | Gln | Met | Tyr | Thr | Ala | Gln | Lys | Asn | Asn | |
| | | 195 | | | | | 200 | | | | | 205 | | | | |
| AAA | AAA | CTT | AAA | GCA | CTC | TAT | GAA | CAG | TCA | CTT | CAC | ATC | AAG | TCT | GCC | 672 |
| Lys | Lys | Leu | Lys | Ala | Leu | Tyr | Glu | Gln | Ser | Leu | His | Ile | Lys | Ser | Ala | |
| | | 210 | | | | | 215 | | | | | 220 | | | | |
| ATC | CCT | CAT | CCA | CTG | ATT | ATG | GGA | GTT | ATC | AGA | GAA | TGT | GGT | GGT | AAA | 720 |
| Ile | Pro | His | Pro | Leu | Ile | Met | Gly | Val | Ile | Arg | Glu | Cys | Gly | Gly | Lys | |

```
                    225                      230                       235                       240
ATT  GCA  CTT  GGG  GGA  GGT  GAA  TTT  GAA  AAG  GCA  CAC  ACT  GAT  TTT  TTT    768
Ile  Ala  Leu  Gly  Gly  Gly  Glu  Phe  Glu  Lys  Ala  His  Thr  Asp  Phe  Phe
                    245                      250                       255
```

( 2 ) INFORMATION FOR SEQ ID NO: 28:

( i ) SEQUENCE CHARACTERISTICS:
        ( A ) LENGTH: 1121
        ( B ) TYPE: nucleic acid
        ( C ) STRANDEDNESS: double
        ( D ) TOPOLOGY: linear ( x i ) SEQUENCE DESCRIPTION: SEQ ID NO: 28:

```
GCA  GAG  GTT  AAA  ACA  CCT  TTT  GAT  TTG  GCC  AAG  GCA  CAA  GAG  AAC  AGC     48
Ala  Glu  Val  Lys  Thr  Pro  Phe  Asp  Leu  Ala  Lys  Ala  Gln  Glu  Asn  Ser
1                   5                        10                        15

AAC  TCC  GTA  AAG  AAG  AAG  ACA  AAG  TTT  GTC  AAT  TTA  TAC  ACA  AGA  GAA     96
Asn  Ser  Val  Lys  Lys  Lys  Thr  Lys  Phe  Val  Asn  Leu  Tyr  Thr  Arg  Glu
               20                       25                        30

AGA  CAG  GAC  AGG  CTT  GCA  GTC  CTG  CTC  CCT  GGT  CGT  CAC  CCT  TGT  GAT    144
Arg  Gln  Asp  Arg  Leu  Ala  Val  Leu  Leu  Pro  Gly  Arg  His  Pro  Cys  Asp
          35                        40                        45

TGC  CTG  GGC  CAG  AAG  CAC  AAG  CTC  ATC  AAT  AAC  TGT  CTG  ATC  TGT  GGG    192
Cys  Leu  Gly  Gln  Lys  His  Lys  Leu  Ile  Asn  Asn  Cys  Leu  Ile  Cys  Gly
     50                        55                        60

CGC  ATT  GTC  TGT  GAA  CAA  GAA  GGC  TCA  GGC  CCT  TGC  TTA  TTC  TGT  GGC    240
Arg  Ile  Val  Cys  Glu  Gln  Glu  Gly  Ser  Gly  Pro  Cys  Leu  Phe  Cys  Gly
65                       70                        75                        80

ACT  CTG  GTG  TGT  ACT  CAT  GAG  GAA  CAA  GAT  ATT  TTA  CAG  CGT  GAC  TCA    288
Thr  Leu  Val  Cys  Thr  His  Glu  Glu  Gln  Asp  Ile  Leu  Gln  Arg  Asp  Ser
               85                        90                        95

AAC  AAG  AGC  CAG  AAA  CTG  CTA  AAG  AAA  CTC  ATG  TCA  GGA  GTG  GAG  AAT    336
Asn  Lys  Ser  Gln  Lys  Leu  Leu  Lys  Lys  Leu  Met  Ser  Gly  Val  Glu  Asn
          100                       105                       110

TCT  GGA  AAG  GTG  GAC  ATC  TCT  ACC  AAG  GAC  CTT  CTT  CCT  CAT  CAA  GAA    384
Ser  Gly  Lys  Val  Asp  Ile  Ser  Thr  Lys  Asp  Leu  Leu  Pro  His  Gln  Glu
     115                       120                       125

TTG  CGA  ATT  AAG  TCT  GGT  CTG  GAG  AAG  GCT  ATC  AAG  CAT  AAA  GAC  AAA    432
Leu  Arg  Ile  Lys  Ser  Gly  Leu  Glu  Lys  Ala  Ile  Lys  His  Lys  Asp  Lys
130                       135                       140

CTG  TTA  GAG  TTT  GAC  AGA  ACT  AGT  ATT  CGA  AGG  ACC  CAA  GTC  ATT  GAT    480
Leu  Leu  Glu  Phe  Asp  Arg  Thr  Ser  Ile  Arg  Arg  Thr  Gln  Val  Ile  Asp
145                       150                       155                       160

GAT  GAG  TCA  GAT  TAC  TTT  GCC  AGT  GAT  TCT  AAC  CAA  TGG  TTG  TCC  AAA    528
Asp  Glu  Ser  Asp  Tyr  Phe  Ala  Ser  Asp  Ser  Asn  Gln  Trp  Leu  Ser  Lys
                    165                       170                       175

CTT  GAG  CGG  GAA  ACC  TTG  CAG  AAG  CGA  GAG  GAG  GAG  CTG  AGA  GAA  CTT    576
Leu  Glu  Arg  Glu  Thr  Leu  Gln  Lys  Arg  Glu  Glu  Glu  Leu  Arg  Glu  Leu
               180                       185                       190

CGA  CAC  GCC  TCT  CGA  CTT  TCT  AAG  AAG  GTC  ACC  ATT  GAC  TTT  GCA  GGA    624
Arg  His  Ala  Ser  Arg  Leu  Ser  Lys  Lys  Val  Thr  Ile  Asp  Phe  Ala  Gly
          195                       200                       205

AGG  AAG  ATC  CTG  GAA  GAA  GAA  AAT  TCA  CTA  GCA  GAG  TAT  CAT  AGC  AGA    672
Arg  Lys  Ile  Leu  Glu  Glu  Glu  Asn  Ser  Leu  Ala  Glu  Tyr  His  Ser  Arg
     210                       215                       220

CTA  GAT  GAG  ACA  ATA  CAG  GCC  ATT  GCC  AAT  GGA  ACC  TTG  AAC  CAG  CCA    720
Leu  Asp  Glu  Thr  Ile  Gln  Ala  Ile  Ala  Asn  Gly  Thr  Leu  Asn  Gln  Pro
225                       230                       235                       240

CTG  ACC  AAA  TTG  GAT  AGA  TCT  TCT  GAA  GAG  CCT  TTG  GGA  GTT  CTG  GTA    768
Leu  Thr  Lys  Leu  Asp  Arg  Ser  Ser  Glu  Glu  Pro  Leu  Gly  Val  Leu  Val
                    245                       250                       255
```

| | | | | | | | | | | | | | | | | |
|---|---|---|---|---|---|---|---|---|---|---|---|---|---|---|---|---|
| AAT | CCC | AAC | ATG | TAC | CAG | TCC | CCT | CCC | CAG | TGG | TTG | ACC | ACA | CAG | GTG | 816 |
| Asn | Pro | Asn | Met | Tyr | Gln | Ser | Pro | Pro | Gln | Trp | Leu | Thr | Thr | Gln | Val | |
| | | | 260 | | | | | 265 | | | | | 270 | | | |
| CAG | CCT | CAC | AGA | AGA | AGG | CTT | TCC | GTT | CTT | CAG | GAT | TTG | GAC | TAG | AGT | 864 |
| Gln | Pro | His | Arg | Arg | Arg | Leu | Ser | Val | Leu | Gln | Asp | Leu | Asp | | Ser | |
| | | 275 | | | | | 280 | | | | | 285 | | | | |
| TCA | ACT | CAT | TTC | AGC | ACC | AGT | TGC | GAA | TCC | AGG | ATC | AAG | AAT | TTC | AGG | 912 |
| Ser | Thr | His | Phe | Ser | Thr | Ser | Cys | Glu | Ser | Arg | Ile | Lys | Asn | Phe | Arg | |
| | 290 | | | | | 295 | | | | | 300 | | | | | |
| AAG | GCT | TTG | ATG | GTG | GCT | GGT | GCC | TCT | CTG | TAC | ATC | AGC | CCT | GGG | TTC | 960 |
| Lys | Ala | Leu | Met | Val | Ala | Gly | Ala | Ser | Leu | Tyr | Ile | Ser | Pro | Gly | Phe | |
| 305 | | | | | 310 | | | | | 315 | | | | | 320 | |
| TCT | GCT | TGT | CAG | AGG | GAT | TAA | AAG | GGT | GGA | GGG | CAG | ATC | CTG | GTA | CAC | 1008 |
| Ser | Ala | Cys | Gln | Arg | Asp | | Lys | Gly | Gly | Gly | Gln | Ile | Leu | Val | His | |
| | | | | 325 | | | | | 330 | | | | | 335 | | |
| CCC | CCA | CAG | AGG | ACG | ACT | TTG | GAT | AGC | AGC | CAC | AGC | TAA | AAA | ATC | CCT | 1056 |
| Pro | Pro | Gln | Arg | Thr | Thr | Leu | Asp | Ser | Ser | His | Ser | | Lys | Ile | Pro | |
| | | | 340 | | | | | 345 | | | | | 350 | | | |
| CCC | CTC | AAG | AAG | TCT | CAG | AAC | TCC | AGG | CTA | CAT | ATC | GTC | TTC | TTC | GTT | 1104 |
| Pro | Leu | Lys | Lys | Ser | Gln | Asn | Ser | Arg | Leu | His | Ile | Val | Phe | Phe | Val | |
| | | 355 | | | | | 360 | | | | | 365 | | | | |
| GGG | AAG | ATG | TGG | AAT | TT | | | | | | | | | | | 1121 |
| Gly | Lys | Met | Trp | Asn | | | | | | | | | | | | |
| | 370 | | | | | | | | | | | | | | | |

( 2 ) INFORMATION FOR SEQ ID NO: 29:

( i ) SEQUENCE CHARACTERISTICS:
        ( A ) LENGTH: 108
        ( B ) TYPE: nucleic acid
        ( C ) STRANDEDNESS: double
        ( D ) TOPOLOGY: linear ( x i ) SEQUENCE DESCRIPTION: SEQ ID NO: 29:

| | | | | | | | | | | | | | | | | |
|---|---|---|---|---|---|---|---|---|---|---|---|---|---|---|---|---|
| GAA | AGG | GCC | CTG | ACA | GCA | CAC | ACA | CTT | AAA | CAC | AGT | TTT | CTG | ATA | ACT | 48 |
| Glu | Arg | Ala | Leu | Thr | Ala | His | Thr | Leu | Lys | His | Ser | Phe | Leu | Ile | Thr | |
| 1 | | | | 5 | | | | | 10 | | | | | 15 | | |
| TTG | GAA | TTC | ACA | CCG | TTG | GAC | TAG | TTA | AAA | ACT | TCT | AAA | ATA | ATT | TTT | 96 |
| Leu | Glu | Phe | Thr | Pro | Leu | Asp | | Leu | Lys | Thr | Ser | Lys | Ile | Ile | Phe | |
| | | | 20 | | | | | 25 | | | | | 30 | | | |
| TAA | AAT | CTA | ATA | | | | | | | | | | | | | 108 |
| | Asn | Leu | Ile | | | | | | | | | | | | | |
| | | 35 | | | | | | | | | | | | | | |

( 2 ) INFORMATION FOR SEQ ID NO: 30:

( i ) SEQUENCE CHARACTERISTICS:
        ( A ) LENGTH: 219
        ( B ) TYPE: nucleic acid
        ( C ) STRANDEDNESS: double
        ( D ) TOPOLOGY: linear ( x i ) SEQUENCE DESCRIPTION: SEQ ID NO: 30:

| | | | | | | | | | | | | | | | | |
|---|---|---|---|---|---|---|---|---|---|---|---|---|---|---|---|---|
| CCA | GGA | ACT | GAG | ATC | TTT | AAT | CTG | CCA | GCA | GTT | ACT | ACG | TCA | GGC | TCA | 48 |
| Pro | Gly | Thr | Glu | Ile | Phe | Asn | Leu | Pro | Ala | Val | Thr | Thr | Ser | Gly | Ser | |
| 1 | | | | 5 | | | | | 10 | | | | | 15 | | |
| GTT | AGC | TCT | AGA | GGC | CAT | TCT | TTT | GCT | GAT | CCT | GCC | AGT | AAT | CTT | GGG | 96 |
| Val | Ser | Ser | Arg | Gly | His | Ser | Phe | Ala | Asp | Pro | Ala | Ser | Asn | Leu | Gly | |
| | | | 20 | | | | | 25 | | | | | 30 | | | |
| CTG | GAA | GAC | ATT | ATC | AGG | AAG | GCT | CTC | ATG | GGA | AGC | TTT | GAT | GAC | AAA | 144 |
| Leu | Glu | Asp | Ile | Ile | Arg | Lys | Ala | Leu | Met | Gly | Ser | Phe | Asp | Asp | Lys | |
| | | | 35 | | | | | 40 | | | | | 45 | | | |
| GTT | GAG | GAT | CAT | GGA | GTT | GTC | ATG | TCC | CAG | CCT | ATG | GGA | GTA | GTG | CCT | 192 |

-continued

```
Val  Glu  Asp  His  Gly  Val  Val  Met  Ser  Gln  Pro  Met  Gly  Val  Val  Pro
     50                       55                  60

GGT  ACT  GCC  AAC  ACC  TCA  GTT  GTG  ACC                                         219
Gly  Thr  Ala  Asn  Thr  Ser  Val  Val  Thr
65                       70
```

( 2 ) INFORMATION FOR SEQ ID NO: 31:

( i ) SEQUENCE CHARACTERISTICS:
      ( A ) LENGTH: 223
      ( B ) TYPE: amino acid
      ( C ) STRANDEDNESS:
      ( D ) TOPOLOGY: linear ( x i ) SEQUENCE DESCRIPTION: SEQ ID NO: 31:

```
Leu  Gln  Leu  Glu  Ala  Glu  Asn  Tyr  Glu  Gly  His  Thr  Pro  Leu  His  Val
1                    5                    10                       15

Ala  Val  Ile  His  Lys  Asp  Val  Glu  Met  Val  Arg  Leu  Leu  Arg  Asp  Ala
               20                  25                       30

Gly  Ala  Asp  Leu  Asp  Lys  Pro  Glu  Pro  Thr  Cys  Gly  Arg  Ser  Pro  Phe
          35                  40                       45

Ile  Trp  Leu  Asp  Leu  Glu  Ala  Arg  Asn  Tyr  Asp  Gly  Leu  Thr  Ala  Leu
     50                       55                  60

His  Val  Ala  Val  Asn  Thr  Glu  Cys  Gln  Glu  Thr  Val  Gln  Leu  Leu  Leu
65                       70                  75                            80

Glu  Arg  Gly  Ala  Asp  Ile  Asp  Val  Asp  Ile  Lys  Ser  Gly  Arg  Ser  Pro
               85                  90                            95

Leu  Ile  His  Gln  Trp  Arg  Pro  Gly  Ser  Arg  Cys  Ala  Gly  Ala  Ser  Leu
                    100                 105                      110

Arg  Ala  Gly  Ala  Asn  Pro  Ala  Ala  Arg  Met  Tyr  Gly  Gly  Arg  Thr  Pro
          115                      120                 125

Leu  Gly  Ser  Ala  Met  Leu  Arg  Pro  Asn  Pro  Ile  Leu  Ala  Arg  Leu  Leu
     130                      135                      140

Arg  Ala  Val  Glu  Asn  Asn  Ser  Leu  Ser  Met  Val  Gln  Leu  Leu  Leu  Gln
145                      150                 155                            160

His  Gly  Ala  Asn  Val  Asn  Ala  Gln  Met  Ser  Gly  Ser  Ser  Ala  Leu  His
               165                      170                      175

Ser  Ala  Ser  Gly  Arg  Gly  Leu  Leu  Pro  Leu  Val  Arg  Thr  Leu  Val  Ala
          180                      185                      190

His  Gly  Ala  Pro  Glu  Pro  Glu  Gly  Lys  Asp  Glu  Lys  Ser  Gly  Pro  Arg
          195                      200                 205

Ser  Gly  Ala  Asp  Ser  Ser  Leu  Lys  Asn  Cys  His  Asn  Asp  Thr  Pro
     210                      215                      220
```

What is claimed is:

1. A method for determining whether a test protein is capable of interacting with a nuclear hormone receptor protein in a ligand-dependent manner, comprising:

(a) providing a host cell which contains
   (i) a reporter gene operably linked to a protein binding site;
   (ii) a first fusion gene which expresses a first fusion protein, said first fusion protein comprising a nuclear hormone receptor protein covalently bonded to a binding moiety which is capable of specifically binding to said protein binding site; and
   (iii) a second fusion gene which expresses a second fusion protein, said second fusion protein comprising said test protein covalently bonded to a weak gene activating moiety;

(b) measuring reporter gene expression in the presence and in the absence of said ligand; and (c) determining whether expression of said reporter gene is increased in the presence of said ligand, increased expression being an indication that said test protein interacts with said nuclear hormone receptor protein in a ligand-dependent manner.

2. A method for determining whether a test protein is capable of interacting with a nuclear hormone receptor protein in a ligand-sensitive manner, comprising:

(a) providing a host cell which contains
   (i) a reporter gene operably linked to a protein binding site;
   (ii) a first fusion gene which expresses a first fusion protein, said first fusion protein comprising a nuclear hormone receptor protein covalently bonded to a binding moiety which is capable of specifically binding to said protein binding site; and (iii) a second fusion gene which expresses a second fusion protein, said second fusion protein comprising said test protein covalently bonded to a weak gene activating moiety;

(b) measuring reporter gene expression in the presence and in the absence of said ligand; and (c) determining whether expression of said reporter gene is decreased in the presence of said ligand, decreased expression being an indication that said test protein interacts with said nuclear hormone receptor protein in a ligand-sensitive manner.

3. The method of claims 1 or 2, wherein said weak gene activating moiety is the gene activating moiety of B42.

4. The method of claims 1 or 2, wherein said nuclear hormone receptor is a thyroid hormone receptor.

5. The method of claims 1 or 2, wherein said ligand is a thyroid hormone.

* * * * *

UNITED STATES PATENT AND TRADEMARK OFFICE
CERTIFICATE OF CORRECTION

PATENT NO.    : 5,846,711                                          Page 1 of 1
DATED         : December 8, 1998
INVENTOR(S)   : David D. Moore and Jae Woon Lee It is certified that error appears in the above-identified patent and that said Letters Patent is hereby corrected as shown below:

<u>Title page,</u>
Item [21], before "222,719" insert -- 08/ --;

<u>Column 2,</u>
Line 31, delete "(" before "Curran";
Line 58, replace "Pit1" with -- Pit-1 --;

<u>Column 8,</u>
Line 37, replace "promoters" with -- promoter. --;

<u>Column 11,</u>
Line 23, replace "±-" with -- +/- --;
Line 25, replace "+" with -- $^{-/+}$ --;

<u>Column 12,</u>
Line 27, either replace "155"" with -- 1555 --;

<u>Column 14,</u>
Line 25, replace "suPra" with -- supra --;
Line 31, replace "Moll." with -- Mol. --;
Line 34, replace "Pit1" with -- Pit-1 --;

<u>Column 16,</u>
Line 3, replace "promotor" with -- promoter --;

Signed and Sealed this

Seventeenth Day of September, 2002

*Attest:*

JAMES E. ROGAN
*Attesting Officer*    *Director of the United States Patent and Trademark Office*